United States Patent
Naidu et al.

(10) Patent No.: US 9,580,431 B2
(45) Date of Patent: Feb. 28, 2017

(54) INHIBITORS OF HUMAN IMMUNODEFICIENCY VIRUS REPLICATION

(71) Applicant: ViiV HEALTHCARE UK (NO.5) LIMITED, Brentford, Middlesex (GB)

(72) Inventors: B. Narasimhulu Naidu, Durham, CT (US); Manoj Patel, Berlin, CT (US); Kevin Peese, Haddam, CT (US); Zhongyu Wang, Tolland, CT (US)

(73) Assignee: ViiV Healthcare UK (No.5) Limited, Brentford, Middlesex (GB)

( * ) Notice: Subject to any disclaimer, the term of this patent is extended or adjusted under 35 U.S.C. 154(b) by 0 days.

(21) Appl. No.: 14/772,146

(22) PCT Filed: Mar. 10, 2014

(86) PCT No.: PCT/US2014/022501
§ 371 (c)(1),
(2) Date: Sep. 2, 2015

(87) PCT Pub. No.: WO2014/164467
PCT Pub. Date: Oct. 9, 2014

(65) Prior Publication Data
US 2016/0016960 A1 Jan. 21, 2016

Related U.S. Application Data

(60) Provisional application No. 61/779,858, filed on Mar. 13, 2013.

(51) Int. Cl.
| | |
|---|---|
| *C07D 487/04* | (2006.01) |
| *A61K 31/519* | (2006.01) |
| *A61K 45/06* | (2006.01) |

(52) U.S. Cl.
CPC .......... *C07D 487/04* (2013.01); *A61K 31/519* (2013.01); *A61K 45/06* (2013.01)

(58) Field of Classification Search
CPC .......................... A61K 31/519; C07D 487/04
See application file for complete search history.

(56) References Cited

U.S. PATENT DOCUMENTS

| | | | |
|---|---|---|---|
| 8,633,200 B2 * | 1/2014 | Pendri | C07D 487/04 514/259.3 |
| 8,791,108 B2 * | 7/2014 | Naidu | C07D 487/04 514/230.5 |
| 9,034,882 B2 * | 5/2015 | Pendri | C07D 519/00 514/259.3 |

FOREIGN PATENT DOCUMENTS

| | | | | |
|---|---|---|---|---|
| WO | WO 2011076765 A1 * | 6/2011 | | C07D 487/04 |
| WO | WO 2012/065963 A2 | 5/2012 | | |

\* cited by examiner

*Primary Examiner* — Theodore R West
(74) *Attorney, Agent, or Firm* — Robert H. Brink; R. Steven Thomas; Edward R. Gimmi

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

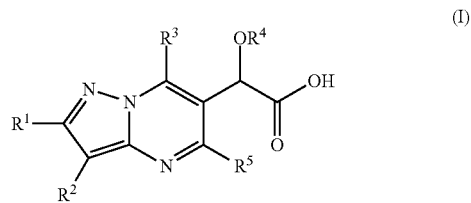

(I)

13 Claims, No Drawings

INHIBITORS OF HUMAN IMMUNODEFICIENCY VIRUS REPLICATION

CROSS-REFERENCE TO RELATED APPLICATIONS

This application claims priority to U.S. Provisional Patent Application Ser. No. 61/779,858, filed Mar. 13, 2013, which is incorporated by reference in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33.3 million people worldwide are infected with the virus (UNAIDS Report on the Global AIDS Epidemic 2010). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med*. 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012003497, WO2012003498, WO2012033735, WO2012065963 and WO2012066442

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

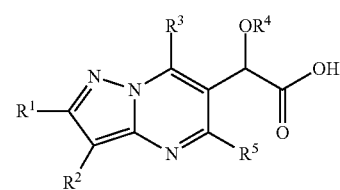

where:
$R^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, or benzimidazolyl, and is substituted with 0-3 substituents selected from halo, alkyl, haloalkyl, alkenyl, $Ar^1$, $(Ar^1)$alkyl, and $(Ar^1)O$;
or $R^1$ is pyrrolidinonyl, oxazolidinonyl, or imidazolonyl, and is substituted with 0-1 substituents selected from $Ar^1$, $(Ar^1)$alkyl, and $(Ar^1)O$;
$R^2$ is hydrogen, halo, or alkyl;
$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
$R^4$ is alkyl or haloalkyl;
$R^5$ is alkyl; and Ar$^1$ is phenyl substituted with 0-3 substituents selected from halo, cyano, alkyl, haloalkyl, alkoxy, haloalkoxy, and alkenyloxy;

or a pharmaceutically acceptable salt thereof.

Another aspect of the invention is a compound of Formula I where

R$^1$ is is thienyl, pyrazolyl, imidazolyl, oxazolyl, thiazolyl, oxadiazolyl, indolyl, benzofuranyl, benzothiophenyl, or benzimidazolyl, and is substituted with 0-3 substituents selected from halo, alkyl, haloalkyl, alkenyl, Ar$^1$, (Ar$^1$)alkyl, and (Ar$^1$)O;

or R$^1$ is pyrrolidinonyl, oxazolidinonyl, or imidazolonyl, and is substituted with 0-1 substituents selected from Ar$^1$, (Ar$^1$)alkyl, and (Ar$^1$)O;

R$^2$ is hydrogen, halo, or alkyl;

R$^3$ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

or R$^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

R$^4$ is alkyl or haloalkyl;

R$^5$ is alkyl; and

Ar$^1$ is phenyl substituted with 0-3 substituents selected from halo, cyano, alkyl, haloalkyl, alkoxy, haloalkoxy, and alkenyloxy;

or a pharmaceutically acceptable salt thereof.

Another aspect of the invention is a compound of Formula I where R$^1$ is thienyl, pyrazolyl, imidazolyl, oxazolyl, thiazolyl, oxadiazolyl, indolyl, benzofuranyl, benzothiophenyl, or benzimidazolyl, and is substituted with 0-3 substituents selected from halo, alkyl, haloalkyl, alkenyl, Ar$^1$, (Ar$^1$)alkyl, and (Ar$^1$)O.

Another aspect of the invention is a compound of Formula I where R$^1$ is pyrrolidinonyl, oxazolidinonyl, or imidazolonyl, and is substituted with 0-1 substituents selected from Ar$^1$, (Ar$^1$)alkyl, and (Ar$^1$)O.

Another aspect of the invention is a compound of Formula I where R$^2$ is hydrogen.

Another aspect of the invention is a compound of Formula I where R$^3$ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of Formula I where R$^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of Formula I where R$^4$ is alkyl.

For a compound of Formula I, the scope of any instance of a variable substituent, including R$^1$, R$^2$, R$^3$, R$^4$, and Ar$^1$ can be used independently with the scope of any other instance of a variable substituent.

Unless specified otherwise, these terms have the following meanings "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes fluoro, chloro, bromo, and iodo. "Halo" includes all halogenated isomers from monohalo substituted to perhalo substituted in substituents defined with halo, for example, "Haloalkyl" and "haloalkoxy", "halophenyl", "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication.

A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press.1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 1.

TABLE 1

| Example | $EC_{50}$ μM |
|---|---|
| 1 | 0.047 |
| 2 | 0.050 |
| 3 | 0.100 |
| 4 | 0.133 |
| 5 | 0.003 |
| 6 | 0.006 |
| 7 | 0.028 |
| 8 | 0.011 |
| 9 | 0.028 |
| 10 | 0.019 |
| 11 | 0.082 |
| 12 | 0.013 |
| 13 | 0.014 |
| 14 | 0.027 |
| 15 | 0.019 |
| 16 | 0.038 |
| 17 | 0.013 |
| 18 | 0.143 |
| 19 | 0.105 |
| 20 | 0.877 |
| 21 | 0.075 |
| 22 | 0.012 |
| 23 | 0.012 |
| 24 | 0.026 |
| 25 | 0.023 |
| 26 | 0.145 |
| 27 | 0.478 |
| 28 | 0.152 |
| 29 | 0.006 |
| 30 | 0.016 |
| 31 | 0.813 |
| 32 | 0.339 |
| 33 | 0.011 |
| 34 | 0.026 |
| 35 | 0.573 |
| 36 | 0.084 |
| 37 | 0.011 |
| 38 | 0.023 |
| 39 | 0.007 |
| 40 | 0.011 |
| 41 | 0.015 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compound I-1 and I-2 are commercially available or synthesized by reactions well known in the art. Intermediates I-3 can be prepared by procedure well known in the art or as set forth in the examples below using compound I-1 and compound I-2. Intermediates I-3 are conveniently transformed to intermediates I-5 via intermediates I-4 using conditions well-known to those skilled in the art. Intermediates I-5 are oxidized to intermediates I-6 by reactions well-known in the art, including but not limited to Davis oxidation. Intermediates I-6 are oxidized to intermediates I-7 by a well-known conditions, including but not limited to Dess-Martin oxidation. Intermediates I-7 are reduced to chiral intermediates I-8 using well-known conditions in the presence of catalytic chiral ligands. Intermediates I-8 are converted to the intermediates I-9 by well-known conditions, including but not limited to tertiary-butyl acetate and perchloric acid. Intermediates I-9 are conveniently transformed to intermediates I-10 using conditions well-known in the art, including but not limited to the Suzuki coupling between intermediates I-9 and R$_4$—B(OR)$_2$. The boronate or boronic acid coupling reagents are commercially available or are prepared by reactions well-known to those skilled in the art (PCT Appln. WO20090662285). The diester intermediates I-10 are regioselectively converted to monocaboxylic acid intermediates I-11 by methods well-known in the art. Intermediates I-11 are conveniently converted to intermediates I-12 by conditions well-known to those skilled in the art, including but not limited to HATU and appropriate base followed by cyclization under acidic conditions. The intermediates I-12 were transformed to final compounds I-13 by conditions well known in the literature. In addition, the intermediates I-12 could also be transformed to final compound I-13 by alkylation using conditions well to those skilled in art followed by hydrolysis.

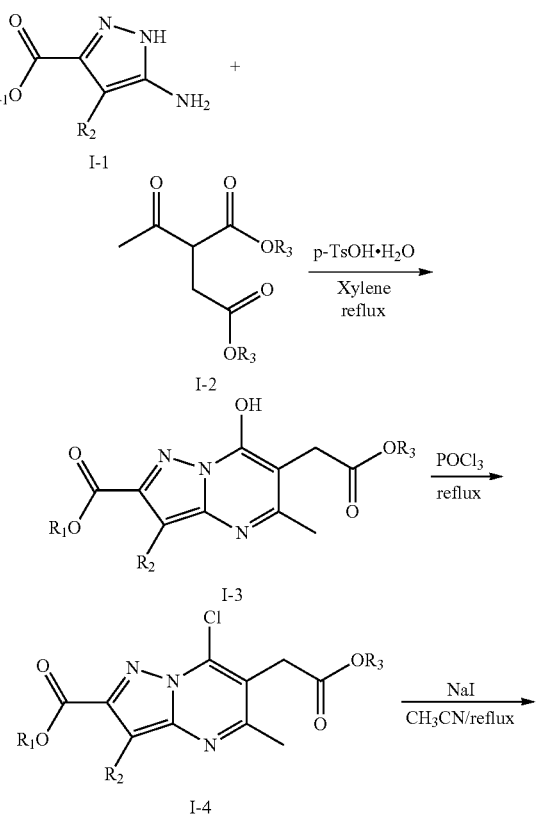

Scheme I.

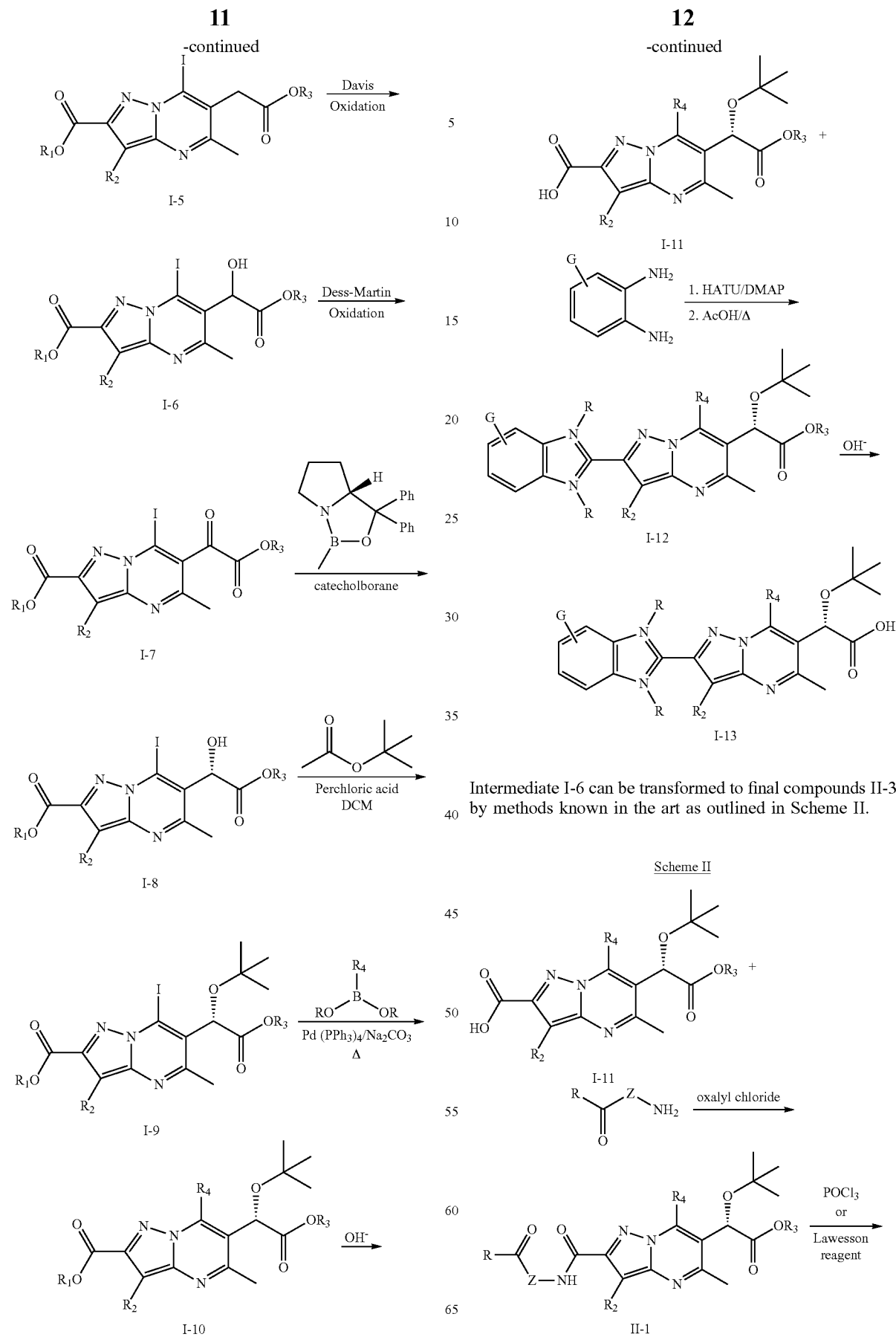
Intermediate I-6 can be transformed to final compounds II-3 by methods known in the art as outlined in Scheme II.
Scheme II -continued
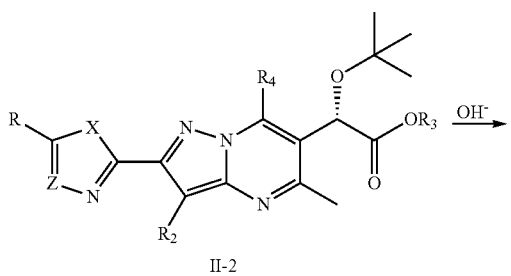
II-2
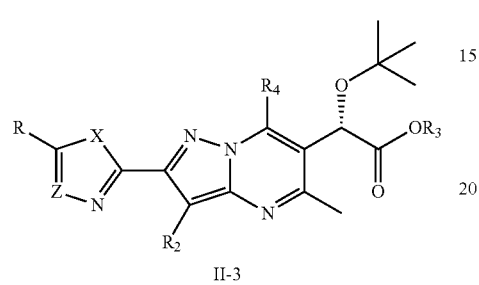
II-3
Intermediates I-9 can be transformed to final compounds III-6 by methods known in the art as outlined in Scheme III.
Scheme III
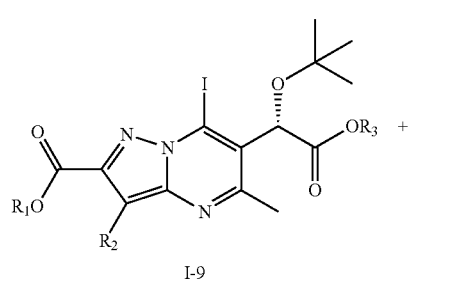
I-9
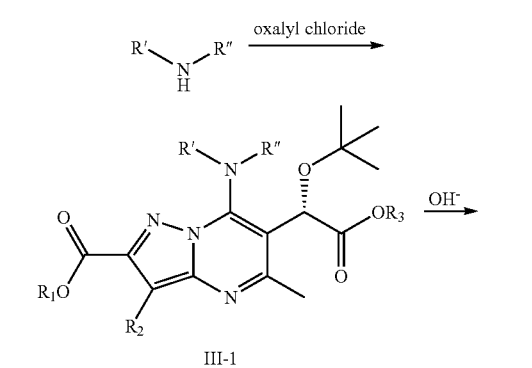
III-1
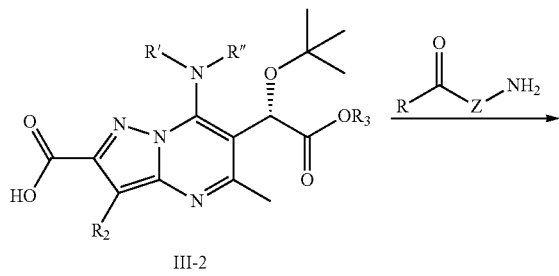
III-2
-continued
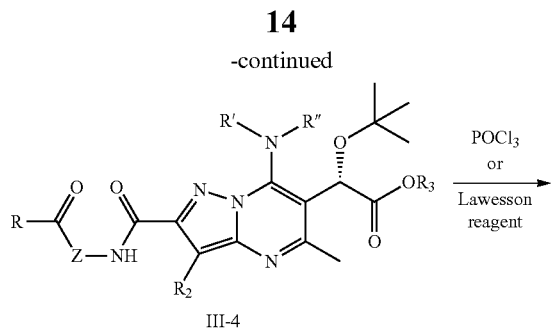
III-4
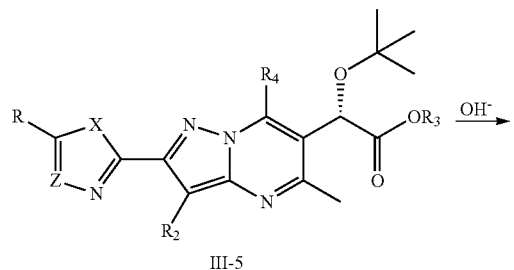
III-5
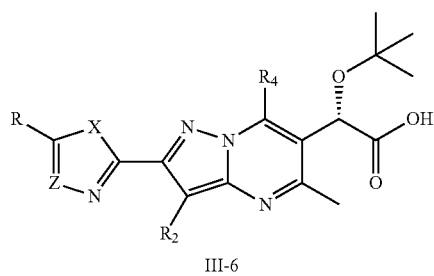
III-6
Intermediates IV-1 can be transformed to final compounds IV-8 by methods known in the art as outlined in Scheme IV.
Scheme IV
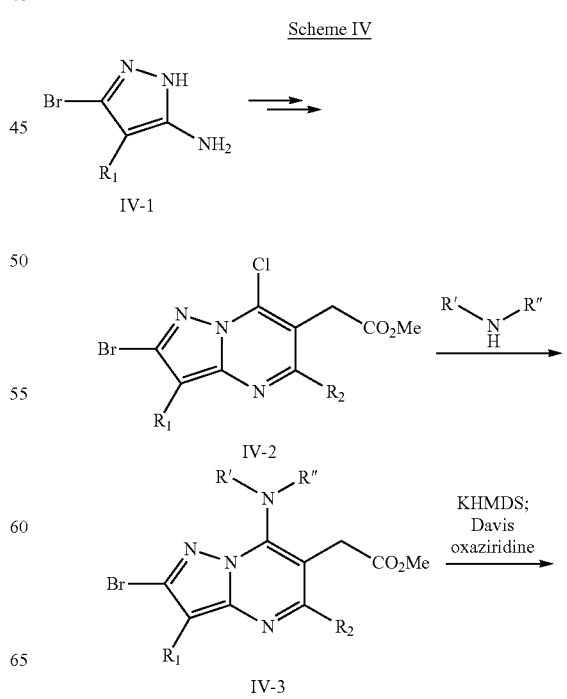
IV-1
IV-2
IV-3

-continued

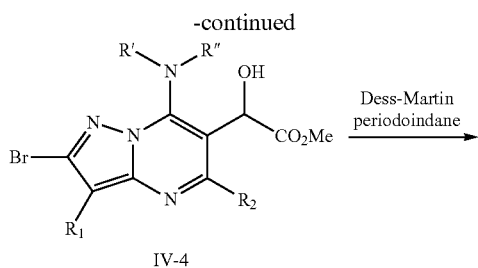

IV-4

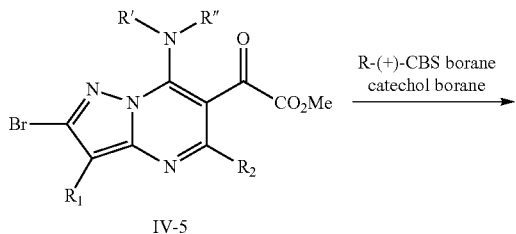

IV-5

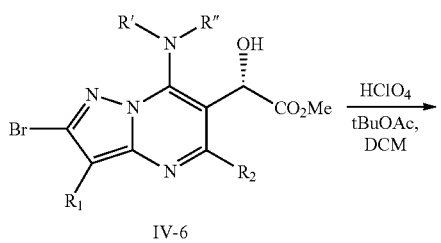

IV-6

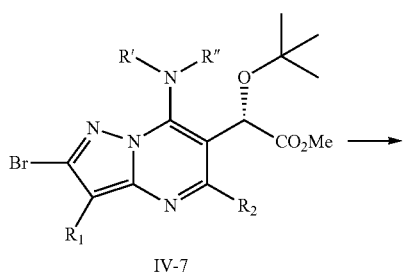

IV-7

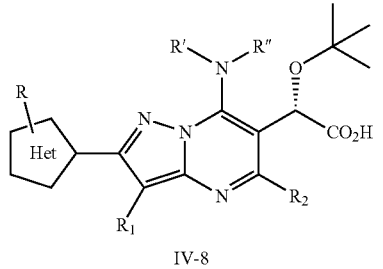

IV-8

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 9:1 H$_2$O/acetonitrile with 10 mM NH$_4$OAc and mobile phase B:A:9:1 acetonitrile/H$_2$O with: 10 mM NH$_4$OAc or mobile phase A: 95:5 H$_2$O/MeOH with 20 mM NH$_4$OAc and mobile phase B: 95:5 MeOH/H$_2$O with 20 mM NH$_4$OAc.

Intermediate 1

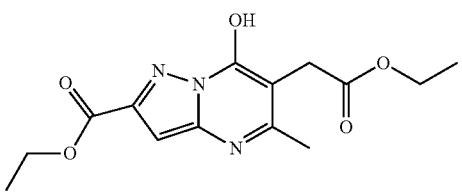 [SMILES: CCOC(=O)Cc1c(C)nc2cc(C(=O)OCC)nn2c1O]

Ethyl 6-(2-ethoxy-2-oxoethyl)-7-hydroxy-5-methyl-pyrazolo[1,5-a]pyrimidine-2-carboxylate A suspension of ethyl 5-amino-1H-pyrazole-3-carboxylate (35.5 g, 229 mmol, prepared according to WO 2008015271), diethyl 2-acetylsuccinate (51.2 mL, 275 mmol) and TsOH.H$_2$O (0.218 g, 1.144 mmol) in o-xylene (500 mL) was refluxed using a Dean-Stork condensor for 5 h. (Note: The suspension turned into a clear homogeneous solution and then in about 15 min a yellow solid started precipitated out of solution). Then, the reaction mixture was cooled, diluted with hexanes (250 mL), filtered, washed with hexanes and dried to afford ethyl 6-(2-ethoxy-2-oxoethyl)-7-hydroxy-5-methylpyrazolo[1,5-a]pyrimidine-2-carboxylate (53 g, 75% yield) as light yellow solid. $^1$H NMR (500 MHz, DMSO-d$_6$) δ 12.61 (br. s., 1H), 6.49 (s, 1H), 4.34 (q, J=7.1 Hz, 2H), 4.09 (q, J=7.1 Hz, 2H), 3.57 (s, 2H), 2.34 (s, 3H), 1.33 (t, J=7.2 Hz, 3H), 1.19 (t, J=7.0 Hz, 3H). LCMS (M+1)=308.04.

Intermediate 2

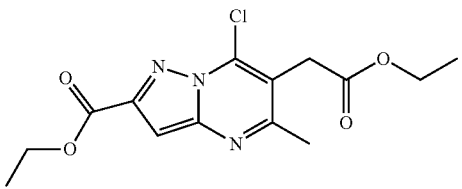 [SMILES: CCOC(=O)Cc1c(C)nc2cc(C(=O)OCC)nn2c1Cl]

Ethyl 7-chloro-6-(2-ethoxy-2-oxoethyl)-5-methyl-pyrazolo[1,5-a]pyrimidine-2-carboxylate A mixture of ethyl 6-(2-ethoxy-2-oxoethyl)-7-hydroxy-5-methylpyrazolo[1,5-a]pyrimidine-2-carboxylate (25 g, 81 mmol), and N,N-dimethylaniline (20.6 mL, 163 mmol) in POCl$_3$ (100 mL) was heated at 120° C. for 3 h. Then the reaction was cooled to rt and concentrated in vacuo to half the volume. It was poured into a large quantity of ice water and stirred for 20 min. Precepitates formed and were collected by filtration. This solid was dissolved in ethyl acetate (1 L) and washed with water. The aqueous phase was back-extracted with ethyl acetate and the combined organic layers were washed with brine (200 mL), dried (Na$_2$SO$_4$), filtered and concentrated in vacuo. The crude was then triturated with EtOAc/hexane to afford ethyl 7-chloro-6-(2-ethoxy-2-oxoethyl)-5-methylpyrazolo[1,5-a]pyrimidine-2-carboxylate (22 g, 67.5 mmol, 83% yield) as light yellow solid. $^1$H NMR (500 MHz, CDCl$_3$) δ 7.21 (s, 1H), 4.52 (q, J=7.2 Hz, 2H), 4.24 (q, J=7.2 Hz, 2H), 3.94 (s, 2H), 2.66 (s, 3H), 1.48 (t, J=7.0 Hz, 3H), 1.30 (t, J=7.2 Hz, 3H). LCMS (M+1)=326.2.

Intermediate 3

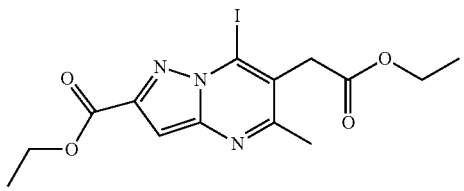 [SMILES: CCOC(=O)Cc1c(C)nc2cc(C(=O)OCC)nn2c1I]

Ethyl 6-(2-ethoxy-2-oxoethyl)-7-iodo-5-methylpyrazolo[1,5-a]pyrimidine-2-carboxylate Ethyl 7-chloro-6-(2-ethoxy-2-oxoethyl)-5-methylpyrazolo[1,5-a]pyrimidine-2-carboxylate (5 g, 15.35 mmol) and sodium iodide (9.20 g, 61.4 mmol) were suspended in acetonitrile (80 mL) and the resulting mixture was heated at 80° C. for 2 h. At this point LCMS indicated completion of reaction and appearance of the desired product. After cooling to rt, the reaction mixture was diluted with ethyl acetate and washed with water and aqueous $Na_2S_2O_3$, dried ($Na_2SO_4$), filtered and concentrated. Then crude product was triturated with ethyl acetate/hexane to afford ethyl 6-(2-ethoxy-2-oxoethyl)-7-iodo-5-methylpyrazolo[1,5-a]pyrimidine-2-carboxylate (5.7 g, 13.66 mmol, 89% yield) as off white solid. $^1$H NMR (500 MHz, CDCl$_3$) δ: 7.32 (s, 1H), 4.51 (d, J=7.0 Hz, 2H), 4.25 (d, J=7.0 Hz, 2H), 4.02 (s, 2H), 2.68 (s, 3H), 1.48 (t, J=7.2 Hz, 3H), 1.31 (t, J=7.2 Hz, 3H). LCMS (M+H)=418.2.

Intermediate 4

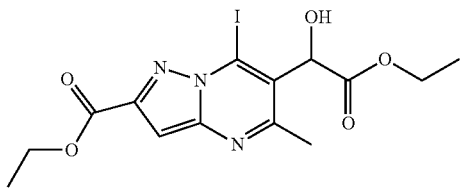 [SMILES: CCOC(=O)c1cc2nc(C)c(C(O)C(=O)OCC)c(I)n2n1]

Ethyl 6-(2-ethoxy-1-hydroxy-2-oxoethyl)-7-iodo-5-methylpyrazolo[1,5-a]pyrimidine-2-carboxylate To a stirred solution of 0.9M KHMDS/THF (39.1 mL, 35.2 mmol) in THF (100 mL) at −78° C. was added a THF (50 mL) solution of ethyl 6-(2-ethoxy-2-oxoethyl)-7-iodo-5-methylpyrazolo[1,5-a]pyrimidine-2-carboxylate (11.3 g, 27.1 mmol) over 5 min. After 30 min, a THF (50 mL) solution of 3-phenyl-2-(phenylsulfonyl)-1,2-oxaziridine (9.20 g, 35.2 mmol) was added to the red reaction mixture and stirred for additional 30 min at −78° C. Then, the resulting orange reaction mixture was quenched with sat. NH$_4$Cl (50 mL), diluted with EtOAc (200 mL), washed with water (100 mL), brine (100 mL), dried (Na$_2$SO$_4$), filtered and concentrated to give solid. This solid was triturated with small amount of ethyl acetate and solids were filtered, washed with hexanes and dried under high vac to afford ethyl 6-(2-ethoxy-1-hydroxy-2-oxoethyl)-7-iodo-5-methylpyrazolo[1,5-a]pyrimidine-2-carboxylate (7.3 g, 16.85 mmol, 62.2% yield) as light yellow solid. $^1$H NMR (500 MHz, CDCl$_3$) δ: 7.33 (s, 1H), 5.75 (d, J=2.1 Hz, 1H), 4.52 (qd, J=7.1, 1.2 Hz, 2H), 4.37-4.30 (m, 2H), 3.57 (d, J=2.4 Hz, 1H), 2.63 (s, 3H), 1.48 (t, J=7.2 Hz, 3H), 1.27 (t, J=7.0 Hz, 3H). LCMS (M+H)=434.1.

Intermediate 5

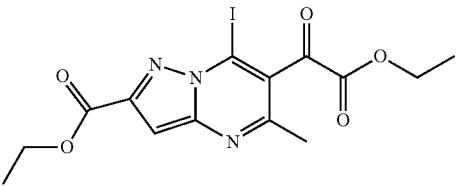 [SMILES: CCOC(=O)C(=O)c1c(C)nc2cc(C(=O)OCC)nn2c1I]

Ethyl 6-(2-ethoxy-2-oxoacetyl)-7-iodo-5-methylpyrazolo[1,5-a]pyrimidine-2-carboxylate To a mixture of ethyl 6-(2-ethoxy-1-hydroxy-2-oxoethyl)-7-iodo-5-methylpyrazolo[1,5-a]pyrimidine-2-carboxylate (3.7 g, 6.41 mmol) in CH$_2$Cl$_2$ (80 mL) was added Dess-Martin Periodinane (2.72 g, 6.41 mmol) and the resulting mixture was stirred at rt for 1 hr. Then diluted with ethyl acetate (500 mL) and washed with sat. NaHCO$_3$ solution (100 mL), dried (Na$_2$SO$_4$), filtered, concentrated and the residue was purified by silica gel chromatography (5-70% EtOAc/hexane) to afford desired ethyl 6-(2-ethoxy-2-oxoacetyl)-7-iodo-5-methylpyrazolo[1,5-a]pyrimidine-2-carboxylate (2.5 g, 5.80 mmol, 91% yield) as off-white solid. $^1$H NMR (400 MHz, CDCl$_3$) δ: 7.36 (s, 1H), 4.50 (dq, J=14.5, 7.1 Hz, 4H), 2.56 (s, 3H), 1.46 (t, J=7.2 Hz, 3H), 1.48 (t, J=7.2 Hz, 3H). LCMS (M+H)=431.87.

Intermediate 6

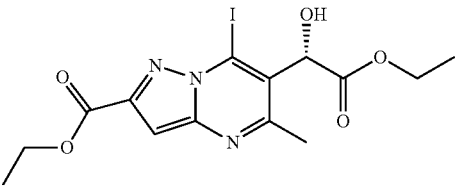 [SMILES: CCOC(=O)c1cc2nc(C)c([C@H](O)C(=O)OCC)c(I)n2n1]

(S)-Ethyl 6-(2-ethoxy-1-hydroxy-2-oxoethyl)-7-iodo-5-methylpyrazolo[1,5-a]pyrimidine-2-carboxylate To a stirred yellow solution of ethyl 6-(2-ethoxy-2-oxoacetyl)-7-iodo-5-methylpyrazolo[1,5-a]pyrimidine-2-carboxylate (6.4 g, 14.84 mmol) in anhydrous toluene (300 mL) was added 1.1M (R)-1-methyl-3,3-diphenylhexahydropyrrolo[1,2-c][1,3,2]oxazaborole/toluene (5.40 mL, 5.94 mmol). The mixture was cooled to −35° C. and a solution of 50% catecholborane/toluene (5.09 mL, 20.78 mmol) was added over 10 min. After 30 min, the reaction mixture was slowly warmed to −15° C. and stirred for additional 2 h, then diluted with EtOAc (600 mL) and sat. Na₂CO₃ (100 mL). The mixture was stirred vigorously for 30 min, and the organic phase washed with sat Na₂CO₃ (2×100 mL), dried (Na₂SO₄), filtered, concentrated and the residue was purified by silica gel chromatography (5-100% EtOAc/hexane) to afford desired (S)-ethyl 6-(2-ethoxy-1-hydroxy-2-oxoethyl)-7-iodo-5-methylpyrazolo[1,5-a]pyrimidine-2-carboxylate (5.3 g, 12.23 mmol, 82% yield) as off-white solid. ¹H NMR (500 MHz, CDCl₃) δ: 7.33 (s, 1H), 5.75 (d, J=2.4 Hz, 1H), 4.52 (qd, J=7.1, 1.1 Hz, 2H), 4.38-4.29 (m, 2H), 3.59 (d, J=2.4 Hz, 1H), 2.63 (s, 3H), 1.48 (t, J=7.2 Hz, 3H), 1.27 (t, J=7.2 Hz, 3H). LCMS (M+H)=434.2.

Intermediate 7

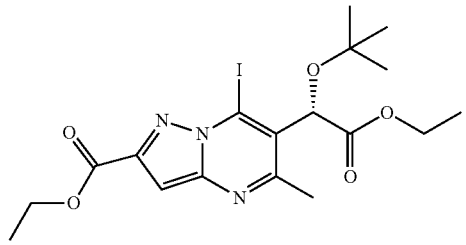 [SMILES: CCOC(=O)c1cc2nc(C)c([C@H](OC(C)(C)C)C(=O)OCC)c(I)n2n1]

(S)-Ethyl 6-(1-(tert-butoxy)-2-ethoxy-2-oxoethyl)-7-iodo-5-methylpyrazolo[1,5-a]pyrimidine-2-carboxylate To a stirred solution of (S)-ethyl 6-(2-ethoxy-1-hydroxy-2-oxoethyl)-7-iodo-5-methylpyrazolo[1,5-a]pyrimidine-2-carboxylate (5.3 g, 12.23 mmol) in CH₂Cl₂ (150 mL) and t-butyl acetate (105 mL) was added perchloric acid (3.15 mL, 36.7 mmol) at rt and sealed the reaction flask. After 3 h, the reaction mixture was diluted with CH₂Cl₂ (100 mL), carefully quenched with sat. NaHCO₃ (50 mL), organic layer separated and washed with brine (100 mL), dried (Na₂SO₄), filtered and concentrated to give yellow liquid. This was purified by flash column chromatograpgy on silica gel column using (10-50% EtOAc/Hex as eluant) to afford the desired (S)-ethyl 6-(1-(tert-butoxy)-2-ethoxy-2-oxoethyl)-7-iodo-5-methylpyrazolo[1,5-a]pyrimidine-2-carboxylate (4.5 g, 8.28 mmol, 67.7% yield) as viscous oil. 700 mg of starting material was also recovered. ¹H NMR (500 MHz, CDCl₃) δ: 7.31 (s, 1H), 5.56 (s, 1H), 4.51 (q, J=7.1 Hz, 2H), 4.26-4.16 (m, 2H), 2.71 (s, 3H), 1.48 (t, J=7.2 Hz, 3H), 1.30 (s, 9H), 1.23 (t, J=7.0 Hz, 3H). LCMS (M+H) =490.0.

Intermediate 8

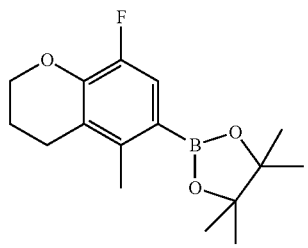 [SMILES: Cc1c(B2OC(C)(C)C(C)(C)O2)cc(F)c2c1CCCO2]

2-(8-Fluoro-5-methylchroman-6-yl)-4,4,5,5-tetramethyl-1,3,2 dioxaborolane

The title compound was prepared by the known procedure as described in the reference WO 2009062285.

Intermediate 9

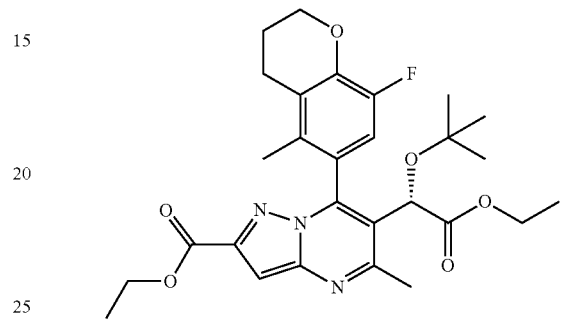

6-((S)-1-(tert-Butoxy)-2-ethoxy-2-oxoethyl)-7-(8-fluoro-5-methylchroman-6-yl)-5-methylpyrazolo[1,5-a]pyrimidine-2-carboxylate A mixture of (S)-ethyl 6-(1-(tert-butoxy)-2-ethoxy-2-oxoethyl)-7-iodo-5-methylpyrazolo[1,5-a]pyrimidine-2-carboxylate (4.5 g, 9.20 mmol), 2-(8-fluoro-5-methylchroman-6-yl)-4,4,5,5-tetramethyl-1,3,2-dioxaborolane (3.22 g, 11.04 mmol) and 2N Na₂CO₃ (9.20 mL, 18.39 mmol) in DMF (100 mL) was degassed and flushed with N₂ for 30 min. Tetrakis(triphenylphosphine)palladium(0) (0.744 g, 0.644 mmol) was then added and the reaction was flushed with N₂ for another 15 min. The mixture was then heated at 100° C. for 16 h. At this point LCMS indicated completion of reaction and appearance of desired product. After cooling to rt, water was added (50 mL) and the mixture was extracted with ether (2×200 mL). The organic phase was washed with brine (100 mL), dried (Na₂SO₄), filtered and concentrated in vacuo. The residue was then purified by silica gel chromatography (5-60% EtOAc/hexane) to afford ethyl 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylate (4 g, 7.58 mmol, 82% yield) as mixture of atrope isomers (approx 10% of minor atrope isomer was present). 1H NMR (500 MHz, CDCl₃) δ 7.10 (s, 1H), 6.87 (d, J=10.7 Hz, 1H), 5.00 (s, 1H), 4.41 (qd, J=7.1, 3.1 Hz, 2H), 4.35 (dd, J=5.2, 4.0 Hz, 2H), 4.14 (q, J=7.2 Hz, 2H), 2.80 (s, 3H), 2.79-2.73 (m, 2H), 2.23-2.15 (m, 2H), 1.82 (s, 3H), 1.41 (t, J=7.2 Hz, 3H), 1.22-1.19 (m, 4H), 1.18 (s, 9H). LCMS (M+H)=528.4.

Intermediate 10

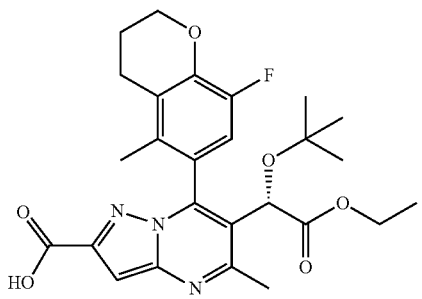 [SMILES: CCOC(=O)[C@@H](OC(C)(C)C)c1c(C)nc2cc(C(=O)O)nn2c1-c1cc(F)c2c(c1C)CCCO2]

6-((S)-1-(tert-Butoxy)-2-ethoxy-2-oxoethyl)-7-(8-fluoro-5-methylchroman-6-yl)-5-methylpyrazolo[1,5-a]pyrimidine-2-carboxylic acid To a solution of ethyl 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylate (4 g, 6.07 mmol) in THF (40 mL) was added 1N NaOH (6.07 mL, 6.07 mmol) and the resulting mixture was stirred at rt for 16 h. At this point the LCMS indicated about 70% conversion, so additional 1N NaOH (2.5 mL, 2.5 mmol) was added and the mixture was stirred for another 2 h. At this point LCMS indicated progression of reaction (~90% conversion) along with small amount of di-acid. Water (20 mL) was then added to the reaction mixture and it was acidified with 1N HCl (10 mL). This aqueous solution was extracted with ether (2×100 mL), washed with brine (50 mL), dried ($Na_2SO_4$), filtered and concentrated in vacuo to afford 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylic acid (2.7 g, 5.41 mmol, 89% yield) as off-white solid. 1H NMR (500 MHz, $CDCl_3$) δ 7.21 (s, 1H), 6.85 (d, J=10.7 Hz, 1H), 5.00 (s, 1H), 4.36 (t, J=4.4 Hz, 2H), 4.19-4.12 (m, 2H), 2.81 (s, 3H), 2.80-2.74 (m, 2H), 2.20 (dd, J=6.3, 4.1 Hz, 2H), 1.83 (s, 3H), 1.24-1.20 (m, 3H), 1.18 (s, 9H). LCMS (M+H)=500.4.

Intermediate 11

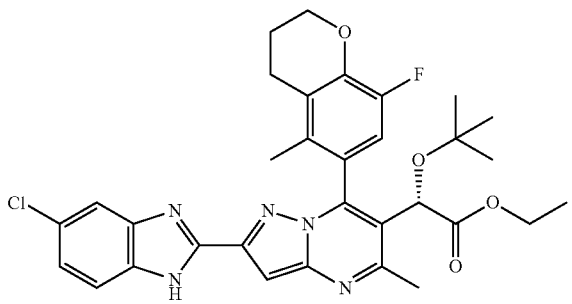 [SMILES: CCOC(=O)[C@@H](OC(C)(C)C)c1c(C)nc2cc(-c3nc4cc(Cl)ccc4[nH]3)nn2c1-c1cc(F)c2c(c1C)CCCO2]

(2S)-Ethyl 2-(tert-butoxy)-2-(2-(5-chloro-1H-benzo[d]imidazol-2-yl)-7-(8-fluoro-5-methylchroman-6-yl)-5-methylpyrazolo[1,5-a]pyrimidin-6-yl)acetate To a mixture of 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylic acid (140 mg, 0.280 mmol) and 4-chlorobenzene-1,2-diamine (59.9 mg, 0.420 mmol) in DMF (3 mL) was added DIEA (0.245 mL, 1.401 mmol) followed by HATU (320 mg, 0.841 mmol) and DMAP (3.42 mg, 0.028 mmol) and the resulting mixture was stirred at room temp for 16 h. Water was then added and the mixture was extracted with ethyl acetate (50 mL), washed with brine (25 mL), dried ($Na_2SO_4$), filtered and concentrated. The residue was then suspended in AcOH (3 mL) and the mixture was heated at 60° C. for 1 h. Mixture was then concentrated and residue was dissolved in ethyl acetate (20 mL) and washed with sat. $NaHCO_3$ and brine (10 mL each), dried, filtered and concentrated. The crude was then purified by silica gel chromatography (5-60% EtOAc/hexane) to afford (2S)-ethyl 2-(tert-butoxy)-2-(2-(5-chloro-1H-benzo[d]imidazol-2-yl)-7-(8-fluoro-5-methylchroman-6-yl)-5-methylpyrazolo[1,5-a]pyrimidin-6-yl)acetate (64 mg, 0.106 mmol, 38% yield) as a white solid. $^1$H NMR (500 MHz, $CDCl_3$) δ 10.71 (br. s., 1H), 7.83-7.70 (m, 1H), 7.42 (s, 1H), 7.24-7.15 (m, 2H), 6.88 (d, J=10.4 Hz, 1H), 4.92 (s, 1H), 4.36-4.29 (m, 2H), 4.18 (q, J=7.2 Hz, 2H), 2.82 (s, 3H), 2.64-2.53 (m, 1H), 2.34-2.28 (m, 1H), 2.16-2.05 (m, 2H), 1.77 (s, 3H), 1.24 (t, J=7.2 Hz, 3H), 1.14 (s, 9H). LCMS (M+H)=607.49.

Example 1

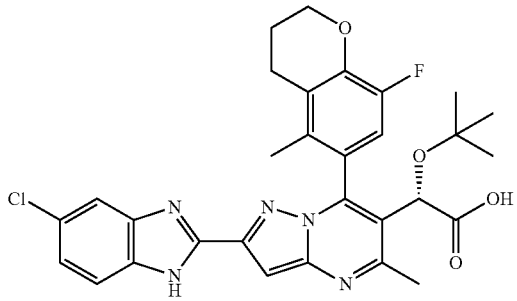 [SMILES: Cc1nc2cc(-c3nc4cc(Cl)ccc4[nH]3)nn2c(-c2cc(F)c3c(c2C)CCCO3)c1[C@H](OC(C)(C)C)C(=O)O]

(2S)-2-(tert-Butoxy)-2-(2-(5-chloro-1H-benzo[d]imidazol-2-yl)-7-(8-fluoro-5-methylchroman-6-yl)-5-methylpyrazolo[1,5-a]pyrimidin-6-yl)acetic acid A solution of (2S)-ethyl 2-(tert-butoxy)-2-(2-(5-chloro-1H-benzo[d]imidazol-2-yl)-7-(8-fluoro-5-methylchroman-6-yl)-5-methylpyrazolo[1,5-a]pyrimidin-6-yl)acetate (25 mg, 0.041 mmol) and 1M NaOH (0.165 mL, 0.165 mmol) in MeOH (1 mL) was heated at 60° C. for 16 h. Then, the reaction mixture was cooled and purified by prep HPLC to afford (2S)-2-(tert-butoxy)-2-(2-(5-chloro-1H-benzo[d]imidazol-2-yl)-7-(8-fluoro-5-methylchroman-6-yl)-5-methylpyrazolo[1,5-a]pyrimidin-6-yl)acetic acid (13.7 mg, 0.023 mmol, 54.6% yield) as white solid. $^1$H NMR (500 MHz, METHANOL-$d_4$) δ 7.59-7.52 (m, 2H), 7.30-7.27 (m, 1H), 7.26 (d, J=2.1 Hz, 1H), 7.03 (d, J=11.0 Hz, 1H), 5.00 (s, 1H), 4.33 (t, J=5.0 Hz, 2H), 2.84 (s, 3H), 2.81 (d, J=6.7 Hz, 2H), 2.24-2.10 (m, 2H), 1.93 (s, 3H), 1.20 (s, 9H). LCMS (M+H)=578.3.

Example 2 and 3

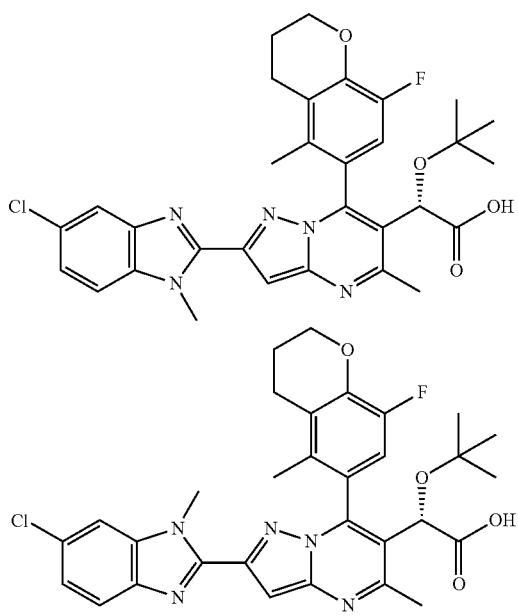

(2S)-2-(tert-Butoxy)-2-(2-(5-chloro-1-methyl-1H-benzo[d]imidazol-2-yl)-7-(8-fluoro-5-methylchroman-6-yl)-5-methylpyrazolo[1,5-a]pyrimidin-6-yl)acetic acid and (2S)-2-(tert-butoxy)-2-(2-(6-chloro-1-methyl-1H-benzo[d]imidazol-2-yl)-7-(8-fluoro-5-methylchroman-6-yl)-5-methylpyrazolo[1,5-a]pyrimidin-6-yl)acetic acid To a solution of (2S)-ethyl 2-(tert-butoxy)-2-(2-(5-chloro-1H-benzo[d]imidazol-2-yl)-7-(8-fluoro-5-methylchroman-6-yl)-5-methylpyrazolo[1,5-a]pyrimidin-6-yl)acetate (40 mg, 0.066 mmol) in DMF (2 mL) was added NaH (3.96 mg, 0.099 mmol) and the resulting mixture was stirred at room temp for 10 min. MeI (6.19 µl, 0.099 mmol) was then added and the mixture was stirred at room temp for 16 h. At this point LCMS indicates completion of reaction and appearance of desired product. Water was then added and the mixture was extracted with ethyl acetate, dried (Na$_2$SO$_4$), filtered and concentrated. Crude was then treated with 1M NaOH (0.264 mL, 0.264 mmol) in MeOH (1.000 mL) and the mixture was heated at 60° C. for 16 h. Mixture was then cooed and purified by prep HPLC to afford two regio isomers.

Example 2

(2S)-2-(tert-Butoxy)-2-(2-(5-chloro-1-methyl-1H-benzo[d]imidazol-2-yl)-7-(8-fluoro-5-methylchroman-6-yl)-5-methylpyrazolo[1,5-a]pyrimidin-6-yl)acetic acid (7 mg, 0.011 mmol, 17.02% yield). $^1$H NMR (500 MHz, METHANOL-d$_4$) δ 7.69 (d, J=1.8 Hz, 1H), 7.54 (d, J=8.5 Hz, 1H), 7.34 (dd, J=8.7, 2.0 Hz, 1H), 7.25 (s, 1H), 7.02 (d, J=11.0 Hz, 1H), 4.99 (s, 1H), 4.31 (t, J=5.2 Hz, 2H), 4.00 (s, 3H), 2.88 (s, 3H), 2.85-2.76 (m, 2H), 2.17-2.12 (m, 2H), 1.99 (s, 3H), 1.20 (s, 9H). LCMS (M+H)=592.3.

Example 3

(2S)-2-(tert-Butoxy)-2-(2-(6-chloro-1-methyl-1H-benzo[d]imidazol-2-yl)-7-(8-fluoro-5-methylchroman-6-yl)-5-methylpyrazolo[1,5-a]pyrimidin-6-yl)acetic acid (9 mg, 0.014 mmol, 21.88% yield). $^1$H NMR (500 MHz, METHANOL-d$_4$) δ 7.66 (d, J=8.9 Hz, 1H), 7.63 (d, J=1.8 Hz, 1H), 7.30 (dd, J=8.5, 1.8 Hz, 1H), 7.23 (s, 1H), 7.01 (d, J=11.0 Hz, 1H), 4.94 (s, 1H), 4.30 (t, J=5.2 Hz, 2H), 3.98 (s, 3H), 2.89 (s, 3H), 2.85-2.77 (m, 2H), 2.20-2.12 (m, 2H), 2.01 (s, 3H), 1.19 (s, 9H). LCMS (M+H)=592.3.

Example 4

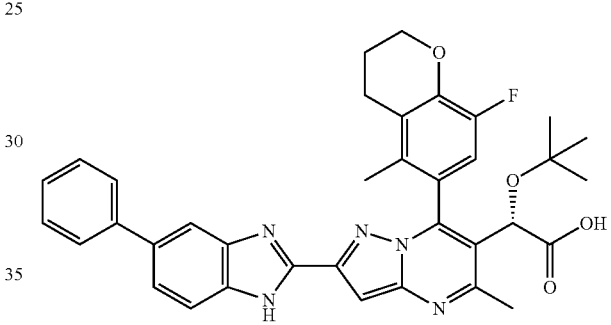

(2S)-2-(tert-Butoxy)-2-(7-(8-fluoro-5-methylchroman-6-yl)-5-methyl-2-(5-phenyl-1H-benzo[d]imidazol-2-yl)pyrazolo[1,5-a]pyrimidin-6-yl)acetic acid To a mixture of (2S)-2-(tert-butoxy)-2-(2-(5-chloro-1H-benzo[d]imidazol-2-yl)-7-(8-fluoro-5-methylchroman-6-yl)-5-methylpyrazolo[1,5-a]pyrimidin-6-yl)acetic acid (10 mg, 0.017 mmol), 4,4,5,5-tetramethyl-2-phenyl-1,3,2-dioxaborolane (7.06 mg, 0.035 mmol) and 2.0M K$_3$PO$_4$ (0.017 mL, 0.035 mmol) in DMF (1 mL) was added dicyclohexyl (2',6'-dimethoxy-[1,1'-biphenyl]-2-yl)phosphine (10.65 mg, 0.026 mmol) followed by palladium(II) acetate (3.88 mg, 0.017 mmol) and the mixture was heated at 130° C. in microwave for 16 min. Mixture was then filtered and purified by prep HPLC to afford (2S)-2-(tert-butoxy)-2-(7-(8-fluoro-5-methylchroman-6-yl)-5-methyl-2-(5-phenyl-1H-benzo[d]imidazol-2-yl)pyrazolo[1,5-a]pyrimidin-6-yl)acetic acid (6 mg, 9.20 µmol, 53.2% yield). $^1$H NMR (500 MHz, DMSO-d$_6$) δ 12.83 (s, J=1H), 7.97 (s, 1H), 7.79-7.66 (m, 3H), 7.55-7.45 (m, 3H), 7.36 (t, J=7.2 Hz, 1H), 7.21 (s, 1H), 7.12 (d, J=11.3 Hz, 1H), 4.62 (br. s., 1H), 4.29 (t, J=5.8 Hz, 2H), 2.79-2.76 (m, 2H), 2.75-2.72 (m, 5H), 2.02-2.09 (m, 2H), 1.90 (s, 3H), 1.07 (s, 9H). LCMS (M+H)=620.4

Intermediate 12

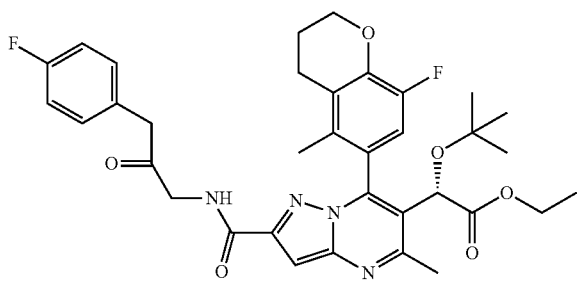 [SMILES: CCOC(=O)[C@@H](OC(C)(C)C)c1c(C)nc2cc(C(=O)NCC(=O)Cc3ccc(F)cc3)nn2c1-c1cc(F)c2c(c1C)CCCO2]

(2S)-Ethyl 2-(tert-butoxy)-2-(7-(8-fluoro-5-methyl-chroman-6-yl)-2-((3-(4-fluorophenyl)-2-oxopropyl)carbamoyl)-5-methylpyrazolo[1,5-a]pyrimidin-6-yl)acetate To a solution of 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylic acid (150 mg, 0.300 mmol) in CH$_2$Cl$_2$ (2 mL) was added oxalyl chloride (0.039 mL, 0.450 mmol) 1 drop of DMF was then added and the mixture was stirred at room temp for 1 h. The crude acid chloride was then added to a pre-stirred solution of 1-amino-3-(4-fluorophenyl)propan-2-one, HCl (122 mg, 0.601 mmol, Synthetic Communications 1972, 237-242) and DIEA (0.315 mL, 1.802 mmol) in CH$_2$Cl$_2$ (2.0 mL) and the resulting solution was stirred at room temperature for 2 h. Water was then added and the mixture was extracted with dichloromethane, dried (Na$_2$SO$_4$), filtered and concentrated. The crude was then purified by flash column chromatograpgy on silica gel column using (50-100% EtOAc/Hexane as eluant) to afford (2S)-ethyl 2-(tert-butoxy)-2-(7-(8-fluoro-5-methylchroman-6-yl)-2-((3-(4-fluorophenyl)-2-oxopropyl)carbamoyl)-5-methylpyrazolo[1,5-a]pyrimidin-6-yl)acetate (115 mg, 0.177 mmol, 59.0% yield) as light yellow solid. $^1$H NMR (500 MHz, CDCl$_3$) δ 7.40 (t, J=5.0 Hz, 1H), 7.23-7.18 (m, 2H), 7.14 (s, 1H), 7.07-7.02 (m, 2H), 6.85 (d, J=10.4 Hz, 1H), 4.98 (s, 1H), 4.46-4.35 (m, 3H), 4.30-4.23 (m, 1H), 4.15 (q, J=7.1 Hz, 2H), 3.77 (s, 2H), 2.84-2.75 (m, 2H), 2.79 (s, 3H), 2.20 (dd, J=6.3, 3.8 Hz, 2H), 1.84 (s, 3H), 1.23-1.19 (m, 3H), 1.18 (s, 9H). LCMS (M+H)=649.5.

Example 5

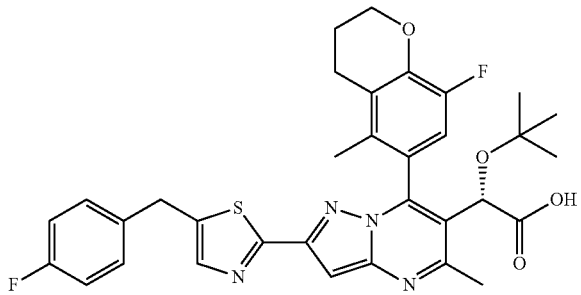

(2S)-2-(tert-Butoxy)-2-(7-(8-fluoro-5-methylchroman-6-yl)-2-(5-(4-fluorobenzyl)thiazol-2-yl)-5-methylpyrazolo[1,5-a]pyrimidin-6-yl)acetic acid To a solution of (2S)-ethyl 2-(tert-butoxy)-2-(7-(8-fluoro-5-methylchroman-6-yl)-2-((3-(4-fluorophenyl)-2-oxopropyl)carbamoyl)-5-methylpyrazolo[1,5-a]pyrimidin-6-yl)acetate (20 mg, 0.031 mmol) in toluene was added Lawesson's Reagent (37.4 mg, 0.092 mmol) and stirr for 15 min at rt, 30 min at 60° C. and 5 h at 100° C. Then, the resulting clear yellow mixture was cooled, concentrated and purified by prep HPLC to afford desired ester as light yellow solid. $^1$H NMR (500 MHz, CDCl3) δ 7.63 (s, 1H), 7.21 (dd, J=8.4, 5.3 Hz, 2H), 7.11 (s, 1H), 7.02 (t, J=8.7 Hz, 2H), 6.87 (d, J=10.4 Hz, 1H), 4.97 (s, 1H), 4.41-4.31 (m, 2H), 4.15 (s, 2H), 4.16-4.10 (m, 2H), 2.79 (s, 3H), 2.81-2.73 (m, 2H), 2.19 (dd, J=6.3, 3.5 Hz, 2H), 1.84 (s, 3H), 1.20 (t, J=7.2 Hz, 3H), 1.18 (s, 9H). LCMS (M+H)=647.5.

Ester was then treated with 1M NaOH (0.092 mL, 0.092 mmol) in MeOH (1.050 mL) at 60° C. for 5 h. Mixture was then cooled, concentrated and purified by prep HPLC to afford (2S)-2-(tert-butoxy)-2-(7-(8-fluoro-5-methylchroman-6-yl)-2-(5-(4-fluorobenzyl)thiazol-2-yl)-5-methylpyrazolo[1,5-a]pyrimidin-6-yl)acetic acid (7 mg, 10.75 μmol, 34.9% yield) as white solid. $^1$H NMR (500 MHz, CDCl$_3$) δ 7.65 (s, 1H), 7.21 (dd, J=8.5, 5.5 Hz, 2H), 7.13 (s, 1H), 7.05-6.99 (m, 2H), 6.90 (d, J=10.4 Hz, 1H), 5.06 (s, 1H), 4.39-4.29 (m, 2H), 4.15 (s, 2H), 2.72-2.76 (m, 5H), 2.17 (d, J=4.3 Hz, 2H), 1.89 (s, 3H), 1.21 (s, 9H). LCMS (M+H)=619.5.

Example 6

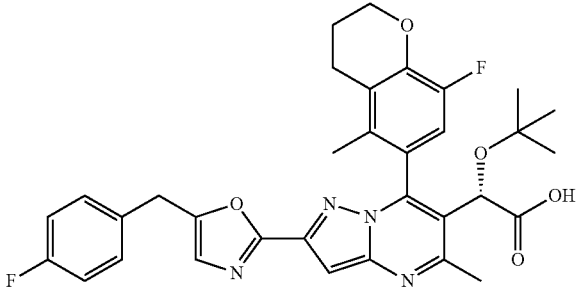 [SMILES: Cc1nc2cc(-c3ncc(Cc4ccc(F)cc4)s3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-2-(5-(4-fluorobenzyl)oxazol-2-yl)-5-methylpyrazolo[1,5-a]pyrimidin-6-yl)acetic acid To a stirred solution of (2S)-ethyl 2-(tert-butoxy)-2-(7-(8-fluoro-5-methylchroman-6-yl)-2-((3-(4-fluorophenyl)-2-oxopropyl)carbamoyl)-5-methylpyrazolo[1,5-a]pyrimidin-6-yl)acetate (50 mg, 0.077 mmol), Ph$_3$P (40.4 mg, 0.154 mmol) and TEA (0.054 mL, 0.385 mmol) in acetonitrile (1.5 mL) was added CCl$_4$ (0.015 mL, 0.154 mmol) and the mixture was stirred at room temp for 5 h. and then 40° C. for 16 h. Mixture was then cooled, concentrated and purified by prep HPLC to afford desired ester as off-white solid. $^1$H NMR (500 MHz, CDCl$_3$) δ 7.25 (dd, J=8.4, 5.3 Hz, 2H), 7.09 (s, 1H), 7.06-7.01 (m, 2H), 6.89 (d, J=10.4 Hz, 1H), 6.83 (s, 1H), 4.99 (s, 1H), 4.35 (dd, J=5.8, 4.6 Hz, 2H), 4.15 (q, J=7.1 Hz, 2H), 4.07 (s, 2H), 2.80 (s, 3H), 2.79-2.73 (m, 2H), 2.22-2.15 (m, 2H), 1.85 (s, 3H), 1.21 (t, J=7.2 Hz, 3H), 1.18 (s, 9H). LCMS (M+H)=631.5.

Ester was then treated with 1M NaOH (0.231 mL, 0.231 mmol) in MeOH (0.900 mL) at 60° C. for 5 h. Mixture was then cooled, concentrated and purified by prep HPLC to afford (2S)-2-(tert-butoxy)-2-(7-(8-fluoro-5-methylchroman-6-yl)-2-(5-(4-fluorobenzyl)oxazol-2-yl)-5-methylpyrazolo[1,5-a]pyrimidin-6-yl)acetic acid (5 mg, 7.88 µmol, 10.23% yield) as off-white solid. $^1$H NMR (500 MHz, CDCl$_3$) δ 7.27-7.23 (m, 2H), 7.10 (s, 1H), 7.06-7.00 (m, 2H), 6.92 (d, J=10.7 Hz, 1H), 6.84 (s, 1H), 5.08 (s, 1H), 4.37-4.30 (m, 2H), 4.06 (s, 2H), 2.76 (s, 3H), 2.76-2.71 (m, 2H), 2.21-2.13 (m, 2H), 1.91 (s, 3H), 1.21 (s, 9H). LCMS (M+H)=603.5.

Example 7

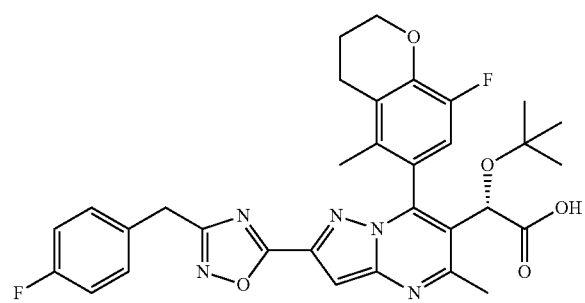 [SMILES: Cc1nc2cc(-c3nc(Cc4ccc(F)cc4)no3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-2-(3-(4-fluorobenzyl)-1,2,4-oxadiazol-5-yl)-5-methylpyrazolo[1,5-a]pyrimidin-6-yl)acetic acid To a solution of 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylic acid (50 mg, 0.100 mmol) in CH$_2$Cl$_2$ (1 mL) was added oxalyl chloride (0.014 mL, 0.160 mmol) 1 drop of DMF was then added and the mixture was stirred at room temp for 1 h. This acid chloride was then added dropwise to a stirred solution of 2-(4-fluorophenyl)-N-hydroxyacetimidamide (33.7 mg, 0.200 mmol) and DIEA (0.070 mL, 0.400 mmol) in CH$_2$Cl$_2$ (1 mL) and the mixture was stirred at room temp for 1 h. Mixture was then concentrated and heated in dioxane (1.000 mL) at 90° C. for 14 h. At this point LCMS indicates desired product as major. Mixture was then concentrated and purified by prep HPLC to afford desired ester. $^1$H NMR (500 MHz, CDCl$_3$) δ 7.34 (dd, J=8.7, 5.3 Hz, 2H), 7.25 (s, 1H), 7.05-7.00 (m, 2H), 6.88 (d, J=10.4 Hz, 1H), 5.01 (s, 1H), 4.39-4.34 (m, 2H), 4.18-4.12 (m, 4H), 2.82 (s, 3H), 2.80-2.73 (m, 2H), 2.25-2.18 (m, 2H), 1.84 (s, 3H), 1.23-1.20 (m, 3H), 1.19 (s, 9H). LCMS (M+H)=632.5.

Ester was then treated with 1M NaOH (0.300 mL, 0.300 mmol) in MeOH (1.0 mL) at 60° C. for 5 h. Mixture was then cooled, concentrated and purified by prep HPLC to afford (2S)-2-(tert-butoxy)-2-(7-(8-fluoro-5-methylchroman-6-yl)-2-(3-(4-fluorobenzyl)-1,2,4-oxadiazol-5-yl)-5-methylpyrazolo[1,5-a]pyrimidin-6-yl)acetic acid (5 mg, 7.87 µmol, 7.86% yield) as off-white solid. $^1$H NMR (500 MHz, CDCl$_3$) δ 7.36-7.32 (m, 2H), 7.28 (br. s., 1H), 7.05-7.00 (m, 2H), 6.91 (d, J=10.4 Hz, 1H), 5.11 (s, 1H), 4.40-4.28 (m, 2H), 4.15 (s, 2H), 2.78 (s, 3H), 2.75 (t, J=6.9 Hz, 2H), 2.18 (dd, J=10.8, 4.1 Hz, 2H), 1.90 (s, 3H), 1.23 (s, 10H). LCMS (M+H)=604.5.

Intermediate 13

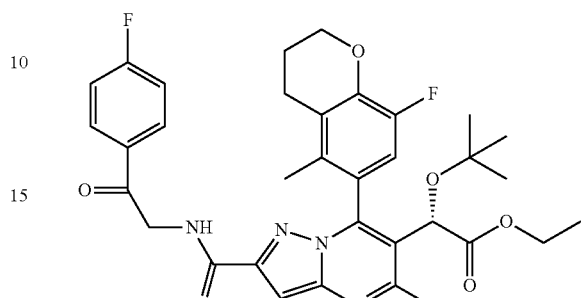

(2S)-Ethyl 2-(tert-Butoxy)-2-(7-(8-fluoro-5-methylchroman-6-yl)-2-((2-(4-fluorophenyl)-2-oxoethyl)carbamoyl)-5-methylpyrazolo[1,5-a]pyrimidin-6-yl)acetate To a solution of 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylic acid (150 mg, 0.300 mmol) in CH$_2$Cl$_2$ (2 mL) was added oxalyl chloride (0.039 mL, 0.450 mmol) 1 drop of DMF was then added and the mixture was stirred at room temp for 1 h. The crude acid chloride was then added to a pre-stirred solution of 2-amino-1-(4-fluorophenyl)ethanone, HCl (114 mg, 0.601 mmol) and DIEA (0.315 mL, 1.802 mmol) in CH$_2$Cl$_2$ (2.000 mL) and the resulting solution was stirred at room temperature for 2 h. Water was then added and the mixture was extracted with dichloromethane, dried (Na$_2$SO$_4$), filtered and concentrated. The crude was then purified by flash column chromatograpgy on silica gel column using (50-100% EtOAc/Hex as eluant) to afford (2S)-ethyl 2-(tert-butoxy)-2-(7-(8-fluoro-5-methylchroman-6-yl)-2-((2-(4-fluorophenyl)-2-oxoethyl)carbamoyl)-5-methylpyrazolo[1,5-a]pyrimidin-6-yl)acetate (20 mg, 0.032 mmol, 10.49% yield) as light yellow solid. $^1$H NMR (500 MHz, CDCl$_3$) δ 8.14-7.98 (m, 2H), 7.72 (br. s., 1H), 7.24-7.13 (m, 3H), 6.90 (s, 1H), 5.02 (s, 1H), 4.97 (dd, J=19.5, 4.7 Hz, 1H), 4.87-4.76 (m, 1H), 4.39 (br. s., 2H), 4.16 (q, J=6.8 Hz, 2H), 2.81 (s, 3H), 2.24 (d, J=5.0 Hz, 2H), 1.88 (s, 3H), 1.25-1.21 (m, 3H), 1.20 (s, 9H). LCMS (M+H)=635.5.

Example 8

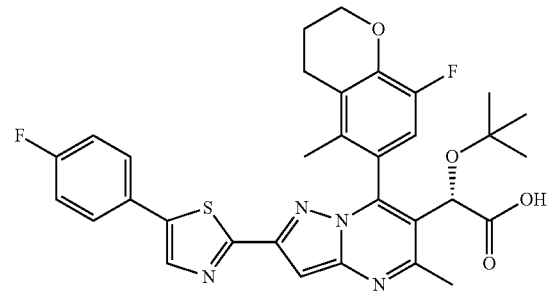 [SMILES: Cc1nc2cc(-c3ncc(-c4ccc(F)cc4)s3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-2-(5-(4-fluorophenyl)thiazol-2-yl)-5-methylpyrazolo[1,5-a]pyrimidin-6-yl)acetic acid To a solution of (2S)-ethyl 2-(tert-butoxy)-2-(7-(8-fluoro-5-methylchroman-6-yl)-2-((2-(4-fluorophenyl)-2-oxoethyl)carbamoyl)-5-methylpyrazolo[1,5-a]pyrimidin-6-yl)acetate (47 mg, 0.074 mmol) in toluene was added Lawesson's Reagent (90 mg, 0.222 mmol) and stirr for 15 min at rt, 30 min at 60° C. and 5 h at 100° C. Then, the resulting clear yellow mixture was cooled, concentrated and purified by prep HPLC to afford desired ester as light yellow solid. $^1$H NMR (500 MHz CDCl$_3$) δ 8.00 (s, 1H), 7.58 (dd, J=8.4, 5.1 Hz, 2H), 7.17 (s, 1H), 7.12 (t, J=8.5 Hz, 2H), 6.92 (d, J=10.7 Hz, 1H), 5.02 (s, 1H), 4.43-4.34 (m, 2H), 4.16 (q, J=7.0 Hz, 2H), 2.81 (s, 3H), 2.80-2.77 (m, 2H), 2.22 (br. s., 2H), 1.88 (s, 3H), 1.24-1.21 (m, 3H), 1.20 (s, 9H). LCMS (M+H)=633.5

Ester was then treated with 1M NaOH (0.222 mL, 0.222 mmol) in MeOH (1.050 mL) at 60° C. for 5 h. Mixture was then cooled, concentrated and purified by prep HPLC to afford (2S)-2-(tert-butoxy)-2-(7-(8-fluoro-5-methylchroman-6-yl)-2-(5-(4-fluorophenyl)thiazol-2-yl)-5-methylpyrazolo[1,5-a]pyrimidin-6-yl)acetic acid (4 mg, 6.28 µmol, 8.49% yield) as white solid. $^1$H NMR (500 MHz, CDCl$_3$) δ 8.01 (s, 1H), 7.62-7.55 (m, 2H), 7.20 (s, 1H), 7.15-7.10 (m, 2H), 6.95 (d, J=10.7 Hz, 1H), 5.13 (s, 1H), 4.42-4.31 (m, 2H), 2.82-2.77 (m, 2H), 2.77 (s, 3H), 2.25-2.16 (m, 2H), 1.95 (s, 3H), 1.25 (s, 9H). LCMS (M+H)=605.5.

Intermediate 14

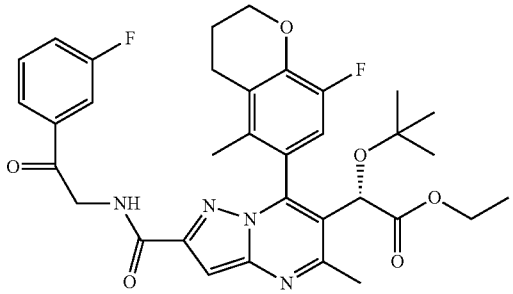 [SMILES: CCOC(=O)[C@@H](OC(C)(C)C)c1c(C)nc2cc(C(=O)NCC(=O)c3cccc(F)c3)nn2c1-c1cc(F)c2c(c1C)CCCO2]

(2S)-Ethyl 2-(tert-Butoxy)-2-(7-(8-fluoro-5-methylchroman-6-yl)-2-((2-(3-fluorophenyl)-2-oxoethyl)carbamoyl)-5-methylpyrazolo[1,5-a]pyrimidin-6-yl)acetate Prepared according to the procedure described for Intermediate XX. $^1$H NMR (500 MHz, CDCl$_3$) δ 7.81 (d, J=7.7 Hz, 1H), 7.74-7.67 (m, 2H), 7.58-7.48 (m, 1H), 7.41-7.32 (m, 1H), 7.18 (s, 1H), 6.90 (d, J=10.6 Hz, 1H), 5.03 (s, 1H), 4.99 (dd, J=19.7, 5.4 Hz, 1H), 4.87-4.77 (m, 2H), 4.46-4.33 (m, 2H), 4.16 (q, J=7.1 Hz, 2H), 2.93-2.83 (m, 1H), 2.83 (s, 3H), 2.29-2.17 (m, 2H), 1.24-1.21 (m, 3H), 1.20 (s, 9H). LCMS (M+H)=635.6.

Example 9

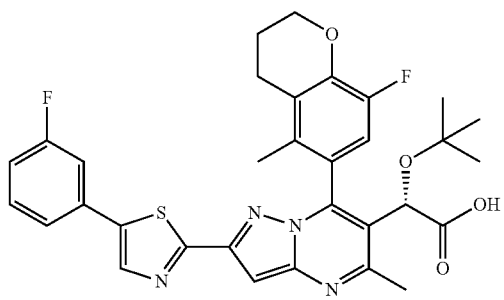 [SMILES: Cc1nc2cc(-c3ncc(-c4cccc(F)c4)s3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-2-(5-(3-fluorophenyl)thiazol-2-yl)-5-methylpyrazolo[1,5-a]pyrimidin-6-yl)acetic acid Prepared according to the procedure for Example 8. $^1$H NMR (500 MHz, CDCl$_3$) δ 8.08 (s, 1H), 7.41-7.37 (m, 2H), 7.34-7.30 (m, 1H), 7.20 (s, 1H), 7.10-7.03 (m, 1H), 6.94 (d, J=10.6 Hz, 1H), 5.10 (s, 1H), 4.44-4.32 (m, 2H), 2.84-2.79 (m, 2H), 2.78 (s, 3H), 2.26-2.16 (m, 2H), 1.93 (s, 3H), 1.23 (s, 9H). LCMS (M+H)=605.5.

Intermediate 15

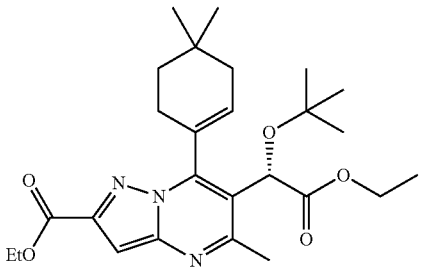 [SMILES: CCOC(=O)c1cc2nc(C)c([C@H](OC(C)(C)C)C(=O)OCC)c(C3=CCC(C)(C)CC3)n2n1]

(S)-Ethyl 6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylate A mixture of (S)-ethyl 6-(1-(tert-butoxy)-2-ethoxy-2-oxoethyl)-7-iodo-5-methylpyrazolo[1,5-a]pyrimidine-2-carboxylate (300 mg, 0.613 mmol), (4,4-dimethylcyclohex-1-en-1-yl)boronic acid (113 mg, 0.736 mmol) and 2M Na$_2$CO$_3$ (0.613 mL, 1.226 mmol) in DMF (6 mL) was degassed for 15 min. tetrakis(triphenylphosphine)palladium(0) (49.6 mg, 0.043 mmol) was then added and the degassing was continue for another 5 min. The mixture was then heated at 100° C. for 2 h. At this point LCMS indicates completion of reaction and appearance of desired product. After cooling to room temp, water was added (10 mL) and the mixture was extracted with ether (2×50 mL), washed with brine (25 mL), dried (Na$_2$SO$_4$), filtered and concentrated. the crude was then purified by biotage (5-30% EtOAc/hexane) to afford (S)-ethyl 6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylate (185 mg, 0.392 mmol, 64.0% yield) as off-white solid (mixture of atrope iaomers). $^1$H NMR (500

MHz, CDCl$_3$) δ 7.05 (s, 1H), 6.25 (br. s., 0.7H), 5.93 (s, 0.3H), 5.55 (s, 0.7H), 5.48 (s, 0.3H), 4.50-4.36 (m, 2H), 4.27-4.17 (m, 2H), 3.36-3.23 (m, 1H), 2.77 (s, 1H), 2.69 (s, 2H), 2.30-2.16 (m, 2H), 2.09-1.92 (m, 1H), 1.80-1.69 (m, 1H), 1.60 (s, 6H), 1.59-1.50 (m, 1H), 1.44 (t, J=7.2 Hz, 3H), 1.26-1.20 (m, 12H). LCMS (M+H)=472.8.

Intermediate 16

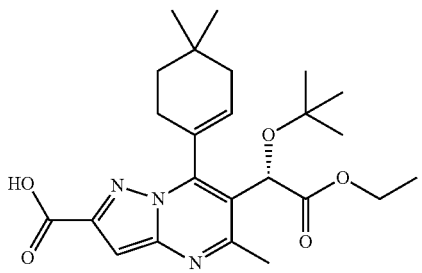 [SMILES: CCOC(=O)[C@@H](OC(C)(C)C)c1c(C)nc2cc(C(=O)O)nn2c1C1=CCC(C)(C)CC1]

(S)-6-(1-(tert-Butoxy)-2-ethoxy-2-oxoethyl)-7-(4,4-dimethylcyclohex-1-en-1-yl)-5-methylpyrazolo[1,5-a]pyrimidine-2-carboxylic acid To a solution of (S)-ethyl 6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylate (185 mg, 0.392 mmol) in EtOH (4 mL) was added 1M NaOH (0.392 mL, 0.392 mmol) and the resulting mixture was stirred at room temp for 4 h. A this point LCMS indicates completion of reaction. Solvents were then removed under reduced pressure. Mixture was then diluted with water (3 mL), acidified with 1N HCl, extracted with ethyl acetate (25 mL), washed with brine (10 mL), dried (Na$_2$SO$_4$), filtered and concentrated to afford (S)-6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylic acid (150 mg, 0.338 mmol, 86% yield) as light yellow solid (mixture of atrope iaomers). $^1$H NMR (500 MHz, CDCl$_3$) δ 7.15 (s, 1H), 6.26 (br. s., 0.6H), 5.93 (br. s., 0.4H), 5.53 (s, 0.6H), 5.46 (s, 0.4H), 4.29-4.19 (m, 2H), 2.79 (s, 1H), 2.72 (s, 2H), 2.19-2.14 (m, 2H), 1.77-1.54 (m, 4H), 1.29-1.16 (m, 18H). LCMS (M+H)=444.4.

Intermediate 17

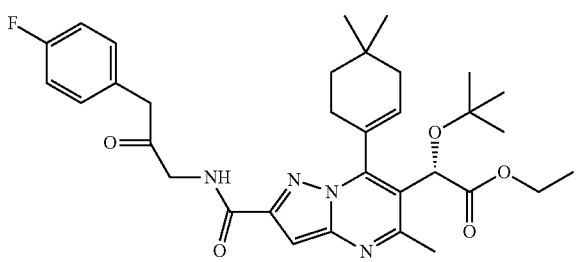 [SMILES: CCOC(=O)[C@@H](OC(C)(C)C)c1c(C)nc2cc(C(=O)NCC(=O)Cc3ccc(F)cc3)nn2c1C1=CCC(C)(C)CC1]

(S)-Ethyl 2-(tert-Butoxy)-2-(7-(4,4-dimethylcyclohex-1-en-1-yl)-2-((3-(4-fluorophenyl)-2-oxopropyl)carbamoyl)-5-methylpyrazolo[1,5-a]pyrimidin-6-yl)acetate To a solution of (S)-6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylic acid (400 mg, 0.902 mmol) in CH$_2$Cl$_2$ (10 mL) was added oxalyl chloride (0.095 mL, 1.082 mmol). 1 drop of DMF was then added and the mixture was stirred at room temp for 1 h. The crude acid chloride was then added to a pre-stirred solution of 1-amino-3-(4-fluorophenyl)propan-2-one, HCl (367 mg, 1.804 mmol) and DIEA (0.945 mL, 5.41 mmol) in CH$_2$Cl$_2$ (10.00 mL) and the resulting solution was stirred at room temperature for 2 h. Water was then added and the mixture was extracted with dichloromethane, dried (Na$_2$SO$_4$), filtered and concentrated. The crude was then purified by flash column chromatograpgy on silica gel column using (5-70% EtOAc/Hex as eluant) to afford (S)-ethyl 2-(tert-butoxy)-2-(7-(4,4-dimethylcyclohex-1-en-1-yl)-2-((3-(4-fluorophenyl)-2-oxopropyl)carbamoyl)-5-methylpyrazolo[1,5-a]pyrimidin-6-yl)acetate (320 mg, 0.540 mmol, 59.9% yield) as light yellow solid (mixture of atrope iaomers). $^1$H NMR (500 MHz, CDCl$_3$) δ 7.77-7.71 (m, 1H), 7.26-7.22 (m, 2H), 7.12-7.03 (m, 3H), 6.25 (br. s., 0.7H), 5.89 (s, 0.3H), 5.53 (s, 0.7H), 5.45 (s, 0.3H), 4.47-4.33 (m, 2H), 4.27-4.19 (m, 2H), 3.81 (s, 2H), 2.76 (s, 1H), 2.69 (s, 2H), 2.20-2.12 (m, 1H), 2.10-1.98 (m, 2H), 1.79-1.68 (m, 1H), 1.60-1.54 (m, 2H), 1.28 (t, J=7.1 Hz, 3H), 1.26 (s, 4H), 1.25 (br. s., 2H), 1.23 (s, 7H), 1.14 (s, 2H). LCMS (M+H)=593.4.

Intermediate 18

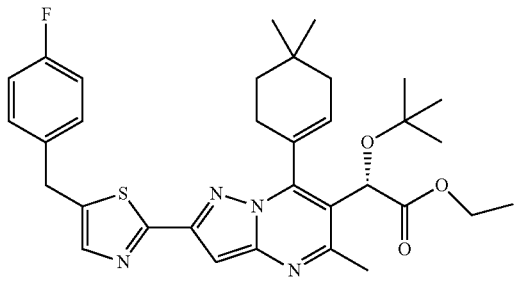 [SMILES: CCOC(=O)[C@@H](OC(C)(C)C)c1c(C)nc2cc(-c3ncc(Cc4ccc(F)cc4)s3)nn2c1C1=CCC(C)(C)CC1]

(S)-Ethyl 2-(tert-butoxy)-2-(7-(4,4-dimethylcyclohex-1-en-1-yl)-2-(5-(4-fluorobenzyl)thiazol-2-yl)-5-methylpyrazolo[1,5-a]pyrimidin-6-yl)acetate To a solution of (S)-ethyl 2-(tert-butoxy)-2-(7-(4,4-dimethylcyclohex-1-en-1-yl)-2-((3-(4-fluorophenyl)-2-oxopropyl)carbamoyl)-5-methylpyrazolo[1,5-a]pyrimidin-6-yl)acetate (100 mg, 0.169 mmol) in toluene was added Lawesson's Reagent (75 mg, 0.186 mmol) and stirr for 15 min at rt, 1 h at 60° C. At this point LCMS indicates desired product as major. Mixture was then concentrated and purified via Biotage (5-30% EtOAc/hexane; 25 g column) to afford (S)-ethyl 2-(tert-butoxy)-2-(7-(4,4-dimethylcyclohex-1-en-1-yl)-2-(5-(4-fluorobenzyl)thiazol-2-yl)-5-methylpyrazolo[1,5-a]pyrimidin-6-yl)acetate (50 mg, 0.085 mmol, 50.2% yield) as off-white solid (mixture of atrope iaomers). $^1$H NMR (500 MHz, CDCl$_3$) δ 7.63 (s, 1H), 7.24 (dd, J=8.6, 5.4 Hz, 2H), 7.08-7.06 (m, 1H), 7.06-7.00 (m, 2H), 6.25 (br. s., 0.7H), 5.90 (br. s., 0.3H), 5.53 (s, 0.7H), 5.45 (br. s., 0.3H), 4.26-4.21 (m, 2H), 4.19 (s, 2H), 3.38-3.22 (m, 1H), 2.76 (s, 1H), 2.68 (s, 2H), 2.23-2.15 (m, 1H), 2.08-1.94 (m, 1H), 1.74-1.50 (m, 3H), 1.30-1.19 (m, 15H), 1.12 (s, 3H). LCMS (M+H)=591.5

Example 10

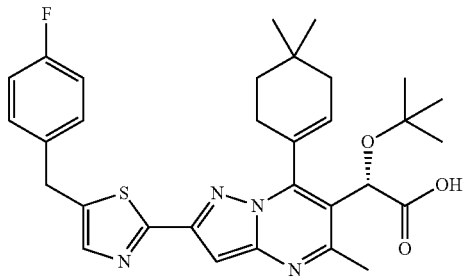 [SMILES: Cc1nc2cc(-c3ncc(Cc4ccc(F)cc4)s3)nn2c(C2=CCC(C)(C)CC2)c1[C@H](OC(C)(C)C)C(=O)O]

(S)-2-(tert-Butoxy)-2-(7-(4,4-dimethylcyclohex-1-en-1-yl)-2-(5-(4-fluorobenzyl)thiazol-2-yl)-5-methylpyrazolo[1,5-a]pyrimidin-6-yl)acetic acid To a solution of (S)-ethyl 2-(tert-butoxy)-2-(7-(4,4-dimethylcyclohex-1-en-1-yl)-2-(5-(4-fluorobenzyl)thiazol-2-yl)-5-methylpyrazolo[1,5-a]pyrimidin-6-yl)acetate (40 mg, 0.068 mmol) in MeOH (1.5 mL) was added 1M NaOH (0.339 mL, 0.339 mmol) and the mixture was heated at 50° C. for 16 h. Mixture was then cooled, concentrated and purified by prep HPLC to afford (S)-2-(tert-butoxy)-2-(7-(4,4-dimethylcyclohex-1-en-1-yl)-2-(5-(4-fluorobenzyl)thiazol-2-yl)-5-methylpyrazolo[1,5-a]pyrimidin-6-yl)acetic acid (26 mg, 0.044 mmol, 64.8% yield) as mixture of atrope isomers (approx 2:1). $^1$H NMR (500 MHz, CDCl$_3$) δ 7.64 (s, 1H), 7.27-7.20 (m, 2H), 7.08 (s, 1H), 7.04 (t, J=8.7 Hz, 2H), 6.47 (br. s., 0.7H), 5.90 (s, 0.3H), 5.71 (s, 0.7H), 5.44 (s, 0.3H), 4.19 (s, 2H), 3.41 (br. s., 1H), 2.74 (s, 1H), 2.65 (s, 2H), 2.34-2.02 (m, 4H), 1.75-1.71 (m, 1H), 1.32 (s, 3H), 1.28 (s, 7H), 1.20 (s, 3H), 1.11 (s, 2H). LCMS (M+H)=563.4.

Intermediate 19

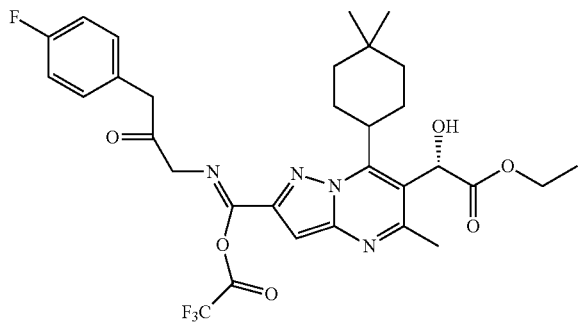 [SMILES: CCOC(=O)[C@@H](O)c1c(C)nc2cc(/C(=N/CC(=O)Cc3ccc(F)cc3)OC(=O)C(F)(F)F)nn2c1C1CCC(C)(C)CC1]

2,2,2-Trifluoroacetic (S,Z)-7-(4,4-dimethylcyclohexyl)-6-(2-ethoxy-1-hydroxy-2-oxoethyl)-N-(3-(4-fluorophenyl)-2-oxopropyl)-5-methylpyrazolo[1,5-a]pyrimidine-2-carbimidic anhydride To a solution of (S)-ethyl 2-(tert-butoxy)-2-(7-(4,4-dimethylcyclohex-1-en-1-yl)-2-((3-(4-fluorophenyl)-2-oxopropyl)carbamoyl)-5-methylpyrazolo[1,5-a]pyrimidin-6-yl)acetate (170 mg, 0.287 mmol) and Et$_3$SiH (0.366 mL, 2.295 mmol) in DCE (5 mL) was added dropwise TFA (2 mL) and the resulting mixture was stirred at room temp for 72 h. At this point LCMS indicates completion of reaction and saturated product with trifluoroacetate as major product (M+H)=635.4. Mixture was then concentrated and dried under high vac to afford crude which was used as is in the next reaction.

Intermediate 20

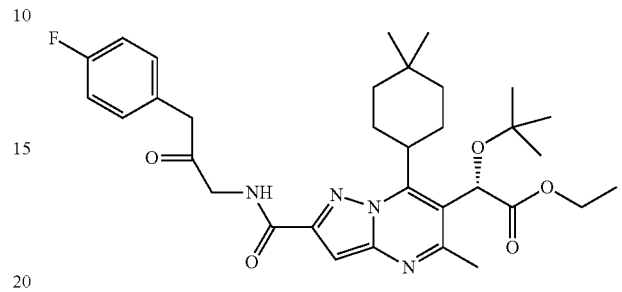

(S)-Ethyl 2-(tert-utoxy)-2-(7-(4,4-dimethylcyclohexyl)-2-((3-(4-fluorophenyl)-2-oxopropyl)carbamoyl)-5-methylpyrazolo[1,5-a]pyrimidin-6-yl)acetate To a stirred solution of 2,2,2-trifluoroacetic (S,Z)-7-(4,4-dimethylcyclohexyl)-6-(2-ethoxy-1-hydroxy-2-oxoethyl)-N-(3-(4-fluorophenyl)-2-oxopropyl)-5-methylpyrazolo[1,5-a]pyrimidine-2-carbimidic anhydride (150 mg, 0.236 mmol) in CH$_2$Cl$_2$ (4 mL) and tBuOAc (2.235 mL, 16.55 mmol) at rt was added 70% HClO$_4$ (0.061 mL, 0.709 mmol). After 3 h, the reaction mixture was diluted with CH$_2$Cl$_2$ (10 mL), carefully quenched with sat. NaHCO$_3$ (5 mL), organic layer separated and washed with brine (10 mL), dried (Na$_2$SO$_4$), filtered and concentrated to give yellow liquid. This was treated with sat. Na$_2$CO$_3$ solution in EtOH (4 mL) at room temp for 30 min (deprotection of trifluoro acetate). Mixture was then concentrated and purified by flash column chromatograpgy on silica gel column using (10-50% EtOAc/Hex as eluant) to afford (S)-ethyl 2-(tert-butoxy)-2-(7-(4,4-dimethylcyclohexyl)-2-((3-(4-fluorophenyl)-2-oxopropyl)carbamoyl)-5-methylpyrazolo[1,5-a]pyrimidin-6-yl)acetate (70 mg, 0.118 mmol, 49.8% yield) as light yellow oil. $^1$H NMR (500 MHz, CDCl$_3$) δ 7.40 (d, J=16.7 Hz, 1H), 7.27-7.18 (m, 3H), 7.06-6.97 (m, 2H), 6.27 (d, J=14.3 Hz, 0.6H), 5.90 (d, J=14.3 Hz, 0.4H), 5.51 (d, J=9.3 Hz, 0.6H), 5.45 (d, J=9.3 Hz, 0.4H), 4.23 (br. s., 1H), 4.15 (q, J=7.1 Hz, 2H), 4.07 (br. s., 1H), 3.90-3.81 (m, 1H), 3.45-3.25 (m, 1H), 2.93-2.85 (m, 1H), 2.82 (br. s., 3H), 2.25-2.14 (m, 1H), 1.98-1.75 (m, 6H), 1.28-1.21 (m, 12H), 1.17 (d, J=7.3 Hz, 3H), 1.12 (d, J=5.7 Hz, 3H). LCMS (M+H)=595.5.

Example 11

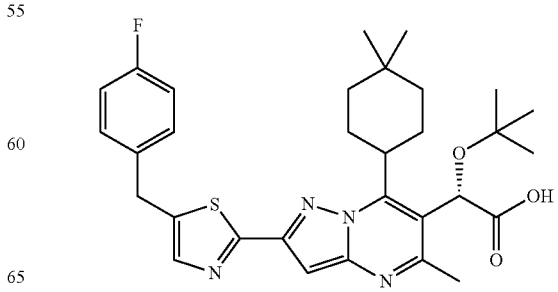

(S)-2-(tert-Butoxy)-2-(7-(4,4-dimethylcyclohexyl)-2-(5-(4-fluorobenzyl)thiazol-2-yl)-5-methylpyrazolo[1,5-a]pyrimidin-6-yl)acetic acid To a solution of (S)-ethyl 2-(tert-butoxy)-2-(7-(4,4-dimethylcyclohexyl)-2-((3-(4-fluorophenyl)-2-oxopropyl)carbamoyl)-5-methylpyrazolo[1,5-a]pyrimidin-6-yl)acetate (58 mg, 0.098 mmol) in toluene was added Lawesson's Reagent (43.4 mg, 0.107 mmol) and stirr for 15 min at rt, 1 h at 60° C. and 16 h at 100° C. At this point LCMS indicates completion of reaction and appearance of desired product. Mixture was then cooled, concentrated and treated with 1N NaOH (0.293 mL, 0.293 mmol) in MeOH (3 mL) at 65° C. for 4 h. Mixture was then cooled and purified by prep HPLC to afford (S)-2-(tert-butoxy)-2-(7-(4,4-dimethylcyclohexyl)-2-(5-(4-fluorobenzyl)thiazol-2-yl)-5-methylpyrazolo[1,5-a]pyrimidin-6-yl)acetic acid (29 mg, 0.051 mmol, 52.7% yield). $^1$H NMR (500 MHz, DMSO-$d_6$) δ 7.31 (br. s., 2H), 7.13 (br. s., 2H), 6.86 (br. s., 1H), 6.33 (s, 0.7H), 5.83 (s, 0.3H), 5.31 (s., 0.7H), 5.20 (s., 0.3H), 4.27 (s, 2H), 2.98-2.81 (m, 4H), 2.58 (s., 2H), 2.16-1.91 (m, 1H), 1.91 (br. s., 3H), 1.60-1.54 (m, 2H), 1.17-1.05 (m, 15H). LCMS (M+H)=565.5

Intermediate 21

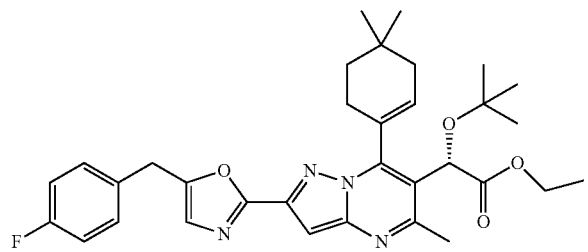 [SMILES: CCOC(=O)[C@@H](OC(C)(C)C)c1c(C)nc2cc(-c3ncc(Cc4ccc(F)cc4)o3)nn2c1C1=CCC(C)(C)CC1]

(S)-Ethyl 2-(tert-butoxy)-2-(7-(4,4-dimethylcyclohex-1-en-1-yl)-2-(5-(4-fluorobenzyl)oxazol-2-yl)-5-methylpyrazolo[1,5-a]pyrimidin-6-yl)acetate To a stirred solution of (S)-ethyl 2-(tert-butoxy)-2-(7-(4,4-dimethylcyclohex-1-en-1-yl)-2-((3-(4-fluorophenyl)-2-oxopropyl)carbamoyl)-5-methylpyrazolo[1,5-a]pyrimidin-6-yl)acetate (100 mg, 0.169 mmol), Ph3P (89 mg, 0.337 mmol) and TEA (0.118 mL, 0.844 mmol) in Acetonitrile (3 mL) was added CCl$_4$ (0.033 mL, 0.337 mmol) and the mixture was stirred at room temp for 5 h. and then 40° C. for 16 h. Mixture was then cooled, concentrated and purified by prep HPLC to afford desired (S)-ethyl 2-(tert-butoxy)-2-(7-(4,4-dimethylcyclohex-1-en-1-yl)-2-(5-(4-fluorobenzyl)oxazol-2-yl)-5-methylpyrazolo[1,5-a]pyrimidin-6-yl)acetate (26 mg, 0.045 mmol, 26.8% yield) ester as off-white solid (mixture of atropisomers). $^1$H NMR (500 MHz, CDCl$_3$) δ 7.32-7.28 (m, 2H), 7.08-7.00 (m, 3H), 6.93-6.88 (m, 1H), 6.26 (br. s., 0.7H), 5.93 (br. s., 0.3H), 5.54 (s, 0.7H), 5.48 (br. s., 0.7H), 4.27-4.11 (m, 2H), 4.08 (s, 2H), 3.38-3.26 (m, 1H), 2.77 (s, 1H), 2.69 (s, 2H), 2.26-2.14 (m, 2H), 2.10-1.98 (m, 2H), 1.80-1.70 (m, 1H), 1.27 (s, 3H), 1.24 (s, 7H), 1.23-1.19 (m, 5H), 1.14 (s, 3H). LCMS (M+H)=575.5.

Example 12

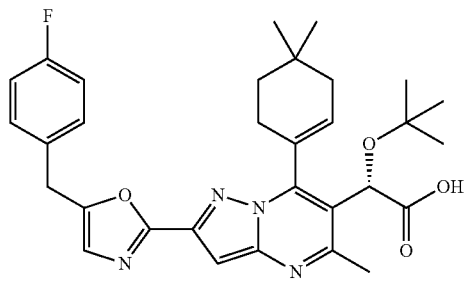 [SMILES: Cc1nc2cc(-c3ncc(Cc4ccc(F)cc4)o3)nn2c(C2=CCC(C)(C)CC2)c1[C@H](OC(C)(C)C)C(=O)O]

(S)-2-(tert-Butoxy)-2-(7-(4,4-dimethylcyclohex-1-en-1-yl)-2-(5-(4-fluorobenzyl)oxazol-2-yl)-5-methylpyrazolo[1,5-a]pyrimidin-6-yl)acetic acid To a solution of(S)-ethyl 2-(tert-butoxy)-2-(7-(4,4-dimethylcyclohex-1-en-1-yl)-2-(5-(4-fluorobenzyl)oxazol-2-yl)-5-methylpyrazolo[1,5-a]pyrimidin-6-yl)acetate (26 mg, 0.045 mmol) in MeOH (1.5 mL) was added 1M NaOH (0.226 mL, 0.226 mmol) and the mixture was heated at 65° C. for 4 h. Mixture was then cooled and purified by prep HPLC to afford (S)-2-(tert-butoxy)-2-(7-(4,4-dimethylcyclohex-1-en-1-yl)-2-(5-(4-fluorobenzyl)oxazol-2-yl)-5-methylpyrazolo[1,5-a]pyrimidin-6-yl)acetic acid (14.8 mg, 0.026 mmol, 56.9% yield) as approx 2:1 mixture of atropisomers. $^1$H NMR (500 MHz, DMSO-$d_6$) δ 7.41-7.35 (m, 2H), 7.18 (t, J=8.9 Hz, 2H), 7.09 (s, 1H), 6.95 (s, 1H), 6.32 (br. s., 0.6H), 5.86 (br. s., 0.4H), 5.32 (br. s., 0.6H), 5.22 (br. s., 0.4H), 4.16 (s, 2H), 2.67 (s, 1.2H), 2.60 (s, 1.8H), 2.24-2.14 (m, 1H), 2.09 (s, 1H), 2.04 (br. s., 1H), 1.67-1.54 (m, 1H), 1.62-1.51 (m, 2H), 1.19 (s, 3H), 1.15 (s, 6H), 1.12 (s, 3H), 1.08 (s, 3H). LCMS (M+H)=547.4.

Intermediate 22

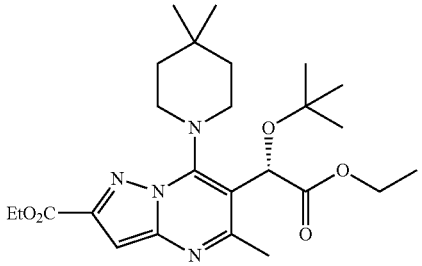 [SMILES: CCOC(=O)c1cc2nc(C)c([C@H](OC(C)(C)C)C(=O)OCC)c(N3CCC(C)(C)CC3)n2n1]

(S)-Ethyl 6-(1-(tert-butoxy)-2-ethoxy-2-oxoethyl)-7-(4,4-dimethylpiperidin-1-yl)-5-methylpyrazolo[1,5-a]pyrimidine-2-carboxylate To a solution of (S)-ethyl 6-(1-(tert-butoxy)-2-ethoxy-2-oxoethyl)-7-iodo-5-methylpyrazolo[1,5-a]pyrimidine-2-carboxylate (300 mg, 0.613 mmol) and 4,4-dimethylpiperidine, HCl (138 mg, 0.920 mmol) in NMP (3 mL) was added DIEA (0.321 mL, 1.839 mmol) and the mixture was heated at 50° C. for 4 h. At this point LCMS indicates approx 40% conversion so mixture was heated at same temp over weekend. At this point LCMS indicates completion of reaction.

Mixture was then cooled to room temp and purified by prep HPLC to afford (S)-ethyl 6-(1-(tert-butoxy)-2-ethoxy-2-oxoethyl)-7-(4,4-dimethylpiperidin-1-yl)-5-methylpyrazolo[1,5-a]pyrimidine-2-carboxylate (220 mg, 0.464 mmol, 76% yield) as off-white solid. $^1$H NMR (500 MHz CDCl$_3$) δ 7.03 (s, 1H), 5.99 (s, 1H), 4.47 (q, J=7.1 Hz, 2H), 4.30-4.11 (m, 2H), 3.21-2.98 (m, 4H), 2.65 (s, 3H), 1.70-1.62 (m, 2H), 1.59-1.50 (m, 2H), 1.46 (t, J=7.1 Hz, 3H), 1.26 (s, 9H), 1.25-1.22 (m, 3H), 1.14 (s, 6H). LCMS (M+H)=475.2.

Intermediate 23

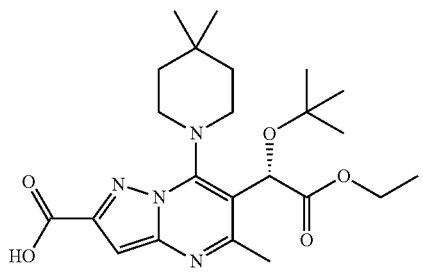 [SMILES: CCOC(=O)[C@@H](OC(C)(C)C)c1c(C)nc2cc(C(=O)O)nn2c1N1CCC(C)(C)CC1]

(S)-6-(1-(tert-Butoxy)-2-ethoxy-2-oxoethyl)-7-(4,4-dimethylpiperidin-1-yl)-5-methylpyrazolo[1,5-a]pyrimidine-2-carboxylic acid To a solution of (S)-ethyl 6-(1-(tert-butoxy)-2-ethoxy-2-oxoethyl)-7-(4,4-dimethylpiperidin-1-yl)-5-methylpyrazolo[1,5-a]pyrimidine-2-carboxylate (410 mg, 0.864 mmol) in EtOH (10 mL) was added 1M NaOH (0.864 mL, 0.864 mmol) and the resulting mixture was stirred at room temp for 4 h. At this point LCMS indicates completion of reaction. Solvents were then removed under reduced pressure. Mixture was then diluted with water (3 mL), acidified with 1N HCl, extracted with ethyl acetate (25 mL), washed with brine (10 mL), dried (Na$_2$SO$_4$), filtered and concentrated to afford (S)-6-(1-(tert-butoxy)-2-ethoxy-2-oxoethyl)-7-(4,4-dimethylpiperidin-1-yl)-5-methylpyrazolo[1,5-a]pyrimidine-2-carboxylic acid (337 mg, 0.755 mmol, 87% yield) as light yellow solid. $^1$H NMR (400 MHz, CDCl$_3$) δ 7.14 (s, 1H), 5.95 (s, 1H), 4.31-4.16 (m, 2H), 2.66 (s, 3H), 1.82-1.60 (m, 4H), 1.60-1.46 (m, 4H), 1.28-1.22 (m, 12H), 1.14 (s, 6H). LCMS (M+H)=447.4.

Intermediate 24

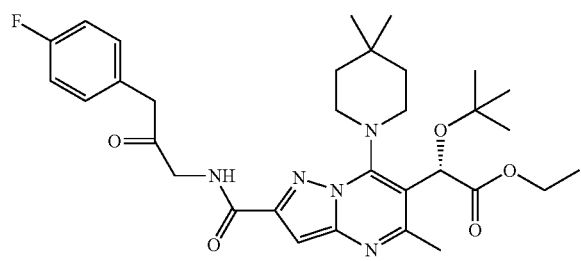 [SMILES: CCOC(=O)[C@@H](OC(C)(C)C)c1c(C)nc2cc(C(=O)NCC(=O)Cc3ccc(F)cc3)nn2c1N1CCC(C)(C)CC1]

(S)-Ethyl 2-(tert-butoxy)-2-(7-(4,4-dimethylpiperidin-1-yl)-2-((3-(4-fluorophenyl)-2-oxopropyl)carbamoyl)-5-methylpyrazolo[1,5-a]pyrimidin-6-yl)acetate To a solution of (S)-6-(1-(tert-butoxy)-2-ethoxy-2-oxoethyl)-7-(4,4-dimethylpiperidin-1-yl)-5-methylpyrazolo[1,5-a]pyrimidine-2-carboxylic acid (200 mg, 0.448 mmol) in CH$_2$Cl$_2$ (3 mL) was added oxalyl chloride (0.059 mL, 0.672 mmol) 1 drop of DMF was then added and the mixture was stirred at room temp for 1 h. The crude acid chloride was then added to a pre-stirred solution of 1-amino-3-(4-fluorophenyl)propan-2-one, HCl (182 mg, 0.896 mmol) and DIEA (0.469 mL, 2.69 mmol) in CH$_2$Cl$_2$ (3.00 mL) and the resulting solution was stirred at room temperature for 2 h. Water was then added and the mixture was extracted with dichloromethane, dried (Na$_2$SO$_4$), filtered and concentrated. The crude was then purified by flash column chromatograpgy on silica gel column using (50-100% EtOAc/Hexane as eluant) to afford (S)-ethyl 2-(tert-butoxy)-2-(7-(4,4-dimethylpiperidin-1-yl)-2-((3-(4-fluorophenyl)-2-oxopropyl)carbamoyl)-5-methylpyrazolo[1,5-a]pyrimidin-6-yl)acetate (150 mg, 0.252 mmol, 56.2% yield) as light yellow solid. $^1$H NMR (400 MHz, CDCl$_3$) δ 7.83 (t, J=4.8 Hz, 1H), 7.27-7.22 (m, 2H), 7.12-7.03 (m, 3H), 6.00 (s, 1H), 4.44 (d, J=4.5 Hz, 2H), 4.30-4.10 (m, 4H), 3.83 (s, 2H), 2.64 (s, 3H), 1.73-1.63 (m, 2H), 1.58 (s, 9H), 1.32-1.21 (m, 13H). LCMS (M+H)=596.5.

Intermediate 25

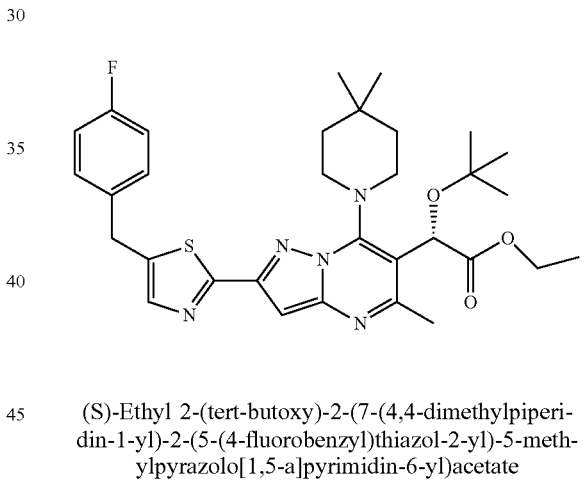

(S)-Ethyl 2-(tert-butoxy)-2-(7-(4,4-dimethylpiperidin-1-yl)-2-(5-(4-fluorobenzyl)thiazol-2-yl)-5-methylpyrazolo[1,5-a]pyrimidin-6-yl)acetate To a solution of (S)-ethyl 2-(tert-butoxy)-2-(7-(4,4-dimethylpiperidin-1-yl)-2-((3-(4-fluorophenyl)-2-oxopropyl)carbamoyl)-5-methylpyrazolo[1,5-a]pyrimidin-6-yl)acetate (150 mg, 0.252 mmol) in toluene was added Lawesson's Reagent (306 mg, 0.755 mmol) and stirr for 15 min at rt, 30 min at 60° C. and 5 h at 100° C. Then, the resulting clear yellow mixture was cooled, concentrated and purified by column chromatograophy on silica gel column using (5-30% EtOAc/Hexane as eluant) to afford (S)-ethyl 2-(tert-butoxy)-2-(7-(4,4-dimethylpiperidin-1-yl)-2-(5-(4-fluorobenzyl)thiazol-2-yl)-5-methylpyrazolo[1,5-a]pyrimidin-6-yl)acetate (50 mg, 0.084 mmol, 33.4% yield) as off white solid. $^1$H NMR (400 MHz, CDCl$_3$) δ 7.65 (s, 1H), 7.28-7.23 (m, 2H), 7.08-6.98 (m, 3H), 6.00 (s, 1H), 4.31-4.10 (m, 4H), 2.65 (s, 3H), 1.76-1.48 (m, 8H), 1.26 (s, 9H), 1.26-1.19 (m, 3H), 1.14 (s, 6H). LCMS (M+H)=594.4.

Example 13

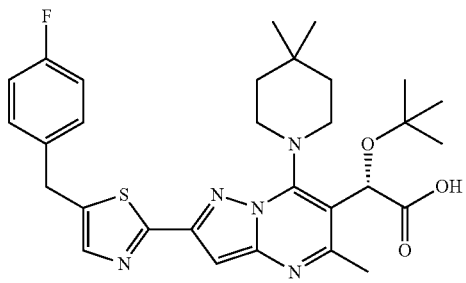 [SMILES: Cc1nc2cc(-c3ncc(Cc4ccc(F)cc4)s3)nn2c(N2CCC(C)(C)CC2)c1[C@H](OC(C)(C)C)C(=O)O]

(S)-2-(tert-Butoxy)-2-(7-(4,4-dimethylpiperidin-1-yl)-2-(5-(4-fluorobenzyl)thiazol-2-yl)-5-methylpyrazolo[1,5-a]pyrimidin-6-yl)acetic acid To a solution of (S)-ethyl 2-(tert-butoxy)-2-(7-(4,4-dimethylpiperidin-1-yl)-2-(5-(4-fluorobenzyl)thiazol-2-yl)-5-methylpyrazolo[1,5-a]pyrimidin-6-yl)acetate (50 mg, 0.084 mmol) in MeOH (2 mL) was added 1N NaOH (0.253 mL, 0.253 mmol) and the mixture was heated at 60° C. for 5 h. Mixture was then cooled and purified by prep HPLC to afford (S)-2-(tert-butoxy)-2-(7-(4,4-dimethylpiperidin-1-yl)-2-(5-(4-fluorobenzyl)thiazol-2-yl)-5-methylpyrazolo[1,5-a]pyrimidin-6-yl)acetic acid (27.3 mg, 0.048 mmol, 57.3% yield). $^1$H NMR (500 MHz, DMSO-$d_6$) δ 7.78 (s, 1H), 7.37 (dd, J=8.4, 5.6 Hz, 2H), 7.18 (t, J=8.9 Hz, 2H), 6.93 (s, 1H), 5.76 (br. s., 1H), 4.28 (s, 2H), 2.54 (s, 2H), 1.65-1.55 (m, 2H), 1.50-1.42 (m, 2H), 1.19 (s, 9H), 1.07 (s., 6H). LCMS (M+H)=566.3.

Intermediate 26

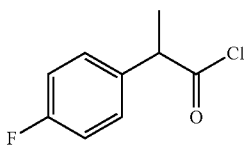

2-(4-Fluorophenyl)propanoyl chloride

To a solution of 2-(4-fluorophenyl)propanoic acid (3 g, 17.84 mmol) in CH$_2$Cl$_2$ (40 mL) was added oxalyl chloride (15.16 mL, 30.3 mmol) followed by few drops of DMF and the resulting mixture was stirred at room temp for 1 h. At this point LCMS (in methanol) indicates corresponding methyl ester. Mixture was then concentrated and dried under high vac for 1 h to afford 2-(4-fluorophenyl)propanoyl chloride as light brown oil, which was used in the next step without further purification

Intermediate 27

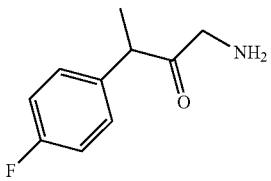

1-Amino-3-(4-fluorophenyl)butan-2-one, HCl

To a −78° C. solution of 1M LiHMDS (29.4 mL, 29.4 mmol) in THF (80 mL) was added dropwise THF (10 mL) solution of methyl 2-isocyanoacetate (2.63 g, 26.5 mmol) over 5 min. After 30 min, a THF (20 mL) solution of 2-(4-fluorophenyl)propanoyl chloride (3.3 g, 17.68 mmol) was added over 5 min. After 1 h, the cold bath was removed and the mixture was stirred at room temp for 16 h. Water (25 mL) was then added and the mixture was extracted with ethyl acetate (100 mL), washed with brine (50 mL), dried (Na$_2$SO$_4$), filtered and concentrated. The residue was then refluxed with conc. HCl (40 mL) for 3 h. Mixture was then concentrated and the residue was triturated with ethyl acetate and dried under high vac to afford 1-amino-3-(4-fluorophenyl)butan-2-one, HCl (2.5 g, 11.49 mmol, 64.9% yield) as tan solid. $^1$H NMR (500 MHz, DMSO-$d_6$) δ 7.39-7.32 (m, 2H), 7.27-7.12 (m, 2H), 4.16-3.99 (m, 2H), 3.81-3.68 (m, 1H), 1.36 (d, J=7.1 Hz, 3H). LCMS (M+H)=182.2.

Intermediate 28

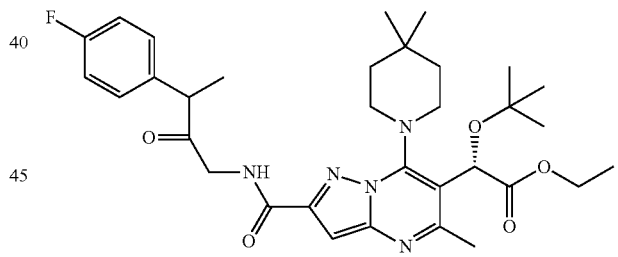

(2S)-Ethyl 2-(tert-butoxy)-2-(7-(4,4-dimethylpiperidin-1-yl)-2-((3-(4-fluorophenyl)-2-oxobutyl)carbamoyl)-5-methylpyrazolo[1,5-a]pyrimidin-6-yl)acetate To a solution of (S)-6-(1-(tert-butoxy)-2-ethoxy-2-oxoethyl)-7-(4,4-dimethylpiperidin-1-yl)-5-methylpyrazolo[1,5-a]pyrimidine-2-carboxylic acid (100 mg, 0.224 mmol) in CH$_2$Cl$_2$ (2 mL) was added oxalyl chloride (0.123 mL, 0.246 mmol). 1 drop of DMF was then added and the mixture was stirred at room temp for 1 h. The crude acid chloride was then added to a pre-stirred solution of 1-amino-3-(4-fluorophenyl)butan-2-one, HCl (73.1 mg, 0.336 mmol) and DIEA (0.235 mL, 1.344 mmol) in CH$_2$Cl$_2$ (2.000 mL) and the resulting solution was stirred at room temperature for 4 h. Water was then added and the mixture was extracted with dichloromethane, dried (Na$_2$SO$_4$), filtered and concentrated. The crude was then purified by flash column chromatograpgy on silica gel column using (5-70% EtOAc/Hex as eluant) to afford (2S)-ethyl 2-(tert-butoxy)-2-(7-(4,4-dimethylpiperidin-1-yl)-2-((3-(4-fluorophenyl)-2-oxobutyl)carbamoyl)-5-methylpyrazolo[1,5-a]pyrimidin-6-yl)acetate (80 mg, 0.131 mmol, 58.6% yield) as light yellow solid. $^1$H NMR (400 MHz, CDCl$_3$) δ 7.79 (t, J=4.4 Hz, 1H), 7.26 (dd, J=7.9, 5.4 Hz, 2H), 7.11-7.03 (m, 3H), 6.00 (s, 1H), 4.35-4.31 (m, 2H), 4.30-4.10 (m, 3H), 3.91 (q, J=7.0 Hz, 1H), 2.64 (s, 3H), 1.68-1.63 (m, 5H), 1.61-1.54 (m, 2H), 1.51 (d, J=7.0 Hz, 3H), 1.27-1.22 (m, 12H), 1.19 (s., 6H). LCMS (M+H)=610.7.

Example 14

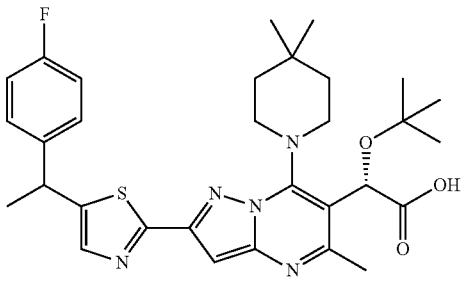 [SMILES: Cc1nc2cc(-c3ncc(C(C)c4ccc(F)cc4)s3)nn2c(N2CCC(C)(C)CC2)c1[C@H](OC(C)(C)C)C(=O)O]

(2S)-2-(tert-Butoxy)-2-(7-(4,4-dimethylpiperidin-1-yl)-2-(5-(1-(4-fluorophenyl)ethyl)thiazol-2-yl)-5-methylpyrazolo[1,5-a]pyrimidin-6-yl)acetic acid To a solution of (2S)-ethyl 2-(tert-butoxy)-2-(7-(4,4-dimethylpiperidin-1-yl)-2-((3-(4-fluorophenyl)-2-oxobutyl)carbamoyl)-5-methylpyrazolo[1,5-a]pyrimidin-6-yl)acetate (67 mg, 0.110 mmol) in toluene was added Lawesson's Reagent (48.9 mg, 0.121 mmol) and stirr for 15 min at rt, 1 h at 60° C. 2 h. At this point LCMS indicates completion of reaction ans appearance of desired product. Mixture was then cooled, concentrated and treated with 1M NaOH (0.330 mL, 0.330 mmol) in MeOH (3 mL) at 65° C. for 4 h. Mixture was then cooled and purified by prep HPLC to afford (2S)-2-(tert-butoxy)-2-(7-(4,4-dimethylpiperidin-1-yl)-2-(5-(1-(4-fluorophenyl)ethyl)thiazol-2-yl)-5-methylpyrazolo[1,5-a]pyrimidin-6-yl)acetic acid (40 mg, 0.069 mmol, 62.8% yield). $^1$H NMR (500 MHz, DMSO-d$_6$) δ 7.76 (s, 1H), 7.39 (br. s., 2H), 7.17 (t, J=8.5 Hz, 2H), 6.88 (s, 1H), 5.59 (br. s., 1H), 4.56 (d, J=6.7 Hz, 1H), 1.91 (s, 3H), 1.68 (d, J=6.7 Hz, 3H), 1.59 (br. s., 2H), 1.45 (br. s., 2H), 1.15 (s, 9H), 1.05 (br. s., 6H). Four missing piperidine hydrogens. LCMS (M+H)=580.7.

Intermediate 29

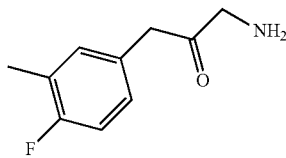

1-Amino-3-(4-fluoro-3-methylphenyl)propan-2-one, HCl

To a −78° C. solution of 1M LiHMDS (19.57 mL, 19.57 mmol) in THF (70 mL) was added dropwise THF (10 mL) solution of methyl 2-isocyanoacetate (1.752 g, 17.68 mmol) over 5 min. After 30 min, a THF (20 mL) solution of 2-(4-fluoro-3-methylphenyl)acetyl chloride (2.2 g, 11.79 mmol) was added over 5 min. After 1 h, the cold bath was removed and the mixture was stirred at room temp for 16 h. Water (25 mL) was then added and the mixture was extracted with ethyl acetate (100 mL), washed with brine (50 mL), dried (Na$_2$SO$_4$), filtered and concentrated. The residue was then refluxed with conc. HCl (30 mL) for 3 h. Mixture was then cooled to room temperature and the solids were collected by filtration, washed with ethyl acetate and dried under high vac to afford 1-amino-3-(4-fluoro-3-methylphenyl)propan-2-one, HCl (1.2 g, 5.51 mmol, 46.8% yield) as tan solid. $^1$H NMR (400 MHz, DMSO-d$_6$) δ 7.24-6.97 (m, 3H), 4.01 (br. s., 2H), 3.41 (br. s., 2H), 2.23 (s, 3H). LCMS (M+H)=182.2.

Intermediate 30

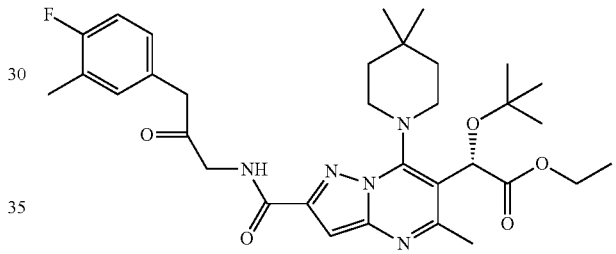

(S)-Ethyl 2-(tert-Butoxy)-2-(7-(4,4-dimethylpiperidin-1-yl)-2-((3-(4-fluoro-3-methylphenyl)-2-oxopropyl)carbamoyl)-5-methylpyrazolo[1,5-a]pyrimidin-6-yl)acetate To a solution of (S)-6-(1-(tert-butoxy)-2-ethoxy-2-oxoethyl)-7-(4,4-dimethylpiperidin-1-yl)-5-methylpyrazolo[1,5-a]pyrimidine-2-carboxylic acid (100 mg, 0.224 mmol) in CH$_2$Cl$_2$ (2 mL) was added oxalyl chloride (0.123 mL, 0.246 mmol) 1 drop of DMF was then added and the mixture was stirred at room temp for 1 h. The crude acid chloride was then added to a pre-stirred solution of 1-amino-3-(4-fluoro-3-methylphenyl)propan-2-one, HCl (73.1 mg, 0.336 mmol) and DIEA (0.235 mL, 1.344 mmol) in CH$_2$Cl$_2$ (2.000 mL) and the resulting solution was stirred at room temperature for 4 h. Water was then added and the mixture was extracted with dichloromethane, dried (Na$_2$SO$_4$), filtered and concentrated. The crude was then purified by flash column chromatograpgy on silica gel column using (5-70% EtOAc/Hexane as eluant) to afford (S)-ethyl 2-(tert-butoxy)-2-(7-(4,4-dimethylpiperidin-1-yl)-2-((3-(4-fluoro-3-methylphenyl)-2-oxopropyl)carbamoyl)-5-methylpyrazolo[1,5-a]pyrimidin-6-yl)acetate (75 mg, 0.123 mmol, 54.9% yield) as light yellow solid. $^1$H NMR (400 MHz, CDCl$_3$) δ 7.83 (t, J=4.5 Hz, 1H), 7.12-7.03 (m, 3H), 7.03-6.96 (m, 1H), 5.99 (s, 1H), 4.42 (d, J=4.5 Hz, 2H), 4.30-4.10 (m, 3H), 3.78 (s, 2H), 2.64 (s, 3H), 2.29 (d, J=1.8 Hz, 3H), 1.77-1.63

(m, 2H), 1.61-1.50 (m, 2H), 1.29-1.21 (m, 12H), 1.17 (s, 6H). 4 missing piperidine hydrogens. LCMS (M+H)=610.7.

Example 15

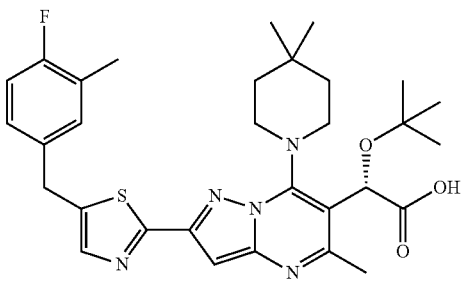 [SMILES: Cc1cc(Cc2cnc(-c3cc4nc(C)c([C@H](OC(C)(C)C)C(=O)O)c(N5CCC(C)(C)CC5)n4n3)s2)ccc1F]

(S)-2-(tert-Butoxy)-2-(7-(4,4-dimethylpiperidin-1-yl)-2-(5-(4-fluoro-3-methylbenzyl)thiazol-2-yl)-5-methylpyrazolo[1,5-a]pyrimidin-6-yl)acetic acid To a solution of (S)-ethyl 2-(tert-butoxy)-2-(7-(4,4-dimethylpiperidin-1-yl)-2-((3-(4-fluoro-3-methylphenyl)-2-oxopropyl)carbamoyl)-5-methylpyrazolo[1,5-a]pyrimidin-6-yl)acetate (70 mg, 0.115 mmol) in toluene was added Lawesson's Reagent (51.1 mg, 0.126 mmol) and stirr for 15 min at rt, 1 h at 60° C. 2 h. At this point LCMS indicates completion of reaction ans appearance of desired product. Mixture was then cooled, concentrated and treated with 1M NaOH (0.344 mL, 0.344 mmol) in MeOH (3 mL) at 65° C. for 4 h. Mixture was then cooled and purified by prep HPLC to afford (S)-2-(tert-butoxy)-2-(7-(4,4-dimethylpiperidin-1-yl)-2-(5-(4-fluoro-3-methylbenzyl)thiazol-2-yl)-5-methylpyrazolo[1,5-a]pyrimidin-6-yl)acetic acid (37 mg, 0.064 mmol, 55.6% yield). $^1$H NMR (500 MHz, DMSO-d$_6$) δ 7.75 (s, 1H), 7.22 (d, J=6.7 Hz, 1H), 7.15 (br. s., 1H), 7.12-7.01 (m, 1H), 6.88 (s, 1H), 5.58 (s, 1H), 4.20 (s, 2H), 2.21 (s, 3H), 1.91 (s, 3H), 1.59 (br. s., 2H), 1.45 (br. s., 2H), 1.15 (s, 9H), 1.05 (br. s., 6H). Four missing piperidine hydrogens. LCMS (M+H)=580.7.

Intermediate 31

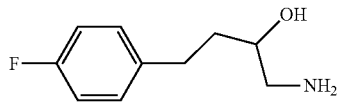 [SMILES: NCC(O)CCc1ccc(F)cc1]

1-Amino-4-(4-Fluorophenyl)butan-2-ol

TMS-CN (2.62 mL, 19.52 mmol) was added dropwise to a mixture of 3-(4-fluorophenyl)propanal (2.7 g, 17.74 mmol) and ZnI$_2$ (0.283 g, 0.887 mmol) in a dry rounbottom flask and the mixture was stirred at room temp for 1 h. The crude cyanohydrin ether was then dissolved in ether (5 mL) and added dropwise to a 2M LiAlH$_4$/THF (9.76 mL, 19.52 mmol) in ether (20 mL) and stirred at room temp for 1 h. Water (1 mL) was then added dropwise, followed by 15% NaOH (1 mL) and then water (2 mL). Mixture was the stirred for 15 min (granular yellow precipitate were formed). Filtration, drying (Na$_2$SO$_4$) and concentration gave a 1-amino-4-(4-fluorophenyl)butan-2-ol (1.7 g, 9.28 mmol, 52.3% yield) as yellow oil, which was used in the next step without further purification. $^1$H NMR (500 MHz, CDCl$_3$) δ 7.25-7.09 (m, 2H), 7.05-6.93 (m, 2H), 3.53 (tt, J=8.2, 3.9 Hz, 1H), 2.90-2.78 (m, 2H), 2.72-2.63 (m, 1H), 2.55 (dd, J=12.6, 8.4 Hz, 1H), 1.77-1.62 (m, 2H).

Intermediate 32

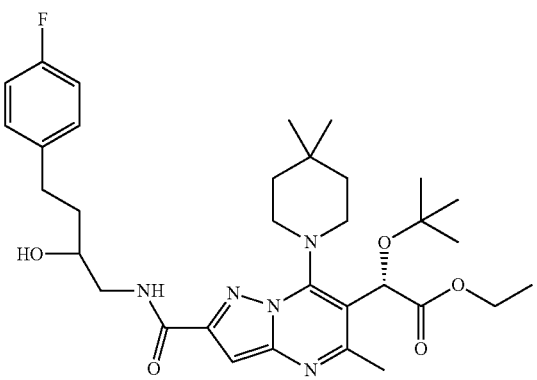 [SMILES: CCOC(=O)[C@@H](OC(C)(C)C)c1c(C)nc2cc(C(=O)NCC(O)CCc3ccc(F)cc3)nn2c1N1CCC(C)(C)CC1]

(2S)-Ethyl 2-(tert-Butoxy)-2-(7-(4,4-dimethylpiperidin-1-yl)-2-((4-(4-fluorophenyl)-2-hydroxybutyl)carbamoyl)-5-methylpyrazolo[1,5-a]pyrimidin-6-yl)acetate To a solution of (S)-6-(1-(tert-butoxy)-2-ethoxy-2-oxoethyl)-7-(4,4-dimethylpiperidin-1-yl)-5-methylpyrazolo[1,5-a]pyrimidine-2-carboxylic acid (150 mg, 0.336 mmol) in CH$_2$Cl$_2$ (3 mL) was added oxalyl chloride (0.185 mL, 0.370 mmol) 1 drop of DMF was then added and the mixture was stirred at room temp for 1 h. The crude acid chloride was then added to a pre-stirred solution of 1-amino-4-(4-fluorophenyl)butan-2-ol, HCl (111 mg, 0.504 mmol) and DIEA (0.352 mL, 2.015 mmol) in CH$_2$Cl$_2$ (3.00 mL) and the resulting solution was stirred at room temperature for 4 h. Water was then added and the mixture was extracted with dichloromethane, dried (Na$_2$SO$_4$), filtered and concentrated. The crude was then purified by flash column chromatograpgy on silica gel column using (5-70% EtOAc/Hex as eluant) to afford (2S)-ethyl 2-(tert-butoxy)-2-(7-(4,4-dimethylpiperidin-1-yl)-2-((4-(4-fluorophenyl)-2-hydroxybutyl)carbamoyl)-5-methylpyrazolo[1,5-a]pyrimidin-6-yl)acetate (90 mg, 0.147 mmol, 43.8% yield) as light yellow solid. $^1$H NMR (400 MHz, CDCl$_3$) δ 7.47 (br. s., 1H), 7.23-7.14 (m, 2H), 7.07 (s, 1H), 7.02-6.93 (m, 2H), 5.97 (s, 1H), 4.31-4.09 (m, 3H), 3.89 (br. s., 1H), 3.78-3.67 (m, 1H), 3.53-3.39 (m, 2H), 2.90-2.69 (m, 3H), 2.64 (s, 3H), 1.90-1.81 (m, 2H), 1.67-1.60 (m, 2H), 1.55 (br. s., 2H), 1.31-1.21 (m, 12H), 1.11 (s, 6H). 4 missing piperidine hydrogens. LCMS (M+H)=612.7

Intermediate 33

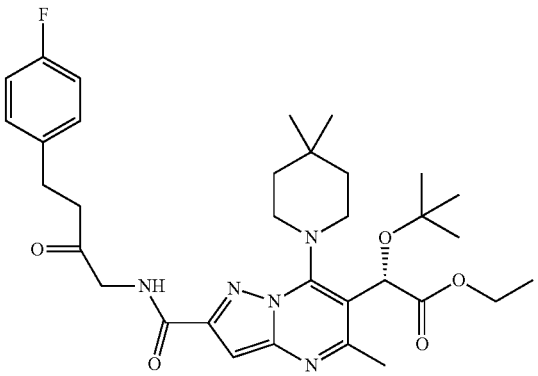 [SMILES: CCOC(=O)[C@@H](OC(C)(C)C)c1c(C)nc2cc(C(=O)NCC(=O)CCc3ccc(F)cc3)nn2c1N1CCC(C)(C)CC1]

(S)-Ethyl 2-(tert-Butoxy)-2-(7-(4,4-dimethylpiperidin-1-yl)-2-((4-(4-fluorophenyl)-2-oxobutyl)carbamoyl)-5-methylpyrazolo[1,5-a]pyrimidin-6-yl)acetate To a solution of (2S)-ethyl 2-(tert-butoxy)-2-(7-(4,4-dimethylpiperidin-1-yl)-2-((4-(4-fluorophenyl)-2-hydroxybutyl)carbamoyl)-5-methylpyrazolo[1,5-a]pyrimidin-6-yl)acetate (90 mg, 0.147 mmol) in CH$_2$Cl$_2$ (3 mL) was added powdered 4 A sieves (55 mg) and NMO (25.9 mg, 0.221 mmol). After stirring the mixture for 10 min, TPAP (5.17 mg, 0.015 mmol) was added and the mixture was stirred at room temp for 1 h. At this point LCMS indicaters completion of reaction. Mixture was then filtered through a pad of silica gel. Filterate was then concentrated and purified by Biotage (0-50% EtOAc/hexane; 25 g column) to afford (S)-ethyl 2-(tert-butoxy)-2-(7-(4,4-dimethylpiperidin-1-yl)-2-((4-(4-fluorophenyl)-2-oxobutyl)carbamoyl)-5-methylpyrazolo[1,5-a]pyrimidin-6-yl)acetate (60 mg, 0.098 mmol, 66.9% yield) as white solid. $^1$H NMR (400 MHz, CDCl$_3$) δ 7.86 (t, J=4.6 Hz, 1H), 7.22-7.14 (m, 2H), 7.07 (s, 1H), 7.03-6.94 (m, 2H), 6.01 (s, 1H), 4.36 (d, J=4.5 Hz, 2H), 4.30-4.07 (m, 3H), 3.06-2.93 (m, 2H), 2.91-2.81 (m, 2H), 2.65 (s, 3H), 1.74-1.62 (m, 5H), 1.62-1.52 (m, 2H), 1.27-1.22 (m, 12H), 1.19 (br. s., 6H). LCMS (M+H)=610.5.

Example 16

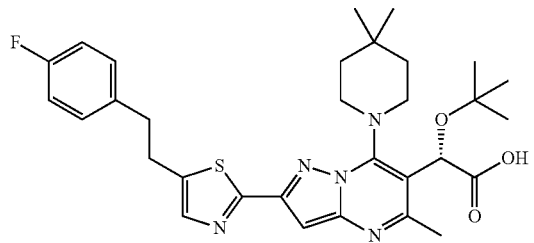 [SMILES: Cc1nc2cc(-c3ncc(CCc4ccc(F)cc4)s3)nn2c(N2CCC(C)(C)CC2)c1[C@H](OC(C)(C)C)C(=O)O]

(S)-2-(tert-Butoxy)-2-(7-(4,4-dimethylpiperidin-1-yl)-2-(5-(4-fluorophenethyl)thiazol-2-yl)-5-methylpyrazolo[1,5-a]pyrimidin-6-yl)acetic acid To a solution of (S)-ethyl 2-(tert-butoxy)-2-(7-(4,4-dimethylpiperidin-1-yl)-2-((4-(4-fluorophenyl)-2-oxobutyl)carbamoyl)-5-methylpyrazolo[1,5-a]pyrimidin-6-yl)acetate (60 mg, 0.098 mmol) in toluene was added Lawesson's Reagent (43.8 mg, 0.108 mmol) and stirr for 15 min at rt, 1 h at 60° C. 2 h. At this point LCMS indicates completion of reaction ans appearance of desired product. Mixture was then cooled, concentrated and treated with 1M NaOH (0.295 mL, 0.295 mmol) in MeOH (3 mL) at 65° C. for 4 h. Mixture was then cooled and purified by prep HPLC to afford (S)-2-(tert-butoxy)-2-(7-(4,4-dimethylpiperidin-1-yl)-2-(5-(4-fluorophenethyl)thiazol-2-yl)-5-methylpyrazolo[1,5-a]pyrimidin-6-yl)acetic acid (35 mg, 0.060 mmol, 61.4% yield). $^1$H NMR (500 MHz, DMSO-d$_6$) δ 7.65 (s, 1H), 7.30 (dd, J=8.2, 5.8 Hz, 2H), 7.10 (t, J=8.7 Hz, 2H), 6.87 (s, 1H), 5.68 (s, 1H), 3.21 (t, J=7.5 Hz, 2H), 2.96 (t, J=7.2 Hz, 2H), 2.55 (s, 3H), 1.60 (br. s., 2H), 1.47 (br. s., 2H), 1.16 (s, 9H), 1.08 (br. s., 6H). 4 missing protons from piperidine LCMS (M+H)=580.6.

Intermediate 34

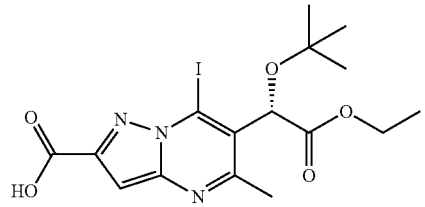 [SMILES: CCOC(=O)[C@@H](OC(C)(C)C)c1c(C)nc2cc(C(=O)O)nn2c1I]

(S)-6-(1-(tert-Butoxy)-2-ethoxy-2-oxoethyl)-7-iodo-5-methylpyrazolo[1,5-a]pyrimidine-2-carboxylic acid To a solution of (S)-ethyl 6-(1-(tert-butoxy)-2-ethoxy-2-oxoethyl)-7-iodo-5-methylpyrazolo[1,5-a]pyrimidine-2-carboxylate (5 g, 10.22 mmol) in Ethanol (100 mL) was added 1M NaOH (10.22 mL, 10.22 mmol) and the resulting mixture was stirred at room temp for 3 h. Mixture was then concentrated and the residue was diluted with water (100 mL) and extracted with ether (100 mL). The aqueous layer was then acidified with 1M HCl and extracted with ether (150 mL), washed with brine (50 mL), dried (Na$_2$SO$_4$), filtered and concentrated. The residue was then triturated with ether/hexane and solids were filtered, washed with hexane and dried under high vac to afford (S)-6-(1-(tert-butoxy)-2-ethoxy-2-oxoethyl)-7-iodo-5-methylpyrazolo[1,5-a]pyrimidine-2-carboxylic acid (3.4 g, 7.37 mmol, 72.1% yield) as off-white solid. $^1$H NMR (400 MHz, CDCl$_3$) δ 7.42-7.38 (m, 1H), 5.57 (s, 1H), 4.31-4.12 (m, 2H), 2.73 (s, 3H), 1.31 (s, 9H), 1.25 (t, J=7.2 Hz, 3H). LCMS (M+H)=462.15.

Intermediate 35

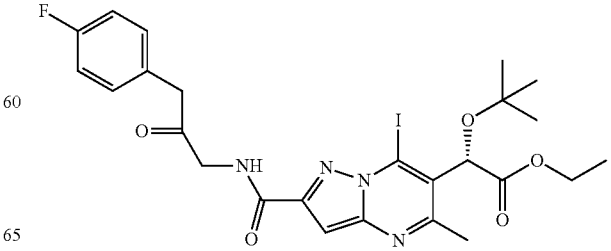

(S)-Ethyl 2-(tert-Butoxy)-2-(2-((3-(4-fluorophenyl)-2-oxopropyl)carbamoyl)-7-iodo-5-methylpyrazolo[1,5-a]pyrimidin-6-yl)acetate To a solution of (S)-6-(1-(tert-butoxy)-2-ethoxy-2-oxoethyl)-7-iodo-5-methylpyrazolo[1,5-a]pyrimidine-2-carboxylic acid (2.5 g, 5.42 mmol) in CH$_2$Cl$_2$ (50 mL) was added oxalyl chloride (0.522 mL, 5.96 mmol) 1 drop of DMF was then added and the mixture was stirred at room temp for 1 h. The crude acid chloride was then added to a pre-stirred solution of 1-amino-3-(4-fluorophenyl)propan-2-one, HCl (1.435 g, 7.05 mmol) and DIEA (5.68 mL, 32.5 mmol) in CH$_2$Cl$_2$ (50.0 mL) and the resulting solution was stirred at room temperature for 2 h. Water was then added and the mixture was extracted with dichloromethane, dried (Na$_2$SO$_4$), filtered and concentrated. The crude was then purified by flash column chromatograpgy on silica gel column using (5-70% EtOAc/Hex as eluant) to afford (S)-ethyl 2-(tert-butoxy)-2-(2-((3-(4-fluorophenyl)-2-oxopropyl)carbamoyl)-7-iodo-5-methylpyrazolo[1,5-a]pyrimidin-6-yl)acetate (2 g, 3.28 mmol, 60.5% yield) as light yellow solid (mixture of rotamers). $^1$H NMR (500 MHz, CDCl$_3$) δ 7.82 (t, J=4.7 Hz, 1H), 7.32 (s, 0.2H), 7.28-7.23 (m, 2H), 7.19 (s, 0.8H), 7.11-7.03 (m, 2H), 5.64 (s, 0.8H), 5.64 (s, 0.2H), 4.45 (d, J=5.0 Hz, 2H), 4.27-4.19 (m, 2H), 3.85-3.81 (m, 2H), 2.74-2.68 (m, 3H), 1.30 (s 2H), 1.29 (s, 7H), 1.26-1.22 (m, 3H). LCMS (M+H)=611.3.

Intermediate 36

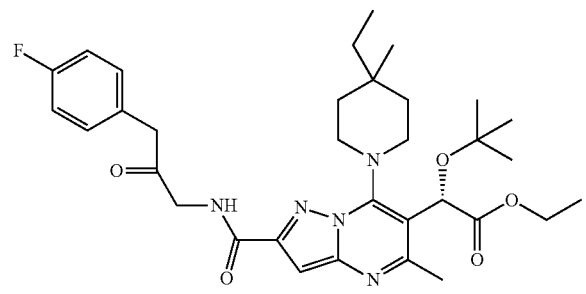 [SMILES: CCOC(=O)[C@@H](OC(C)(C)C)c1c(C)nc2cc(C(=O)NCC(=O)Cc3ccc(F)cc3)nn2c1N1CCC(C)(CC)CC1]

(S)-ethyl 2-(tert-Butoxy)-2-(7-(4-ethyl-4-methylpiperidin-1-yl)-2-((3-(4-fluorophenyl)-2-oxopropyl)carbamoyl)-5-methylpyrazolo[1,5-a]pyrimidin-6-yl)acetate To a solution of (S)-ethyl 2-(tert-butoxy)-2-(2-((3-(4-fluorophenyl)-2-oxopropyl)carbamoyl)-7-iodo-5-methylpyrazolo[1,5-a]pyrimidin-6-yl)acetate (100 mg, 0.164 mmol) and 4-ethyl-4-methylpiperidine (41.7 mg, 0.328 mmol) in NMP (2 mL) was added DIEA (0.086 mL, 0.491 mmol) and the mixture was heated at 60° C. for 4 h. At this point LCMS indicates completion of reaction. Mixture was then cooled to room temp, diluted with water and extracted with ether (3×20 mL), dried (Na$_2$SO$_4$), filtered and concentrated. The residue was then purified by flash chromatography (5-70% EtOAc/hexane) to afford (S)-ethyl 2-(tert-butoxy)-2-(7-(4-ethyl-4-methylpiperidin-1-yl)-2-((3-(4-fluorophenyl)-2-oxopropyl)carbamoyl)-5-methylpyrazolo[1,5-a]pyrimidin-6-yl)acetate (85 mg, 0.139 mmol, 85% yield) as viscous oil. $^1$H NMR (500 MHz, CDCl$_3$) δ 7.83 (t, J=4.5 Hz, 1H), 7.28-7.23 (m, 2H), 7.12-7.01 (m, 3H), 6.00 (s, 1H), 4.44 (d, J=4.7 Hz, 2H), 4.28-4.12 (m, 2H), 3.83 (s, 2H), 2.64 (s, 3H), 1.63-1.60 (m, 2H), 1.56-1.47 (m, 2H), 1.43-1.31 (m, 2H), 1.31-1.27 (m, 2H), 1.26 (s, 9H), 1.25-1.20 (m, 3H), 1.17-1.09 (m, 3H), 0.95 (t, J=7.5 Hz, 3H). LCMS (M+H)=610.5.

Example 17

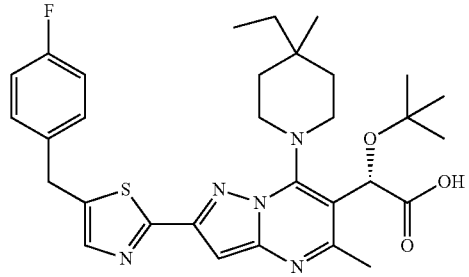 [SMILES: CCC1(C)CCN(c2c([C@H](OC(C)(C)C)C(=O)O)c(C)nc3cc(-c4ncc(Cc5ccc(F)cc5)s4)nn23)CC1]

(S)-2-(tert-Butoxy)-2-(7-(4-ethyl-4-methylpiperidin-1-yl)-2-(5-(4-fluorobenzyl)thiazol-2-yl)-5-methylpyrazolo[1,5-a]pyrimidin-6-yl)acetic acid To a solution of (S)-ethyl 2-(tert-butoxy)-2-(7-(4-ethyl-4-methylpiperidin-1-yl)-2-((3-(4-fluorophenyl)-2-oxopropyl)carbamoyl)-5-methylpyrazolo[1,5-a]pyrimidin-6-yl)acetate (80 mg, 0.131 mmol) in toluene was added Lawesson's Reagent (58.4 mg, 0.144 mmol) and stirr for 15 min at rt, 1 h at 60° C. 2 h. At this point LCMS indicates completion of reaction ans appearance of desired product. Mixture was then cooled, concentrated and treated with 1M NaOH (0.394 mL, 0.394 mmol) in MeOH (2 mL) at 65° C. for 4 h. Mixture was then cooled and purified by prep HPLC to afford (S)-2-(tert-butoxy)-2-(7-(4-ethyl-4-methylpiperidin-1-yl)-2-(5-(4-fluorobenzyl)thiazol-2-yl)-5-methylpyrazolo[1,5-a]pyrimidin-6-yl)acetic acid (58 mg, 0.100 mmol, 76% yield). $^1$H NMR (500 MHz, DMSO-d$_6$) δ 7.78 (s, 1H), 7.38 (dd, J=8.5, 5.5 Hz, 2H), 7.22-7.14 (m, 2H), 6.92 (s, 1H), 5.74 (br. s., 1H), 4.28 (s, 2H), 3.45-3.30 (m, 4H), 2.55 (s, 3H), 1.70-1.62 (m, 2H), 1.57-1.48 (m, 2H), 1.47-1.37 (m, 2H), 1.19 (s, 9H), 1.03 (br. s., 3H), 0.87 (t, J=7.5 Hz, 3H). LCMS (M+H)=580.4.

Intermediate 37

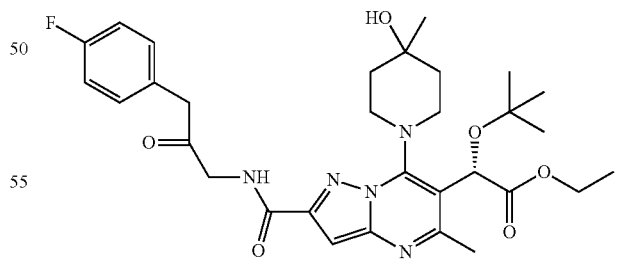

(S)-Ethyl 2-(tert-Butoxy)-2-(2-((3-(4-fluorophenyl)-2-oxopropyl)carbamoyl)-7-(4-hydroxy-4-methylpiperidin-1-yl)-5-methylpyrazolo[1,5-a]pyrimidin-6-yl)acetate To a solution of (S)-ethyl 2-(tert-butoxy)-2-(2-((3-(4-fluorophenyl)-2-oxopropyl)carbamoyl)-7-iodo-5-methylpyrazolo[1,5-a]pyrimidin-6-yl)acetate (100 mg, 0.164 mmol) and 4-methylpiperidin-4-ol, HCl (49.7 mg, 0.328 mmol) in NMP (2 mL) was added DIEA (0.086 mL, 0.491 mmol) and the mixture was heated at 60° C. for 16 h. At this point LCMS indicates completion of reaction. Mixture was then cooled to room temp, diluted with water and extracted with ethyl acetate (2×50 mL), dried (Na$_2$SO$_4$), filtered and concentrated. The residue was then purified by flash chromatography (5-70% EtOAc/hexane) to afford (S)-ethyl 2-(tert-butoxy)-2-(2-((3-(4-fluorophenyl)-2-oxopropyl)carbamoyl)-7-(4-hydroxy-4-methylpiperidin-1-yl)-5-methylpyrazolo[1,5-a]pyrimidin-6-yl)acetate (60 mg, 0.100 mmol, 61.3% yield) as off-white solid. $^1$H NMR (400 MHz, CDCl$_3$) δ 7.83 (br. s., 1H), 7.27-7.21 (m, 2H), 7.10-7.01 (m, 3H), 5.91 (br. s., 1H), 4.42 (dd, J=4.8, 2.5 Hz, 2H), 4.31-4.14 (m, 2H), 3.82 (s, 2H), 3.44-3.34 (m, 2H), 2.65 (s, 3H), 2.39 (t, J=8.2 Hz, 2H), 2.10-2.00 (m, 2H), 1.91-1.75 (m, 2H), 1.45 (s, 3H), 1.25 (s, 9H), 1.27-1.23 (m, 3H). LCMS (M+H)=598.5.

Example 18 and 19

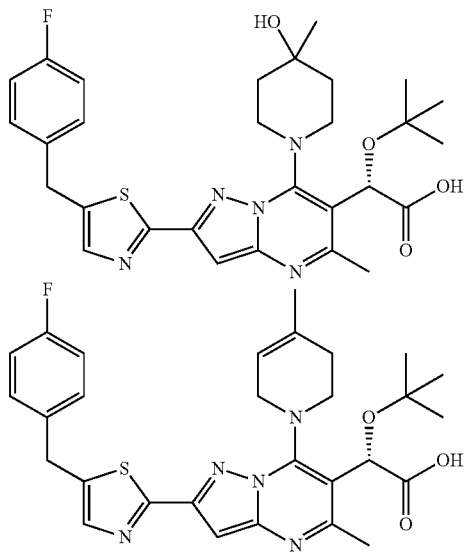

(S)-2-(tert-Butoxy)-2-(2-(5-(4-fluorobenzyl)thiazol-2-yl)-7-(4-hydroxy-4-methylpiperidin-1-yl)-5-methylpyrazolo[1,5-a]pyrimidin-6-yl)acetic acid and (S)-2-(tert-butoxy)-2-(2-(5-(4-fluorobenzyl)thiazol-2-yl)-5-methyl-7-(4-methyl-5,6-dihydropyridin-1(2H)-yl)pyrazolo[1,5-a]pyrimidin-6-yl)acetic acid To a solution of (S)-ethyl 2-(tert-butoxy)-2-(2-((3-(4-fluorophenyl)-2-oxopropyl)carbamoyl)-7-(4-hydroxy-4-methylpiperidin-1-yl)-5-methylpyrazolo[1,5-a]pyrimidin-6-yl)acetate (60 mg, 0.100 mmol) in toluene was added Lawesson's Reagent (44.7 mg, 0.110 mmol) and stirr for 15 min at rt, 1 h at 60° C. 3 h. at this point LCMS indicates deslired product and dehydrated side product. Mixture was then cooled, concentrated and treated with 1M NaOH (0.301 mL, 0.301 mmol) in MeOH (2 mL) at 60° C. for 3 h. Mixture was then cooled and purified by prep HPLC to afford Example 18

(S)-2-(tert-Butoxy)-2-(2-(5-(4-fluorobenzyl)thiazol-2-yl)-7-(4-hydroxy-4-methylpiperidin-1-yl)-5-methylpyrazolo[1,5-a]pyrimidin-6-yl)acetic acid (22 mg, 0.039 mmol, 38.6% yield). $^1$H NMR (500 MHz, DMSO-d$_6$) δ 7.78 (s, 1H), 7.38 (dd, J=8.7, 5.6 Hz, 2H), 7.18 (t, J=8.9 Hz, 2H), 6.88 (s, 1H), 5.55 (s, 1H), 4.42-4.35 (m, 4H), 4.27 (s, 2H), 3.18 (br. s., 2H), 2.49 (s, 3H), 1.70-1.61 (m, 4H), 1.25 (s, 3H), 1.16 (s, 9H). LCMS (M+H)=568.3.

Example 19

(S)-2-(tert-Butoxy)-2-(2-(5-(4-fluorobenzyl)thiazol-2-yl)-5-methyl-7-(4-methyl-5,6-dihydropyridin-1(2H)-yl)pyrazolo[1,5-a]pyrimidin-6-yl)acetic acid (13.4 mg, 0.024 mmol, 24.28% yield). $^1$H NMR (500 MHz, DMSO-d$_6$) δ 7.79 (s, 1H), 7.38 (dd, J=8.5, 5.8 Hz, 2H), 7.18 (t, J=8.9 Hz, 2H), 6.92 (s, 1H), 5.62 (br. s., 1H), 5.56 (br. s., 1H), 4.26 (s, 2H), 2.49 (s, 3H), 2.33-2.18 (m, 2H), 1.78 (s, 3H), 1.13 (s, 9H). LCMS (M+H)=550.3.

Intermediate 38

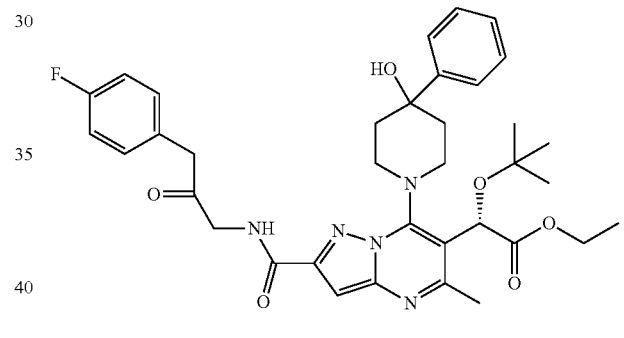

(S)-Ethyl 2-(tert-butoxy)-2-(2-((3-(4-fluorophenyl)-2-oxopropyl)carbamoyl)-7-(4-hydroxy-4-phenylpiperidin-1-yl)-5-methylpyrazolo[1,5-a]pyrimidin-6-yl)acetate To a solution of (S)-ethyl 2-(tert-butoxy)-2-(2-((3-(4-fluorophenyl)-2-oxopropyl)carbamoyl)-7-iodo-5-methylpyrazolo[1,5-a]pyrimidin-6-yl)acetate (60 mg, 0.098 mmol) and 4-phenylpiperidin-4-ol (34.8 mg, 0.197 mmol) in NMP (1 mL) was added DIEA (0.052 mL, 0.295 mmol) and the mixture was heated at 60° C. for 72 h. At this point LCMS indicates completion of reaction. Mixture was then cooled to room temp, diluted with water and extracted with ether (2×50 mL), dried (Na$_2$SO$_4$), filtered and concentrated. The residue was then purified by flash chromatography (5-40% EtOAc/hexane) to afford (S)-ethyl 2-(tert-butoxy)-2-(2-((3-(4-fluorophenyl)-2-oxopropyl)carbamoyl)-7-(4-hydroxy-4-phenylpiperidin-1-yl)-5-methylpyrazolo[1,5-a]pyrimidin-6-yl)acetate (50 mg, 0.076 mmol, 77% yield) as off-white solid. $^1$H NMR (500 MHz, CDCl$_3$) δ 7.89 (br. s., 1H), 7.64 (d, J=7.6 Hz, 2H), 7.43 (br. s., 2H), 7.37-7.32 (m, 1H), 7.27-7.22 (m, 2H), 7.11-7.05 (m, 3H), 5.33 (s, 1H), 4.45 (d, J=4.6 Hz, 2H), 4.30-4.12 (m, 3H), 3.83 (s, 2H), 2.67 (br. s., 3H), 2.30-2.25 (m, 1H), 2.04-1.91 (m, 3H), 1.29 (s, 9H), 1.27-1.21 (m, 3H). L CMS (M+H)=660.6.

Example 20

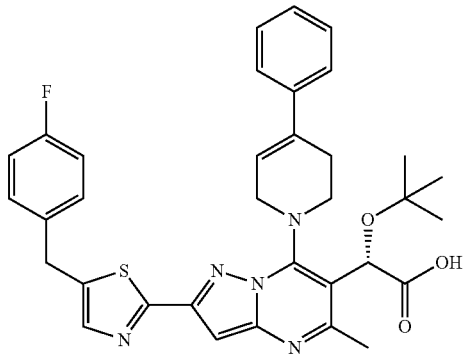 [SMILES: Cc1nc2cc(-c3ncc(Cc4ccc(F)cc4)s3)nn2c(N2CC=C(c3ccccc3)CC2)c1[C@H](OC(C)(C)C)C(=O)O]

(S)-2-(tert-Butoxy)-2-(2-(5-(4-fluorobenzyl)thiazol-2-yl)-5-methyl-7-(4-phenyl-5,6-dihydropyridin-1(2H)-yl)pyrazolo[1,5-a]pyrimidin-6-yl)acetic acid To a solution of (S)-ethyl 2-(tert-butoxy)-2-(2-((3-(4-fluorophenyl)-2-oxopropyl)carbamoyl)-7-(4-hydroxy-4-phenylpiperidin-1-yl)-5-methylpyrazolo[1,5-a]pyrimidin-6-yl)acetate (50 mg, 0.076 mmol) in toluene was added Lawesson's Reagent (33.7 mg, 0.083 mmol) and stirr for 15 min at rt, 1 h at 60° C. 2 h. at tis point LCMS indicates mostly dehydrated product instead of desired product. Mixture was then cooled, concentrated and heated with 1M NaOH (0.227 mL, 0.227 mmol) in MeOH (2 mL) at 70° C. for 3 h. Mixture was then cooled and purified by prep HPLC to afford (S)-2-(tert-butoxy)-2-(2-(5-(4-fluorobenzyl)thiazol-2-yl)-5-methyl-7-(4-phenyl-5,6-dihydropyridin-1(2H)-yl)pyrazolo[1,5-a]pyrimidin-6-yl)acetic acid (9 mg, 0.015 mmol, 19.41% yield). $^1$H NMR (500 MHz, DMSO-d$_6$) δ 7.80 (s, 1H), 7.54 (d, J=7.3 Hz, 2H), 7.44-7.35 (m, 4H), 7.34-7.27 (m, 1H), 7.21-7.13 (m, 2H), 6.96 (s, 1H), 6.37 (br. s., 1H), 5.71 (br. s., 1H), 4.25 (s, 2H), 2.94-2.81 (m, 1H), 2.65-2.61 (m, 2H), 2.56 (s, 1H), 1.15 (s, 9H). LCMS (M+H)=612.5.

Intermediate 39

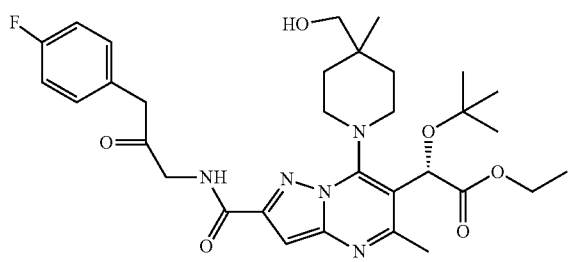 [SMILES: CCOC(=O)[C@@H](OC(C)(C)C)c1c(C)nc2cc(C(=O)NCC(=O)Cc3ccc(F)cc3)nn2c1N1CCC(C)(CO)CC1]

(S)-ethyl 2-(tert-butoxy)-2-(2-((3-(4-fluorophenyl)-2-oxopropyl)carbamoyl)-7-(4-(hydroxymethyl)-4-methylpiperidin-1-yl)-5-methylpyrazolo[1,5-a]pyrimidin-6-yl)acetate To a solution of (S)-ethyl 2-(tert-butoxy)-2-(2-((3-(4-fluorophenyl)-2-oxopropyl)carbamoyl)-7-iodo-5-methyl-pyrazolo[1,5-a]pyrimidin-6-yl)acetate (70 mg, 0.115 mmol) and (4-methylpiperidin-4-yl)methanol•HCl (38.0 mg, 0.229 mmol) in NMP (1.5 mL) was added DIEA (0.060 mL, 0.344 mmol) and the mixture was heated at 60° C. for 4 h. At this point LCMS indicated completion of reaction. Mixture was then cooled to room temp, diluted with water and extracted with ethyl acetate (2×20 mL), dried (Na$_2$SO$_4$), filtered and concentrated. The residue was then purified by flash chromatography (5-70% EtOAc/hexane) to afford (S)-ethyl 2-(tert-butoxy)-2-(2-((3-(4-fluorophenyl)-2-oxopropyl)carbamoyl)-7-(4-(hydroxymethyl)-4-methylpiperidin-1-yl)-5-methylpyrazolo[1,5-a]pyrimidin-6-yl)acetate (47 mg, 0.077 mmol, 67.0% yield) as viscous oil. $^1$H NMR (500 MHz, CDCl$_3$) δ 7.92 (br. s., 1H), 7.25 (dd, J=8.5, 5.4 Hz, 2H), 7.14-7.03 (m, 3H), 5.98 (br. s., 1H), 4.45 (d, J=4.3 Hz, 2H), 4.28-4.09 (m, 3H), 3.84 (s, 2H), 3.76-2.87 (m, 3H), 2.65 (s, 3H), 1.83-1.76 (m, 1H), 1.58 (br. s., 1H), 1.52 (d, J=13.1 Hz, 1H), 1.31-1.19 (m, 15H). LCMS (M+H)=612.6.

Example 21

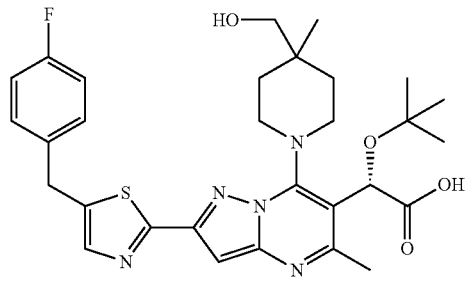 [SMILES: Cc1nc2cc(-c3ncc(Cc4ccc(F)cc4)s3)nn2c(N2CCC(C)(CO)CC2)c1[C@H](OC(C)(C)C)C(=O)O]

(S)-2-(tert-Butoxy)-2-(2-(5-(4-fluorobenzyl)thiazol-2-yl)-7-(4-(hydroxymethyl)-4-methylpiperidin-1-yl)-5-methylpyrazolo[1,5-a]pyrimidin-6-yl)acetic acid To a solution of (S)-ethyl 2-(tert-butoxy)-2-(2-((3-(4-fluorophenyl)-2-oxopropyl)carbamoyl)-7-(4-(hydroxymethyl)-4-methylpiperidin-1-yl)-5-methylpyrazolo[1,5-a]pyrimidin-6-yl)acetate (48 mg, 0.078 mmol) in toluene was added Lawesson's Reagent (34.9 mg, 0.086 mmol) and stirr for 15 min at rt and 80° C. 2 h. Mixture was then concentrated and treated with 1N NaOH (0.235 mL, 0.235 mmol) in MeOH (2 mL) at 70° C. for 5 h. Mixture was then cooled, concentrated and purified by prep HPLC to afford (S)-2-(tert-butoxy)-2-(2-(5-(4-fluorobenzyl)thiazol-2-yl)-7-(4-(hydroxymethyl)-4-methylpiperidin-1-yl)-5-methylpyrazolo[1,5-a]pyrimidin-6-yl)acetic acid (7.9 mg, 0.014 mmol, 17.31% yield). $^1$H NMR (500 MHz, DMSO-d$_6$) δ 7.78 (s, 1H), 7.38 (dd, J=8.7, 5.6 Hz, 2H), 7.18 (t, J=9.0 Hz, 2H), 6.92 (s, 1H), 5.73 (br. s., 1H), 4.65 (br. s., 1H), 4.28 (s, 2H), 1.83-1.74 (m, 1H), 1.68-1.62 (m, 1H), 1.83-1.74 (m, 1H), 1.48-1.43 (m, 1H), 1.36-1.31 (m, 1H), 1.18 (s, 9H), 1.04 (s, 3H). LCMS (M+H)=582.4.

Intermediate 40

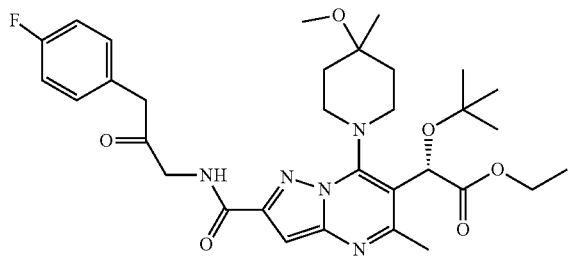 [SMILES: CCOC(=O)[C@@H](OC(C)(C)C)c1c(C)nc2cc(C(=O)NCC(=O)Cc3ccc(F)cc3)nn2c1N1CCC(C)(OC)CC1]

(S)-ethyl 2-(tert-butoxy)-2-(2-((3-(4-fluorophenyl)-2-oxopropyl)carbamoyl)-7-(4-methoxy-4-methylpiperidin-1-yl)-5-methylpyrazolo[1,5-a]pyrimidin-6-yl)acetate To a solution of (S)-ethyl 2-(tert-butoxy)-2-(2-((3-(4-fluorophenyl)-2-oxopropyl)carbamoyl)-7-iodo-5-methylpyrazolo[1,5-a]pyrimidin-6-yl)acetate (100 mg, 0.164 mmol) and 4-methoxy-4-methylpiperidine•HCl (54.3 mg, 0.328 mmol) in NMP (2 mL) was added DIEA (0.086 mL, 0.491 mmol) and the mixture was heated at 60° C. for 16 h. At this point LCMS indicated completion of reaction. Mixture was then cooled to room temp, diluted with water and extracted with ethyl acetate (2×50 mL), dried (Na2SO4), filtered and concentrated. The residue was then purified by flash chromatography (5-70% EtOAc/hexane) to afford (S)-ethyl 2-(tert-butoxy)-2-(2-((3-(4-fluorophenyl)-2-oxopropyl)carbamoyl)-7-(4-methoxy-4-methylpiperidin-1-yl)-5-methylpyrazolo[1,5-a]pyrimidin-6-yl)acetate (62 mg, 0.101 mmol, 61.9% yield) as off-white solid. $^1$H NMR (500 MHz, CDCl$_3$) δ 7.85 (br. s., 1H), 7.27-7.22 (m, 2H), 7.10-7.02 (m, 3H), 5.91 (br. s., 1H), 4.43 (dd, J=4.7, 1.6 Hz, 2H), 4.31-4.11 (m, 2H), 3.82 (s, 2H), 3.36 (s, 3H), 2.64 (s, 3H), 2.04-1.92 (m, 2H), 1.80-1.67 (m, 2H), 1.36 (br. s., 3H), 1.27-1.22 (m, 12H). four piperidine hydrogens missing. LCMS (M+H)=612.6.

Example 22

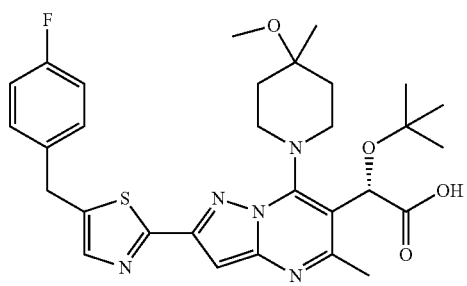 [SMILES: COC1(C)CCN(c2c([C@H](OC(C)(C)C)C(=O)O)c(C)nc3cc(-c4ncc(Cc5ccc(F)cc5)s4)nn23)CC1]

(S)-2-(tert-Butoxy)-2-(2-(5-(4-fluorobenzyl)thiazol-2-yl)-7-(4-methoxy-4-methylpiperidin-1-yl)-5-methylpyrazolo[1,5-a]pyrimidin-6-yl)acetic acid To a solution of (S)-ethyl 2-(tert-butoxy)-2-(2-((3-(4-fluorophenyl)-2-oxopropyl)carbamoyl)-7-(4-methoxy-4-methylpiperidin-1-yl)-5-methylpyrazolo[1,5-a]pyrimidin-6-yl)acetate (62 mg, 0.101 mmol) in toluene was added Lawesson's Reagent (45.1 mg, 0.111 mmol) and stirr for 15 min at rt, 1 h at 60° C. 2 h. At this point LCMS indicated completion of reaction and appearance of desired product. Mixture was then cooled, concentrated and treated with 1N NaOH (0.304 mL, 0.304 mmol) in MeOH (2 mL) at 65° C. for 4 h. Mixture was then cooled and purified by prep HPLC to afford (S)-2-(tert-butoxy)-2-(2-(5-(4-fluorobenzyl)thiazol-2-yl)-7-(4-methoxy-4-methylpiperidin-1-yl)-5-methylpyrazolo[1,5-a]pyrimidin-6-yl)acetic acid (39 mg, 0.067 mmol, 66.1% yield). $^1$H NMR (500 MHz, DMSO-d$_6$) δ 7.55 (s, 1H), 7.16 (dd, J=8.2, 5.8 Hz, 2H), 6.96 (t, J=8.9 Hz, 2H), 6.65 (s, 1H), 5.26 (br. s., 1H), 4.05 (s, 2H), 2.97 (s, 3H), 1.70 (s, 3H), 1.56 (d, J=8.2 Hz, 1H), 1.36 (br. s., 1H), 1.01 (s, 3H), 0.93 (s, 9H). 4 piperidine hydrogens are missing. LCMS (M+H)=482.5.

Intermediate 41

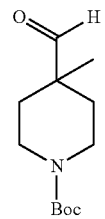 [SMILES: CC1(C=O)CCN(C(=O)OC(C)(C)C)CC1]

Ref: WO2008/118718 tert-Butyl 4-formyl-4-methylpiperidine-1-carboxylate

To a solution of tert-butyl 4-formylpiperidine-1-carboxylate (4.5 g, 21.10 mmol) in CH$_2$Cl$_2$ (50 mL) at 0° C. was added KOtBu (3.08 g, 27.4 mmol) followed by MeI (3.96 mL, 63.3 mmol) and the resulting mixture was stirred at 0° C. for 30 min, and then warmed to room temp and stirr for 1.5 h. The reaction mixture was then poured into brine and the mixture was extracted with dichloromethane, dried (Na$_2$SO$_4$), filtered and concentrated. The residue was then purified by Biotage (0-20% EtOAc/hexane) to afford tert-butyl 4-formyl-4-methylpiperidine-1-carboxylate (1.8 g, 7.92 mmol, 37.5% yield) as colorless oil. $^1$H NMR (500 MHz, CDCl$_3$) δ 9.48 (s, 1H), 3.71-3.66 (m, 2H), 3.19-3.05 (m, 2H), 1.93 (dt, J=13.7, 4.1 Hz, 2H), 1.47 (s, 9H), 1.46-1.37 (m, 2H), 1.10 (s, 3H). LCMS (M+H)=228.1.

Intermediate 42

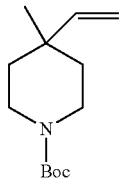 [SMILES: C=CC1(C)CCN(C(=O)OC(C)(C)C)CC1]

tert-Butyl 4-methyl-4-vinylpiperidine-1-carboxylate (Ref: U.S. Pat. No. 6,140,333): To a solution of CH$_3$PPh$_3$Br (1037 mg, 2.90 mmol) in THF (20 mL) at 0° C.

was added 2.5 M nBuLi (2.105 mL, 3.43 mmol) and the mixture was stirred for 30 min. tert-Butyl 4-formyl-4-methylpiperidine-1-carboxylate (600 mg, 2.64 mmol) in THF (5 mL) was added dropwise and the mixture was stirred for 1 h at 0° C. The reaction mixture was then diluted with ethyl acetate and washed with sat. NH$_4$Cl and brine, dried (Na$_2$SO$_4$), filtered and concentrated. The residue was then purified by Biotage (0-30% EtOAc/hexane) to afford tert-butyl 4-methyl-4-vinylpiperidine-1-carboxylate (310 mg, 1.376 mmol, 52.1% yield) as colorless liquid. $^1$H NMR (500 MHz, CDCl$_3$) δ 5.79 (dd, J=17.7, 10.9 Hz, 1H), 5.09-4.92 (m, 2H), 3.49 (ddd, J=13.4, 7.1, 3.9 Hz, 2H), 3.38-3.22 (m, 2H), 1.59 (ddd, J=13.0, 7.1, 3.5 Hz, 2H), 1.48 (s, 9H), 1.40 (ddd, J=13.2, 8.9, 3.9 Hz, 2H), 1.05 (s, 3H).

Intermediate 43

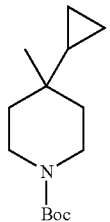

tert-Butyl 4-cyclopropyl-4-methylpiperidine-1-carboxylate

To a solution of tert-butyl 4-methyl-4-vinylpiperidine-1-carboxylate (310 mg, 1.376 mmol) in diethyl ether (10 mL) cooled to 0° C. was added Pd(OAc)$_2$ (15.44 mg, 0.069 mmol) followed by the freshly prepared ethereal CH$_2$N$_2$ solutions in portions, and the reaction mixture was stirred at room temp for 16 h. Mixture was then quenched with dropwise addition of AcOH and diluted with sat. NaHCO$_3$ solution. The mixture was extracted with CH$_2$Cl$_2$ and the organic layer was dried over Na$_2$SO$_4$. HNMR of the crude material indicates approx 20% of desired cyclopropyl product co-eluting with starting material. Used as is in the next step. $^1$H NMR (500 MHz, CDCl$_3$) δ 3.78-3.66 (m, 2H), 3.14 (ddd, J=13.6, 10.2, 3.5 Hz, 2H), 1.38-1.34 (m, 2H), 1.29-1.20 (m, 2H), 1.05 (s, 9H), 0.80 (s, 3H), 0.32-0.21 (m, 4H).

Intermediate 44 and 45

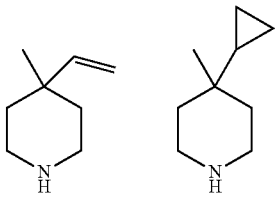

4-Methyl-4-vinylpiperidine, HCl and 4-cyclopropyl-4-methylpiperidine, HCl

A mixture of tert-butyl 4-methyl-4-vinylpiperidine-1-carboxylate (240 mg, 1.065 mmol) and tert-butyl 4-cyclopropyl-4-methylpiperidine-1-carboxylate (255 mg, 1.065 mmol) from step above and 4M HCl in dioxane (1.331 ml, 5.33 mmol) was stirred at room temp for 3 h. Mixture was then concentrated and the solids were triturated with ether/hexane, filtered and dried under high vac to afford 160 mg of mixture of vinyl and cyclopropyl amine. Used as is in the next step without further purification.

Example 23 and 24

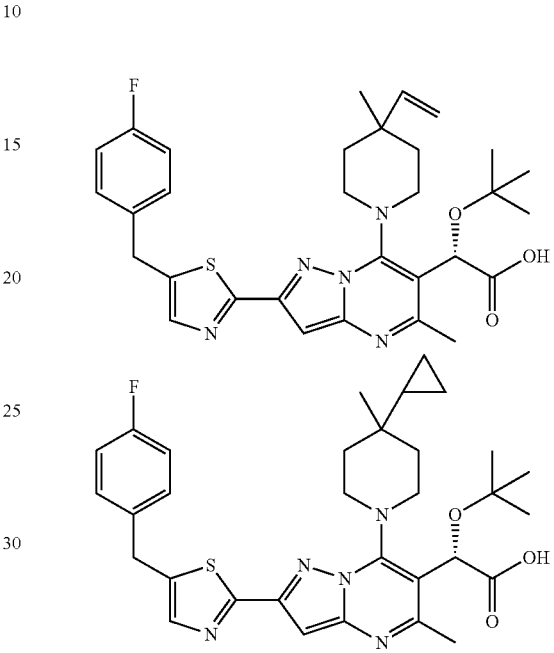

(S)-2-(tert-Butoxy)-2-(2-(5-(4-fluorobenzyl)thiazol-2-yl)-5-methyl-7-(4-methyl-4-vinylpiperidin-1-yl) pyrazolo[1,5-a]pyrimidin-6-yl)acetic acid and (S)-2-(tert-butoxy)-2-(7-(4-cyclopropyl-4-methylpiperidin-1-yl)-2-(5-(4-fluorobenzyl)thiazol-2-yl)-5-methylpyrazolo[1,5-a]pyrimidin-6-yl)acetic acid To a solution of (S)-ethyl 2-(tert-butoxy)-2-(2-((3-(4-fluorophenyl))-2-oxopropyl)carbamoyl)-7-iodo-5-methyl-pyrazolo[1,5-a]pyrimidin-6-yl)acetate (300 mg, 0.491 mmol) and mixture of vinyl and cyclopropyl 4-methyl piperidine 160 mg form step above in NMP (3 mL) was added DIEA (0.258 mL, 1.474 mmol) and the mixture was heated at 60° C. for 16 h. At this point LCMS indicates completion of reaction. Mixture was then cooled to room temp, diluted with water and extracted with ethyl acetate (2×50 mL), dried (Na$_2$SO$_4$), filtered and concentrated. The residue was then purified by flash chromatography (5-70% EtOAc/hexane) to afford approx 3:1 inseparable mixture of (S)-ethyl 2-(tert-butoxy)-2-(2-((3-(4-fluorophenyl))-2-oxopropyl)carbamoyl)-5-methyl-7-(4-methyl-4-vinylpiperidin-1-yl)pyrazolo[1,5-a]pyrimidin-6-yl)acetate LCMS (M+H)=608.4 and (S)-ethyl 2-(tert-butoxy)-2-(7-(4-cyclopropyl-4-methylpiperidin-1-yl)-2-((3-(4-fluorophenyl))-2-oxopropyl)carbamoyl)-5-methylpyrazolo[1,5-a]pyrimidin-6-yl)acetate. LCMS (M+H)=622.4, which was treated with Lawesson's Reagent (65.9 mg, 0.163 mmol) in in toluene (5 mL) at 60° C. for 1 h. Mixture was then concentrated and the crude was treated with 1M NaOH (0.592 mL, 0.592 mmol) in MeOH (3 mL) at 70° C. for 3 h. Mixture was then cooled to room temp and purified by prep HPLC to afford.

Example 23

(S)-2-(tert-Butoxy)-2-(2-(5-(4-fluorobenzyl)thiazol-2-yl)-5-methyl-7-(4-methyl-4-vinylpiperidin-1-yl)pyrazolo[1,5-a]pyrimidin-6-yl)acetic acid (50 mg, 0.087 mmol, 58.4% yield). $^1$H NMR (500 MHz, DMSO-$d_6$) δ 7.75 (s, 1H), 7.36 (d, J=6.1 Hz, 2H), 7.17 (t, J=8.2 Hz, 2H), 6.83 (s, 1H), 5.92 (dd, J=17.7, 10.7 Hz, 1H), 5.38 (br. s., 1H), 5.08 (d, J=16.5 Hz, 2H), 4.26 (s, 2H), 1.90 (s, 3H), 1.68 (br. s., 2H), 1.50 (br. s., 2H), 1.13 (br. s., 12H). 4 missing piperidine hydrogens. LCMS (M+H)=578.4.

Example 24

(S)-2-(tert-Butoxy)-2-(7-(4-cyclopropyl-4-methylpiperidin-1-yl)-2-(5-(4-fluorobenzyl)thiazol-2-yl)-5-methylpyrazolo[1,5-a]pyrimidin-6-yl)acetic acid (15 mg, 0.025 mmol, 17.12% yield). $^1$H NMR (500 MHz, DMSO-$d_6$) δ 7.75 (s, 1H), 7.41-7.29 (m, 2H), 7.16 (t, J=8.9 Hz, 2H), 6.84 (s, 1H), 5.41 (br. s., 1H), 4.25 (br. s., 2H), 1.90 (s, 3H), 1.66 (br. s., 1H), 1.46 (br. s., 2H), 1.31 (br. s., 1H), 1.14 (s, 9H), 0.98-0.94 (m, 4H), 0.30 (d, J=6.4 Hz, 4H). 4 missing piperidine hydrogens LCMS (M+H)=592.4.

Intermediate 46

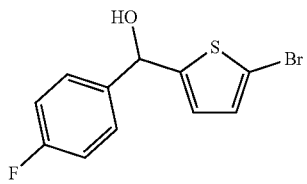 [SMILES: OC(c1ccc(F)cc1)c1ccc(Br)s1]

(5-Bromothiophen-2-yl)(4-fluorophenyl)methanol

To a solution of 5-bromothiophene-2-carbaldehyde (1 g, 5.23 mmol) in Diethyl ether (20 mL) at −15° C. was added dropwise 2M solution of (4-fluorophenyl)magnesium bromide (2.88 mL, 5.76 mmol). The mixture was allowed to warm to room temp and stirr for 1 h. Sat. NH$_4$Cl solution was then added and the mixture was extracted with ethyl acetate, dried (Na$_2$SO$_4$), filtered and concentrated. The residue was then purified on biotage (0-30% EtOAc/hexane) to afford (5-bromothiophen-2-yl)(4-fluorophenyl)methanol (900 mg, 3.13 mmol, 59.9% yield) as light yellow liquid. $^1$H NMR (500 MHz, CDCl$_3$) δ 7.45-7.39 (m, 2H), 7.11-7.05 (m, 2H), 6.91 (d, J=3.8 Hz, 1H), 6.64 (dd, J=3.8, 0.9 Hz, 1H), 5.97 (s, 1H), 2.45 (br. s., 1H), 1.60 (br. s., 1H).

Intermediate 47

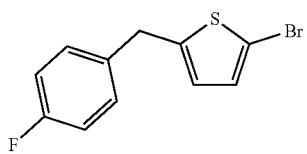

2-Bromo-5-(4-fluorobenzyl)thiophene

To a solution of (5-bromothiophen-2-yl)(4-fluorophenyl)methanol (900 mg, 3.13 mmol) and Et$_3$SiH (2.503 mL, 15.67 mmol) in chloroform (20 mL) at 0° C. was added dropwise triflic acid (0.557 mL, 6.27 mmol) and the resulting mixture was stirred at room temp for 1 h, then it was diluted with dichloromethane and washed with at.NaHCO$_3$ solution. The organic phase was dried (Na$_2$SO$_4$), filtered and concentrated. The residue was then purified by Biotage (0-20% EtOAc/hexane) to afford 2-bromo-5-(4-fluorobenzyl)thiophene (600 mg, 2.213 mmol, 70.6% yield) as colorless liquid. $^1$H NMR (500 MHz, CDCl$_3$) δ 7.24-7.18 (m, 2H), 7.06-6.99 (m, 2H), 6.89 (d, J=3.6 Hz, 1H), 6.57 (dt, J=3.7, 1.1 Hz, 1H), 4.07 (s, 2H).

Intermediate 48

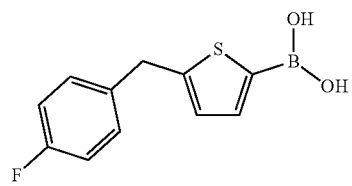 [SMILES: OB(O)c1ccc(Cc2ccc(F)cc2)s1]

(5-(4-Fluorobenzyl)thiophen-2-yl)boronic acid

To a solution of 2-bromo-5-(4-fluorobenzyl)thiophene (300 mg, 1.106 mmol) in THF (10 mL) at −78° C. was added dropwise 2.5M nBuLi (0.531 mL, 1.328 mmol) and the resulting mixture was stirred for 15 min. triisopropyl borate (1.526 mL, 6.64 mmol) was then added and the mixture was stirred for 2 h. Mixture was then warmed to room temp, acidified with 1N HCl and extracted with ether. The organic layer was dried (Na$_2$SO$_4$), filtered and concentrated under resuced pressure. The residue was then triturated with ethyl acetate/hexane and solids were filtered and dried under high vac to a foord (5-(4-fluorobenzyl)thiophen-2-yl)boronic acid (150 mg, 0.635 mmol, 57.4% yield) as off-white solid. $^1$H NMR (400 MHz, DMSO-$d_6$) δ 7.50 (d, J=3.3 Hz, 1H), 7.37-7.26 (m, 2H), 7.20-7.07 (m, 2H), 6.92 (d, J=3.3 Hz, 1H), 4.15 (s, 2H).

Example 25

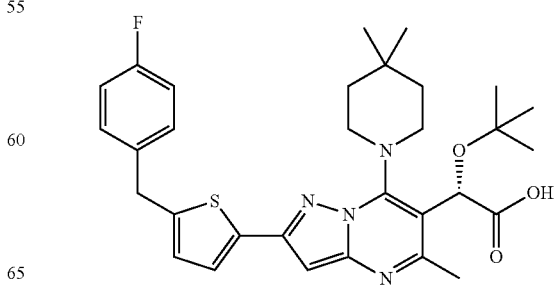

(S)-2-(tert-Butoxy)-2-(7-(4,4-dimethylpiperidin-1-yl)-2-(5-(4-fluorobenzyl)thiophen-2-yl)-5-methyl-pyrazolo[1,5-a]pyrimidin-6-yl)acetic acid A mixture of (S)-methyl 2-(2-bromo-7-(4,4-dimethylpiperidin-1-yl)-5-methylpyrazolo[1,5-a]pyrimidin-6-yl)-2-(tert-butoxy)acetate (50 mg, 0.107 mmol), (5-(4-fluorobenzyl)thiophen-2-yl)boronic acid (50.5 mg, 0.214 mmol) and 2M $Na_2CO_3$ (0.107 mL, 0.214 mmol) in DMF (2 mL) was degassed for 15 min. tetrakis(triphenylphosphine)palladium (0) (8.65 mg, 7.49 µmol) was then added and the degassing was continue for another 5 min. The mixture was then heated at 90° C. for 16 h. After cooling to room temp, water was added and the mixture was extracted with ethyl acetate, washed with brine, dried ($Na_2SO_4$), filtered and concentrated. The residue was then treated with 1M NaOH (0.321 mL, 0.321 mmol) in MeOH (3 mL) at 70° C. for 3 h. Mixture was then cooled and purified by prep HPLC to afford (S)-2-(tert-butoxy)-2-(7-(4,4-dimethylpiperidin-1-yl)-2-(5-(4-fluorobenzyl)thiophen-2-yl)-5-methylpyrazolo[1,5-a]pyrimidin-6-yl)acetic acid (24 mg, 0.042 mmol, 39.7% yield). $^1$H NMR (500 MHz, DMSO-$d_6$) δ 7.48 (br. s., 1H), 7.37-7.29 (m, 2H), 7.15 (t, J=8.4 Hz, 2H), 6.93 (br. s., 1H), 6.81 (br. s., 1H), 5.72 (br. s., 1H), 4.18 (br. s., 2H), 2.47 (s, 3H), 1.57 (br. s., 2H), 1.46 (br. s., 2H), 1.17 (s., 9H), 1.06 (s., 6H). Four missing piperideine hydrogens LCMS (M+H)=565.5.

Intermediate 49

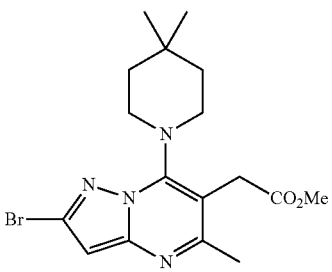 [SMILES: COC(=O)Cc1c(C)nc2cc(Br)nn2c1N1CCC(C)(C)CC1]

Methyl 2-(2-bromo-7-(4,4-dimethylpiperidin-1-yl)-5-methylpyrazolo[1,5-a]pyrimidin-6-yl)acetate To a solution of methyl 2-(2-bromo-7-chloro-5-methyl-pyrazolo[1,5-a]pyrimidin-6-yl)acetate (1.33 g, 4.18 mmol, 1 equiv) in DMF (14 mL) was added 4,4-dimethylpiperidine hydrochloride (0.75 g, 5.01 mmol, 1.2 equiv) and DIPEA (1.75 mL, 10.02 mmol, 2.4 equiv). The reaction was then heated in an oil bath at 60° C. Upon completion, the reaction was removed from heating, diluted with water, and extracted with EtOAc (×2). The combined EtOAc extracts were dried over $Na_2SO_4$ and concentrated in vacuo. The crude product was purified by silica gel flash chromatography (0-100% EtOAc/hexane) to provide the product as an off white solid (1.50 g, 91%). $^1$H NMR (400 MHz, CDCl$_3$) δ 6.53 (s, 1H), 3.80 (s, 2H), 3.77 (s, 3H), 3.41 (br. s., 4H), 2.51 (s, H), 1.54 (t, J=5.6 Hz, 4H), 1.09 (s, 6H); LCMS (ESI, M+1): 395.25.

Intermediate 50

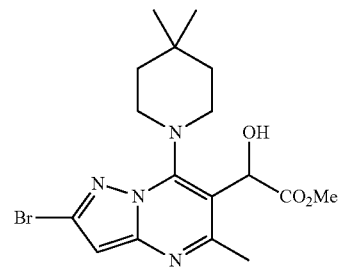

Methyl 2-(2-bromo-7-(4,4-dimethylpiperidin-1-yl)-5-methylpyrazolo[1,5-a]pyrimidin-6-yl)-2-hydroxyacetate To a solution of methyl 2-(2-bromo-7-(4,4-dimethylpiperidin-1-yl)-5-methylpyrazolo[1,5-a]pyrimidin-6-yl)acetate (1.49 g, 3.79 mmol, 1 equiv) in THF (38 mL) at −78° C. (IPA/$CO_2$) was added KHMDS (6.8 mL of a 0.91 M solution in THF, 6.07 mmol, 1.6 equiv). The reaction turned a deep orange color. After 15 min, 3-phenyl-2-(phenysulfonyl)-1,2-oxaziridine (1.49 g, 5.69 mmol, 1.5 equiv) was added in a single portion. The reaction solution significantly darkened and was then allowed to stir for 30 min. The reaction was then removed from the cooling bath and quenched with saturated aqueous solution of $NaHCO_3$, added to water, and extracted with EtOAc (×3). The combined EtOAc extracts were dried over $Na_2SO_4$ and concentrated in vacuo. The crude product was purified by silica gel flash chromatography (0-100% EtOAc/hexane) to provide the product as a waxy yellow solid (1.28 g, 82%). $^1$H NMR (400 MHz, CDCl3) δ 6.57 (s, 1H), 5.53 (d, J=5.3 Hz, 1H), 4.78 (br. s., 1H), 4.52 (d, J=5.3 Hz, 1H), 3.80 (s, 3H), 2.60 (s, 3H), 1.57-1.53 (m, J=3.8 Hz, 4H), 1.10 (s, 6H); LCMS (ESI, M+1): 411.2.

Intermediate 51

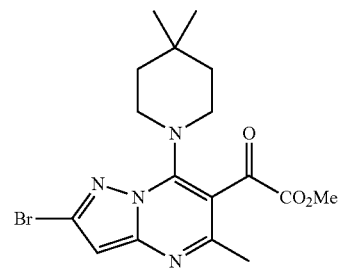 [SMILES: COC(=O)C(=O)c1c(C)nc2cc(Br)nn2c1N1CCC(C)(C)CC1]

Methyl 2-(2-bromo-7-(4,4-dimethylpiperidin-1-yl)-5-methylpyrazolo[1,5-a]pyrimidin-6-yl)-2-oxoacetate To a solution of methyl 2-(2-bromo-7-(4,4-dimethylpiperidin-1-yl)-5-methylpyrazolo[1,5-a]pyrimidin-6-yl)-2-hydroxyacetate (1.28 g, 3.11 mmol, 1 equiv) in DCM (16 mL) was added Dess-Martin periodindane (1.85 g, 4.36 mmol, 1.4 equiv). After 30 min, the reaction was added saturated aqueous NHCO₃ and extracted with DCM (×3). The combined DCM extracts were dried over Na₂SO₄ and concentrated in vacuo. The crude product was purified by silica gel flash chromatography (0-50% EtOAc/hexane) to provide the product as a yellow solid (0.71 g, 56%). ¹H NMR (400 MHz, CDCl3) δ 6.56 (s, 1H), 3.94 (s, 3H), 3.58-3.43 (m, 4H), 2.55 (s, 3H), 1.64-1.50 (m, 4H), 1.05 (s, 6H); LCMS (ESI, M+1): 409.2.

Intermediate 52

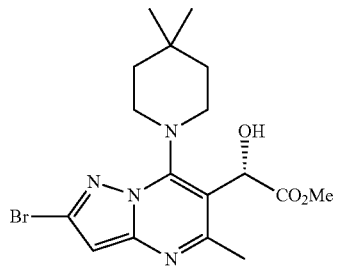 [SMILES: COC(=O)[C@@H](O)c1c(C)nc2cc(Br)nn2c1N1CCC(C)(C)CC1]

(S)-Methyl 2-(2-bromo-7-(4,4-dimethylpiperidin-1-yl)-5-methylpyrazolo[1,5-a]pyrimidin-6-yl)-2-hydroxyacetate To a solution of methyl 2-(2-bromo-7-(4,4-dimethylpiperidin-1-yl)-5-methylpyrazolo[1,5-a]pyrimidin-6-yl)-2-oxoacetate (6.15 g, 15.03 mmol, 1 equiv) in toluene (200 mL) was added (R)-1-methyl-3,3-diphenylhexahydropyrrolo[1,2-c][1,2,3]oxazaborole (9.0 mL of a 1 M solution in toluene, 9.02 mmol, 0.6 equiv). The solution was cooled to −25° C. (acetonitrile/CO₂) and catechol borane (8.7 mL of a 50% solution in toluene, 36.1 mmol, 2.4 equiv) was added. The cooling bath temperature was maintained between −15° C. and −25° C. for 4 h. The reaction was then diluted with EtOAc (35 mL) and 10% aqueous solution of K₂CO₃ (35 mL) and then allowed to warm to ambient temperature. The quenched solution was stirred for 45 min and then added to water. Extract with ether (×3). Combined ether extracts dried over MgSO₄ and concentrated in vacuo. The crude product was purified by silica gel flash chromatography (0-70% EtOAc/hexane) to provide the product as a pale yellow glass (5.68 g, 92%). ¹H NMR (500 MHz, CDCl3) δ 6.58 (s, 1H), 5.54 (d, J=5.2 Hz, 1H), 4.51 (d, J=5.0 Hz, 1H), 3.81 (s, 3H), 3.73-3.14 (m very broad, 4H), 2.62 (s, 3H), 1.60-1.54 (m, 4H), 1.11 (s, 6H); LCMS (ESI, M+1): 411.05.

Intermediate 53

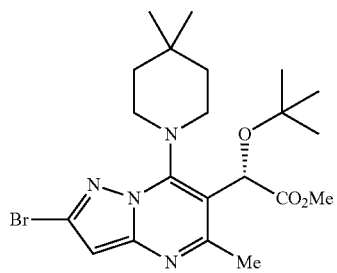 [SMILES: COC(=O)[C@@H](OC(C)(C)C)c1c(C)nc2cc(Br)nn2c1N1CCC(C)(C)CC1]

(S)-Methyl 2-(2-bromo-7-(4,4-dimethylpiperidin-1-yl)-5-methylpyrazolo[1,5-a]pyrimidin-6-yl)-2-(tert-butoxy)acetate To a solution of (S)-methyl 2-(2-bromo-7-(4,4-dimethylpiperidin-1-yl)-5-methylpyrazolo[1,5-a]pyrimidin-6-yl)-2-hydroxyacetate (5.68 g, 13.81 mmol, 1 equiv) in DCM (92 mL) and t-butyl acetate (184 mL) was added 70% perchloric acid (3.3 mL, 55.2 mmol, 4 equiv). The reaction turned pale yellow. After 3 h, the reaction was added very cautiously to a saturated aqueous solution of NaHCO₃ and extracted with CHCl₃ (×3). Combined organic extracts dried over Na₂SO₄ and concentrated in vacuo. The crude product was purified by silica gel flash chromatography (0-70% EtOAc/hexane) to provide the product as a pale yellow solid (2.8 g, 43%) and recovered starting material (3.0 g, 53%). ¹H NMR (400 MHz, CDCl3) δ 6.54 (s, 1H), 5.92 (s, 1H), 3.74 (s, 3H), 2.59 (s, 3H), 1.58 (s, 8H), 1.24 (s, 9H), 1.11 (s, 6H); LCMS (ESI, M+1):467.3.

Intermediate 54

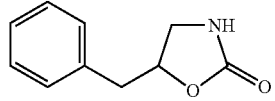 [SMILES: O=C1NCC(Cc2ccccc2)O1]

5-Benzyloxazolidin-2-one

Prepared according to the procedure described in U.S. Pat. No. 5,744,466

Intermediate 55

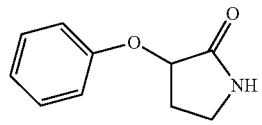 [SMILES: O=C1NCCC1Oc1ccccc1]

3-phenoxypyrrolidin-2-one

To a solution of phenol (0.279 g, 2.97 mmol, 1.2 equiv), 3-hydroxypyrrolidin-2-one (0.25 g, 2.47 mmol, 1 equiv), and triphenylphosphine (0.908 g, 3.46 mmol, 1.4 equiv) in THF (12 mL) was added DIAD (0.67 mL, 3.46 mmol, 1.4 equiv). After stirring 2 h, the reaction was complete by TLC and was concentrated in vacuo. The crude product was purified by flash column silica gel chromatography (0-100% EtOAc/hexane) to provide 3-phenoxypyrrolidin-2-one (0.116 g, 27%) as an off white solid. ¹H NMR (400 MHz, CDCl₃) δ 7.35-7.28 (m, 2H), 7.11-6.98 (m, 3H), 5.80 (br. s., 1H), 4.91-4.81 (m, 1H), 3.59-3.51 (m, 1H), 3.43 (dt, J=9.5, 7.3 Hz, 1H), 2.65 (dtd, J=13.4, 7.6, 3.8 Hz, 1H), 2.29 (ddt, J=13.5, 8.6, 6.8 Hz, 1H).

Intermediate 56

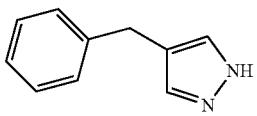 [SMILES: c1ccc(Cc2cn[nH]c2)cc1]

4-Benzyl-1H-pyrazole

Prepared according to the procedure described in Echevarria, A.; Elguero, J. *Syn. Comm.* 1993, 23, 925-930.

Intermediate 57

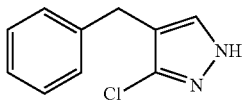 [SMILES: Clc1n[nH]cc1Cc1ccccc1]

4-Benzyl-3-chloro-1H-pyrazole

Prepared according to the procedure described in Echevarria, A.; Elguero, J. *Syn. Comm.* 1993, 23, 925-930.

Intermediate 58

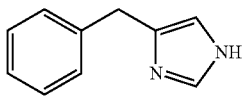 [SMILES: c1ccc(Cc2c[nH]cn2)cc1]

4-Benzyl-1H-imidazole

Prepared according to the procedure described in De Esch, I. J. P.; Gaffar, A.; Menge, W. M. P. V.; Timmerman, H. *Bioorg. Med. Chem.* 1999, 7, 3003-3009.

Intermediate 59

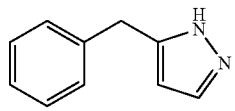 [SMILES: c1ccc(Cc2ccn[nH]2)cc1]

5-Benzyl-1H-pyrazole

Prepared according to the procedure described in Almirante, N.; Cerri, A.; Fedrizzi, G.; Marazzi, G.; Santagostino, M. *Tetrahedron Lett.* 1998, 39, 3287-3290

Intermediate 60

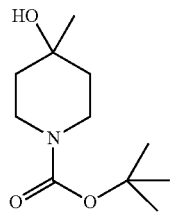

tert-Butyl 4-hydroxy-4-methylpiperidine-1-carboxylate

Under an N2 atmosphere, a 3N solution in ether of methylmagnesium bromide (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. aq. ammonium chloride. Another 20 mL of ether was added and the mixture was partitioned in a separatory funnel. The organic phase was set aside and the aqueous phase was extracted with another 20 mL of ether. The combined ether extracts were dried over MgSO$_4$, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90%) as a colorless oil. $^1$H NMR (400 MHz, CDCl$_3$) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

Intermediate 61

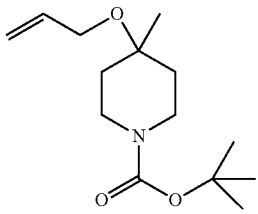 [SMILES: C=CCOC1(C)CCN(C(=O)OC(C)(C)C)CC1]

tert-Butyl 4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. aq. ammonium chloride. The reaction mixture was extracted with ether. The organic phase was dried over MgSO$_4$, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. $^1$H NMR (500 MHz, CDCl$_3$) δ

6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

Intermediate 62

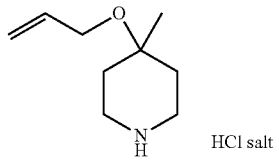

4-(Allyloxy)-4-methylpiperidine hydrogen chloride salt

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, CD$_3$OD) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

Intermediate 63

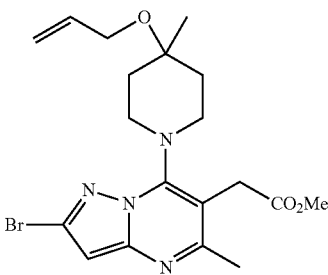 [SMILES: C=CCOC1(C)CCN(c2c(CC(=O)OC)c(C)nc3cc(Br)nn23)CC1]

Methyl 2-(7-(4-(allyloxy)-4-methylpiperidin-1-yl)-2-bromo-5-methylpyrazolo[1,5-a]pyrimidin-6-yl)acetate A solution of methyl 2-(2-bromo-7-chloro-5-methylpyrazolo[1,5-a]pyrimidin-6-yl)acetate (13.4 g, 41.9 mmol, 1 equiv), 4-(allyloxy)-4-methylpiperidine (7.16 g, 46.1 mmol, 1.1 equiv), and DIPEA (17.6 mL, 101 mmol, 2.4 equiv) in DMF (84 mL) was heated at 60° C. for 2 h. The reaction was then added to water and extracted with ether (×2). Combined ether extracts dried (MgSO$_4$) and concentrated in vacuo. The crude product was purified via silica gel flash chromatography (0-50% EtOAc/hex) to provide methyl 2-(7-(4-(allyloxy)-4-methylpiperidin-1-yl)-2-bromo-5-methylpyrazolo[1,5-a]pyrimidin-6-yl)acetate (17.7 g, 97%). $^1$H NMR (500 MHz, CDCl3) δ 6.52 (s, 1H), 6.02 (ddt, J=17.2, 10.4, 5.2 Hz, 1H), 5.43 (dd, J=17.2, 1.6 Hz, 1H), 5.22 (dq, J=10.4, 1.5 Hz, 1H), 3.99 (dt, J=5.2, 1.6 Hz, 2H), 3.77 (s, 3H), 3.79-3.76 (m, 2H), 3.70-3.56 (m, J=7.4 Hz, 2H), 3.33 (br. s., 2H), 2.50 (s, 3H), 1.97-1.89 (m, 2H), 1.87-1.78 (m, J=9.3 Hz, 2H), 1.32 (s, 3H); LCMS (ESI, M+1): 437.20.

Intermediate 64

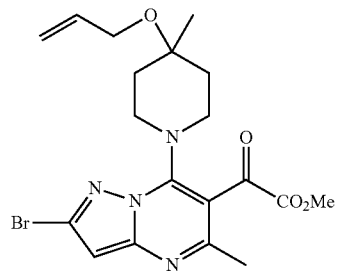 [SMILES: C=CCOC1(C)CCN(c2c(C(=O)C(=O)OC)c(C)nc3cc(Br)nn23)CC1]

Methyl 2-(7-(4-(allyloxy)-4-methylpiperidin-1-yl)-2-bromo-5-methylpyrazolo[1,5-a]pyrimidin-6-yl)-2-oxoacetate A solution of methyl 2-(7-(4-(allyloxy)-4-methylpiperidin-1-yl)-2-bromo-5-methylpyrazolo[1,5-a]pyrimidin-6-yl)acetate (17.7 g, 40.5 mmol, 1 equiv) in THF (200 mL) was cooled to −78° C. (IPA/CO$_2$). KHMDS (72 mL of a 0.91 M solution in THF, 64.9 mmol, 1.6 equiv) was added dropwise over ~2 min. Reaction turned a deep orange color. After 30 min, 3-phenyl-2-(phenylsulfonyl)-1,2-oxaziridine (15.9 g, 60.8 mmol, 1.2 equiv) was added in a single portion. The reaction significantly darkened. After 30 min, the reaction was added to saturated aqueous sodium bicarbonate and extracted with ether (×2). The combined ether extracts were dried (MgSO$_4$) and concentrated in vacuo to provide the crude product as a brown oil. This was taken up in DCM (200 mL) and Dess-Martin periodinane (20.6 g, 48.6 mmol, 1.2 equiv). After 30 min, the reaction was added to saturated aqueous sodium bicarbonate and extracted with DCM (×3). Combined DCM extracts were dried (Na$_2$SO$_4$) and concentrated in vacuo to provide the crude product. The crude product was purified via silica gel flash chromatography (0-50% EtOAc/hex) to provide methyl 2-(7-(4-(allyloxy)-4-methylpiperidin-1-yl)-2-bromo-5-methylpyrazolo[1,5-a]pyrimidin-6-yl)-2-oxoacetate (9.2 g, 50%). 1H NMR (500 MHz, CDCl$_3$) δ 6.55 (s, 1H), 6.07-5.87 (m, 1H), 5.38 (dq, J=17.2, 1.7 Hz, 1H), 5.20 (dq, J=10.4, 1.6 Hz, 1H), 3.95-3.92 (m, 5H), 3.69 (d, J=12.6 Hz, 2H), 3.59-3.50 (m, 2H), 2.56 (s, 3H), 1.96-1.82 (m, 4H), 1.28 (s, 3H); LCMS (ESI, M+1): 450.95.

Intermediate 65

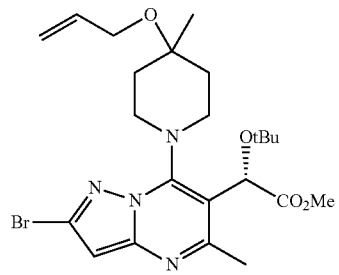 [SMILES: C=CCOC1(C)CCN(c2c([C@H](OC(C)(C)C)C(=O)OC)c(C)nc3cc(Br)nn23)CC1]

(S)-Methyl 2-(7-(4-(allyloxy)-4-methylpiperidin-1-yl)-2-bromo-5-methylpyrazolo[1,5-a]pyrimidin-6-yl)-2-(tert-butoxy)acetate A solution of methyl 2-(7-(4-(allyloxy)-4-methylpiperidin-1-yl)-2-bromo-5-methylpyrazolo[1,5-a]pyrimidin-6-yl)-2-oxoacetate (9.20 g, 20.3 mmol, 1 equiv) and (R)-1-methyl-3,3-diphenylhexahydropyrrolo[1,2-c][1,3,2]oxazaborole (12.2 mL of a 1 M solution in toluene, 12.2 mmol, 0.6 equiv) in toluene (200 mL) was cooled to −25° C. (MeCN/CO$_2$). Catecholborane (6.8 mL of a 50% solution in toluene, 28.4 mmol, 1.4 equiv) was then added and temperature was held between −15° C. and −25° C. for 18 h. At this point, more and (R)-1-methyl-3,3-diphenylhexahydropyrrolo[1,2-c][1,3,2]oxazaborole (4 mL of a 1 M solution in toluene, 4 mmol, 0.2 equiv) and catecholborane (3 mL of a 50% solution in toluene, 12.5 mmol, 0.6 equiv) were added. The reaction was then stirred a further 4 h. The reaction was then quenched with 10% aqueous K$_2$CO$_3$ (100 mL) and EtOAc (100 mL) and removed from cooling bath. After stirring 45 min, the mixture was added to water and extracted with ether (×4). The combined ether extracts were dried (MgSO$_4$) and concentrated in vacuo to provide the crude product as a yellow foam. This was taken up in DCM (50 mL) and tBuOAc (150 mL). To this solution was added perchloric acid (3.7 mL of a 70% aqueous solution, 60.9 mmol, 3 equiv) to give a cloudy orange solution. After stirring 3 h, the reaction was added cautiously to saturated aqueous sodium bicarbonate and extracted with DCM (×3). The combined DCM extracts were dried (Na$_2$SO$_4$) and concentrated in vacuo to provide the crude product. The crude product was purified via silica gel flash chromatography (0-100% EtOAc/hex) to provide (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (3.56 g, 34%) $^1$H NMR (500 MHz, CDCl$_3$) δ 6.54 (s, 1H), 6.09-5.97 (m, 1H), 5.83 (br. s., 1H), 5.48 (d, J=17.8 Hz, 1H), 5.24 (d, J=9.8 Hz, 1H), 4.50-3.00 (very broad m, 4H), 4.05-3.98 (m, 2H), 3.76 (s, 3H), 2.59 (s, 3H), 2.04-1.90 (m, 2H), 1.36 (s, 3H), 1.24 (s, 9H); LCMS (ESI, M+1): 509.09.

And recovered (S)-Methyl 2-(7-(4-(allyloxy)-4-methylpiperidin-1-yl)-2-bromo-5-methylpyrazolo[1,5-a]pyrimidin-6-yl)-2-hydroxyacetate (4.53 g, 49%). $^1$H NMR (500 MHz, CDCl3) δ 6.57 (s, 1H), 6.12-5.97 (m, 1H), 5.56-5.47 (m, 2H), 5.28-5.22 (m, 2H), 4.50-3.00 (very broad m, 4H), 4.00 (dt, J=5.0, 1.6 Hz, 2H), 3.82 (s, 3H), 2.59 (s, 3H), 2.01-1.91 (m, 2H), 1.80 (d, J=11.7 Hz, 2H), 1.33 (s, 3H); LCMS (ESI, M+1): 453.00.

Example 26

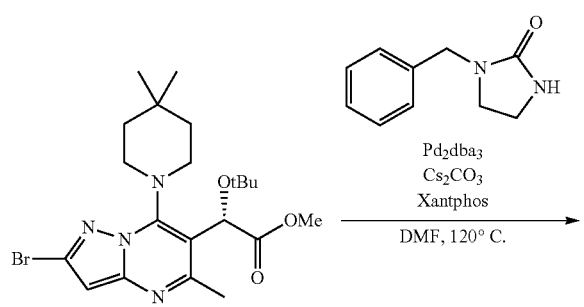

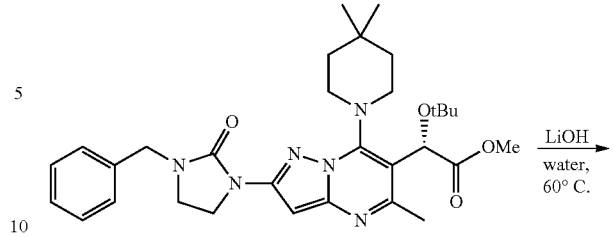

(S)-2-(2-(3-Benzyl-2-oxoimidazolidin-1-yl)-7-(4,4-dimethylpiperidin-1-yl)-5-methylpyrazolo[1,5-a]pyrimidin-6-yl)-2-(tert-butoxy)acetic acid A solution of (S)-methyl 2-(2-bromo-7-(4,4-dimethylpiperidin-1-yl)-5-methylpyrazolo[1,5-a]pyrimidin-6-yl)-2-(tert-butoxy)acetate (0.041 g, 0.088 mmol, 1 equiv), 1-benzylimidazolidin-2-one (0.022 g, 0.123 mmol, 1.4 equiv), Xantphos (0.006 g, 0.011 mmol, 0.12 equiv), Cs$_2$CO$_3$ (0.046 g, 0.140 mmol, 1.6 equiv), and Pd$_2$(dba)$_3$ (0.004 g, 0.004 mmol, 0.05 equiv) in DMF (0.9 mL) was heated at 120° C. for 1 h. The temperature was then lowered to 60° C. and MeOH (~1 mL) and LiOH.H$_2$O (0.074 g, 1.75 mmol, 20 equiv) were added. After 1 h, the reaction was allowed to cool to ambient temperature, filtered, and purified directly via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B; Flow: 20 mL/min, to provide the product (0.031 g, 64%). $^1$H NMR (500 MHz, DMSO-d$_6$) δ 7.43-7.25 (m, 5H), 6.67 (s, 1H), 5.67 (s, 1H), 4.43 (br. s., 2H), 3.99-3.91 (m, J=4.0 Hz, 2H), 2.55 (s, 3H), 1.57 (br. s., 2H), 1.45 (br. s., 2H), 1.16 (s, 9H), 1.04 (s, 6H) [note: some alkyl protons apparently obscured by water peak]; LCMS (ESI, M+1): 549.7.

The following compounds were prepared according to the above procedure using appropriate heterocycle.

Example 27

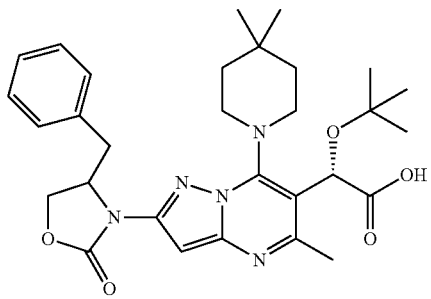 [SMILES: Cc1nc2cc(N3C(=O)OCC3Cc3ccccc3)nn2c(N2CCC(C)(C)CC2)c1[C@H](OC(C)(C)C)C(=O)O]

(2S)-2-(2-(4-Benzyl-2-oxooxazolidin-3-yl)-7-(4,4-dimethylpiperidin-1-yl)-5-methylpyrazolo[1,5-a]pyrimidin-6-yl)-2-(tert-butoxy)acetic acid, 1$^{st}$ diastereomer $^1$H NMR (500 MHz, DMSO-d$_6$) δ 7.34-7.10 (m, 5H), 6.66 (s, 1H), 5.68 (br. s., 1H), 4.95 (br. s., 1H), 4.50 (t, J=8.4 Hz, 1H), 4.32-4.22 (m, 1H), 3.58-3.16 (m, 6H), 2.55 (s, 3H), 1.59 (br. s., 2H), 1.48 (br. s., 2H), 1.18 (s, 9H), 1.03 (s, 6H) [note: 6 protons appear to be under water peak and are simply listed as a multiplet]; LCMS (ESI, M+1): 550.5.

Example 28

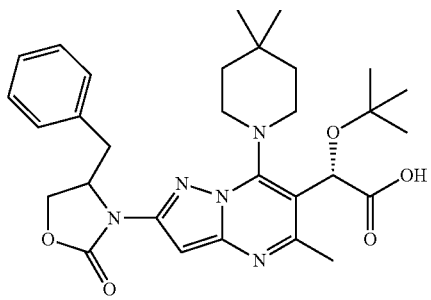 [SMILES: Cc1nc2cc(N3C(=O)OCC3Cc3ccccc3)nn2c(N2CCC(C)(C)CC2)c1[C@H](OC(C)(C)C)C(=O)O]

(2S)-2-(2-(4-Benzyl-2-oxooxazolidin-3-yl)-7-(4,4-dimethylpiperidin-1-yl)-5-methylpyrazolo[1,5-a]pyrimidin-6-yl)-2-(tert-butoxy)acetic acid, 2nd diastereomer $^1$H NMR (500 MHz, DMSO-d$_6$) δ 7.33-7.17 (m, 5H), 6.66 (s, 1H), 5.66 (s, 1H), 4.94 (br. s., 1H), 4.50 (t, J=8.2 Hz, 1H), 4.30-4.24 (m, 1H), 3.50-3.10 (m, 4H), 3.18-3.10 (m, 2H), 2.55 (s, 3H), 1.58 (br. s., 2H), 1.48 (br. s., 2H), 1.17 (s, 9H), 1.05 (br. s., 6H) [note: 4 protons appear to be under water peak and are simply listed as a multiplet]; LCMS (ESI, M+1): 550.5.

Example 29

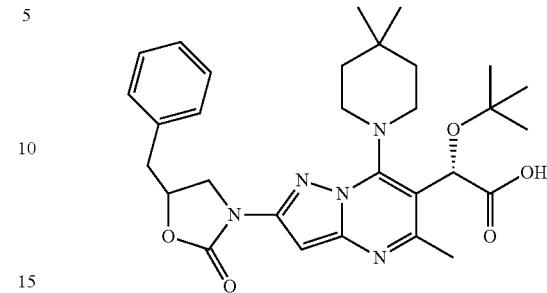

(2S)-2-(2-(5-Benzyl-2-oxooxazolidin-3-yl)-7-(4,4-dimethylpiperidin-1-yl)-5-methylpyrazolo[1,5-a]pyrimidin-6-yl)-2-(tert-butoxy)acetic acid, 1$^{st}$ diastereomer $^1$H NMR (500 MHz, DMSO-d$_6$) δ 7.40-7.20 (m, 5H), 6.55 (s, 1H), 5.60 (br. s., 1H), 5.09-4.96 (m, 1H), 4.18 (t, J=9.0 Hz, 1H), 3.90 (t, J=8.1 Hz, 1H), 3.13 (d, J=6.1 Hz, 1H), 2.48 (s, 3H), 1.56 (br. s., 2H), 1.44 (br. s., 2H), 1.15 (s, 9H), 1.03 (s, 6H) [note: 4 H from piperidine and 1 H from oxazolidinone not observed; presumably these are under water peak]; LCMS (ESI, M+1): 550.6.

Example 30

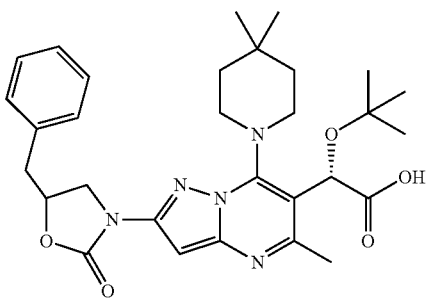 [SMILES: Cc1nc2cc(N3CC(Cc4ccccc4)OC3=O)nn2c(N2CCC(C)(C)CC2)c1[C@H](OC(C)(C)C)C(=O)O]

(2S)-2-(2-(5-Benzyl-2-oxooxazolidin-3-yl)-7-(4,4-dimethylpiperidin-1-yl)-5-methylpyrazolo[1,5-a]pyrimidin-6-yl)-2-(tert-butoxy)acetic acid, 2nd diastereomer $^1$H NMR (500 MHz, DMSO-d$_6$) δ 7.37-7.24 (m, 5H), 6.55 (s, 1H), 5.60 (br. s., 1H), 5.11-4.97 (m, 1H), 4.29-4.16 (m, 1H), 3.93-3.84 (m, 1H), 3.15-3.11 (m, 1H), 2.48 (s, 3H), 1.57 (br. s., 2H), 1.44 (br. s., 2H), 1.15 (s, 9H), 1.03 (s, 6H) [note: 4 H from piperidine and 1 H from oxazolidinone not observed; presumably these are under water peak]; LCMS (ESI, M+1): 550.5.

Example 31

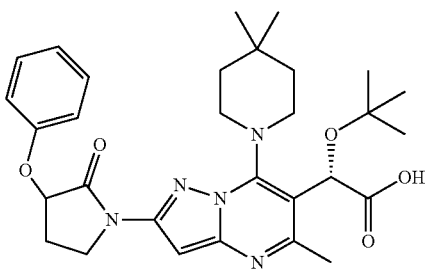 [SMILES: Cc1nc2cc(N3CCC(Oc4ccccc4)C3=O)nn2c(N2CCC(C)(C)CC2)c1[C@H](OC(C)(C)C)C(=O)O]

(2S)-2-(tert-Butoxy)-2-(7-(4,4-dimethylpiperidin-1-yl)-5-methyl-2-(2-oxo-3-phenoxypyrrolidin-1-yl)pyrazolo[1,5-a]pyrimidin-6-yl)acetic acid, 1$^{st}$ diastereomer 1H NMR (500 MHz, DMSO-$d_6$) δ 7.33 (br. s., 2H), 7.08 (d, J=7.6 Hz, 2H), 7.00 (br. s., 1H), 6.86 (br. s., 1H), 5.65 (br. s., 1H), 5.33 (br. s., 1H), 4.12 (br. s., 1H), 3.90 (br. s., 2H), 1.58 (br. s., 2H), 1.47 (br. s., 2H), 1.16 (br. s., 9H), 1.06 (br. s., 6H) [note: 1 H of oxazolidinone, 4 H of piperidine, and 3 H of pyridyl methyl not observed; presumably these are either very broad or under the water peak]; LCMS (ESI, M+1): 550.7.

Example 32

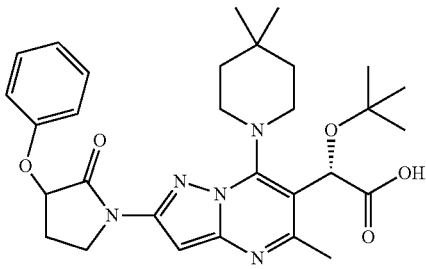 [SMILES: Cc1nc2cc(N3CCC(Oc4ccccc4)C3=O)nn2c(N2CCC(C)(C)CC2)c1[C@H](OC(C)(C)C)C(=O)O]

(2S)-2-(tert-Butoxy)-2-(7-(4,4-dimethylpiperidin-1-yl)-5-methyl-2-(2-oxo-3-phenoxypyrrolidin-1-yl)pyrazolo[1,5-a]pyrimidin-6-yl)acetic acid, 2nd diastereomer 1H NMR (500 MHz, DMSO-$d_6$) δ 7.32 (d, J=7.9 Hz, 2H), 7.12-6.95 (m, 3H), 6.85 (br. s., 1H), 5.65 (br. s., 1H), 5.40-5.25 (m, 1H), 4.11 (br. s., 1H), 3.90 (br. s., 1H), 2.84-2.72 (m, 1H), 2.17 (br. s., 1H), 1.59 (br. s., 2H), 1.46 (br. s., 2H), 1.16 (br. s., 9H), 1.06 (br. s., 6H) [note: 4 H of piperidine and 3 H of pyridyl methyl not observed; presumably these are either very broad or under the water peak]; LCMS (ESI, M+1): 550.6.

Example 33

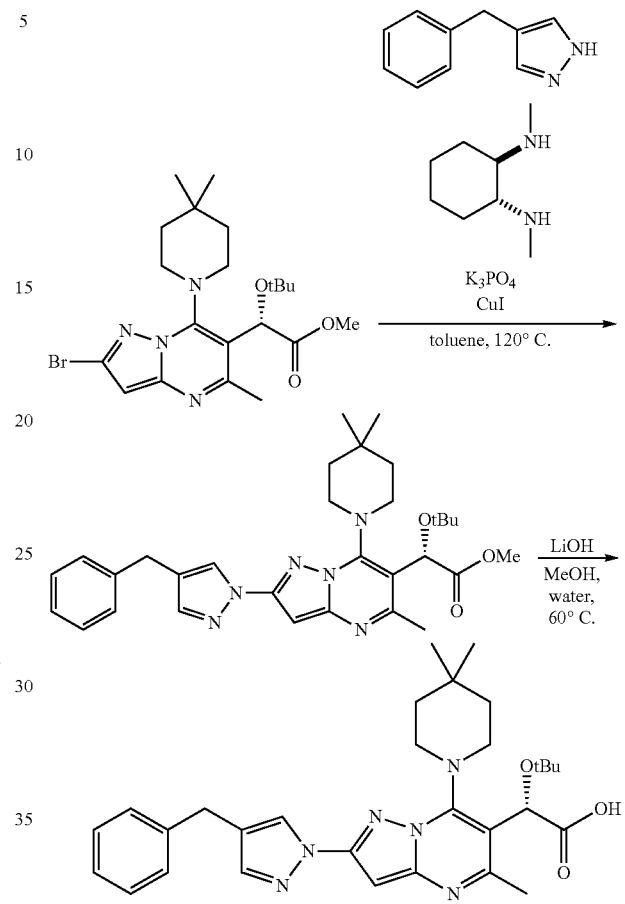

(S)-2-(2-(4-Benzyl-1H-pyrazol-1-yl)-7-(4,4-dimethylpiperidin-1-yl)-5-methylpyrazolo[1,5-a]pyrimidin-6-yl)-2-(tert-butoxy)acetic acid

[Procedure based on Buchwald et al. *J. Org. Chem.* 2004, 69, 5578-5587]. A solution of (S)-methyl 2-(2-bromo-7-(4,4-dimethylpiperidin-1-yl)-5-methylpyrazolo[1,5-a]pyrimidin-6-yl)-2-(tert-butoxy)acetate (0.112 g, 0.240 mmol, 1 equiv), 4-benzyl-1H-pyrazole (0.076 g, 0.479 mmol, 2 equiv), CuI (0.005 g, 0.024 mmol, 0.1 equiv), $K_3PO_4$ (0.132 g, 0.623 mmol, 2.6 equiv), and N1,N2-dimethylcyclohexane-1,2-diamine (0.008 mL, 0.048 mmol, 0.2 equiv) in toluene (1.2 mL) was heated at 120° C. for 40 h. The reaction was allowed to cool to ambient temperature and then purified directly by silica gel flash chromatography (0-30% EtOAc/hexane) to provide the product as a viscous yellow oil (0.031 g, 24%). $^1$H NMR (400 MHz, CDCl3) δ 8.03 (s, 1H), 7.61 (s, 1H), 7.37-7.25 (m, 5H), 6.74 (s, 1H), 5.97 (s, 1H), 3.95 (s, 2H), 3.74 (s, 3H), 2.61 (s, 3H), 1.58 (s, 4H), 1.25 (s, 9H), 1.11 (s, 6H)[note: 4 H of piperidine appear to be very broad and so not seen]; LCMS (ESI, M+1): 545.5.

To a solution of (S)-methyl 2-(2-(4-benzyl-1H-pyrazol-1-yl)-7-(4,4-dimethylpiperidin-1-yl)-5-methylpyrazolo[1,5-a]pyrimidin-6-yl)-2-(tert-butoxy)acetate (0.031 g, 0.057 mmol, 1 equiv) in 9:1 MeOH:water (0.60 ml) was added LiOH.$H_2O$ (0.024 g, 0.569 mmol, 10 equiv). The reaction was heated at 60° C. for 1.5 h. The reaction was then allowed to cool to ambient temperature, filtered, and purified directly via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 20-100% B over 20 minutes, then a 5-minute hold at 100% B; Flow: 20 mL/min, to provide the product (0.0324 g, 107%). $^1$H NMR (500 MHz, DMSO-$d_6$) δ 8.16 (s, 1H), 7.67 (s, 1H), 7.33-7.27 (m, 4H), 7.21 (br. s., 1H), 6.60 (s, 1H), 5.68-5.32 (m, 1H), 3.90 (s, 2H), 1.58 (br. s., 2H), 1.46 (br. s., 2H), 1.16 (br. s., 9H), 1.06 (br. s., 6H) [note: 4 H of piperidine and 3 H of pyrimydl methyl not observed; presumably these are under water peak and DMSO peak respectively]; LCMS (ESI, M+1): 531.5.

The following examples were prepared according to the above procedure using appropriate heterocycle Example 34

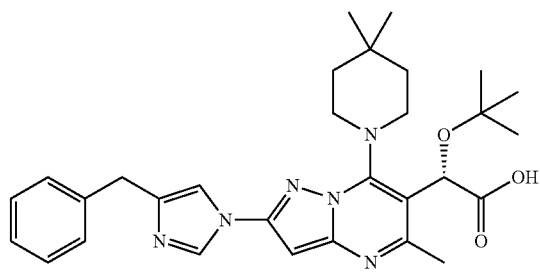 [SMILES: Cc1nc2cc(-n3cnc(Cc4ccccc4)c3)nn2c(N2CCC(C)(C)CC2)c1[C@H](OC(C)(C)C)C(=O)O]

(S)-2-(2-(4-Benzyl-1H-imidazol-1-yl)-7-(4,4-dimethylpiperidin-1-yl)-5-methylpyrazolo[1,5-a]pyrimidin-6-yl)-2-(tert-butoxy)acetic acid $^1$H NMR (500 MHz, DMSO-$d_6$) δ 7.35-7.15 (m, 6H), 6.85-6.67 (m, 1H), 5.62-5.32 (m, 1H), 1.64-1.34 (m, 4H), 1.14 (s, 9H), 1.00 (s, 6H) [note: 4H of piperidine, 3H pyridyl methyl, and 2H of benzyl group not observed; NMR sample very dilute); LCMS (ESI, M+1): 531.6.

Example 35

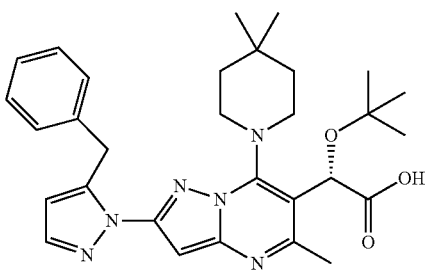 [SMILES: Cc1nc2cc(-n3nccc3Cc3ccccc3)nn2c(N2CCC(C)(C)CC2)c1[C@H](OC(C)(C)C)C(=O)O]

(S)-2-(2-(5 Benzyl-1H-pyrazol-1-yl)-7-(4,4-dimethylpiperidin-1-yl)-5-methylpyrazolo[1,5-a]pyrimidin-6-yl)-2-(tert-butoxy)acetic acid $^1$H NMR (500 MHz, DMSO-$d_6$) δ 8.33-8.19 (m, 1H), 7.37-7.27 (m, 4H), 7.24-7.14 (m, 1H), 6.69-6.55 (m, 1H), 6.41-6.26 (m, 1H), 5.77-5.53 (m, 1H), 4.07-3.95 (m, 2H), 1.67-1.55 (m, 2H), 1.52-1.41 (m, 2H), 1.16 (br. s., 9H), 1.05 (br. s., 6H) [note: pyridyl mehyl and 4H of piperidine not observed; likely under large water peak]; LCMS (ESI, M+1): 531.6.

Example 36

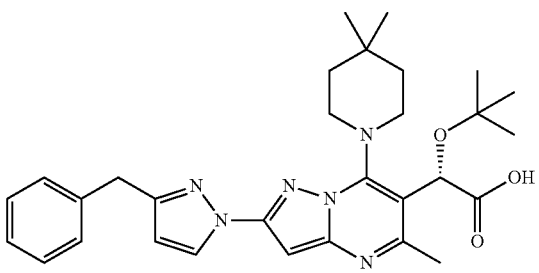 [SMILES: Cc1nc2cc(-n3ccc(Cc4ccccc4)n3)nn2c(N2CCC(C)(C)CC2)c1[C@H](OC(C)(C)C)C(=O)O]

(S)-2-(2-(3-Benzyl-1H-pyrazol-1-yl)-7-(4,4-dimethylpiperidin-1-yl)-5-methylpyrazolo[1,5-a]pyrimidin-6-yl)-2-(tert-butoxy)acetic acid $^1$H NMR (400 MHz, CD$_3$OD) δ 7.74-7.53 (m, 1H), 7.30-7.13 (m, 5H), 6.68-6.62 (m, 1H), 6.16-6.09 (m, 1H), 5.78-5.69 (m, 1H), 4.68-4.56 (m, 3H), 2.65-2.61 (m, 2H), 1.65-1.56 (m, 1H), 1.56-1.55 (m, 2H), 1.54-1.45 (m, 2H), 1.24 (s, 9H), 1.01 (s, 6H) [note: 4H of piperidine not observed; likely very broad]; LCMS (ESI, M+1): 531.6.

Example 37

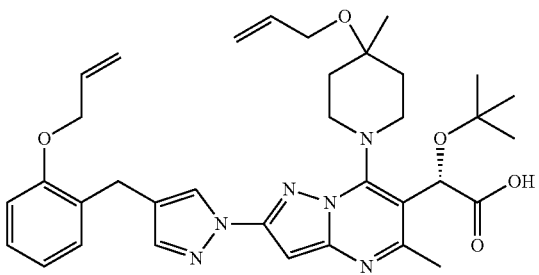 [SMILES: C=CCOc1ccccc1Cc1cnn(-c2cc3nc(C)c([C@H](OC(C)(C)C)C(=O)O)c(N4CCC(C)(OCC=C)CC4)n3n2)c1]

(S)-2-(7-(4-(Allyloxy)-4-methylpiperidin-1-yl)-2-(4-(2-(allyloxy)benzyl)-1H-pyrazol-1-yl)-5-methylpyrazolo[1,5-a]pyrimidin-6-yl)-2-(tert-butoxy)acetic acid $^1$H NMR (500 MHz, DMSO-$d_6$) δ 8.08 (br. s., 1H), 7.65 (br. s., 1H), 7.20 (d, J=7.3 Hz, 2H), 7.03-6.83 (m, 2H), 6.58 (br. s., 1H), 6.14-5.91 (m, 2H), 5.66-5.51 (m, 1H), 5.51-5.32 (m, 2H), 5.26 (d, J=9.2 Hz, 1H), 5.10 (d, J=9.5 Hz, 1H), 4.61 (br. s., 2H), 3.96 (br. s., 2H), 3.85 (br. s., 2H), 2.03-1.78 (m, 3H), 1.60 (br. s., 1H), 1.26 (br. s., 3H), 1.15 (br. s., 9H) [note: 4H of piperidine and 3H of pyridyl methyl not observed, piperidine 4H are likely very broad and methl is likely under DMSO peak]; LCMS (ESI, M+1): 629.7.

Example 38

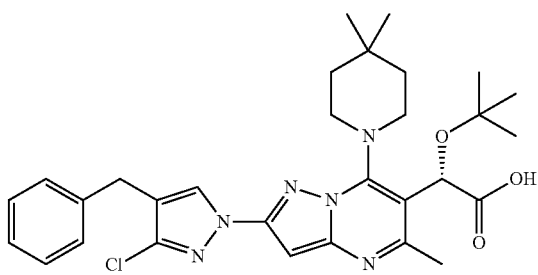 [SMILES: Cc1nc2cc(-n3cc(Cc4ccccc4)c(Cl)n3)nn2c(N2CCC(C)(C)CC2)c1[C@H](OC(C)(C)C)C(=O)O]

(S)-2-(2-(4-Benzyl-3-chloro-1H-pyrazol-1-yl)-7-(4,4-dimethylpiperidin-1-yl)-5-methylpyrazolo[1,5-a]pyrimidin-6-yl)-2-(tert-butoxy)acetic acid $^1$H NMR (500 MHz, DMSO-$d_6$) δ 8.29 (br. s., 1H), 7.37-7.19 (m, 5H), 6.64 (br. s., 1H), 5.60 (br. s., 1H), 3.87 (br. s., 2H), 1.68-1.40 (m, 4H), 1.16 (br. s., 9H), 1.05 (br. s., 6H) [note: 4H of piperidine and 3H of pyridyl methyl not observed, piperidine 4H are likely very broad and methl is likely under DMSO peak]; LCMS (ESI, M+1): 565.5.

Example 39

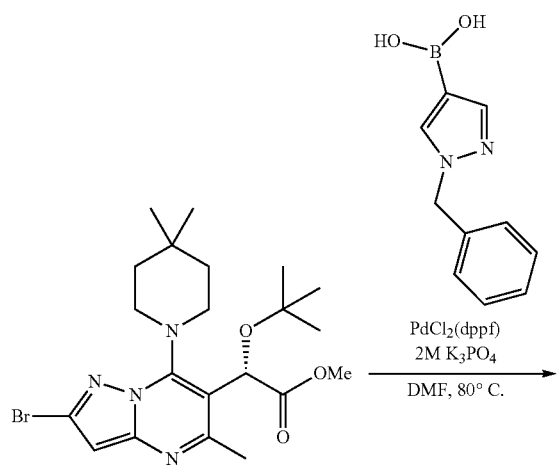

(S)-2-(2-(1-Benzyl-1H-pyrazol-4-yl)-7-(4,4-dimethylpiperidin-1-yl)-5-methylpyrazolo[1,5-a]pyrimidin-6-yl)-2-(tert-butoxy)acetic acid A solution of (S)-methyl 2-(2-bromo-7-(4,4-dimethylpiperidin-1-yl)-5-methylpyrazolo[1,5-a]pyrimidin-6-yl)-2-(tert-butoxy)acetate (0.030 g, 0.064 mmol, 1 equiv), (1-benzyl-1H-pyrazol-4-yl)boronic acid (0.039 g, 0.193 mmol, 3 equiv), PdCl$_2$(dppf) (0.005 g, 0.006 mmol, 0.1 equiv), and K$_3$PO$_4$ (0.16 mL of a 2 M aqueous solution, 0.321 mmol, 5 equiv) in DMF (0.3 mL) was sparged with nitrogen for 2 min. The reaction was then heated to 80° C. for 1 h. Upon completion, reaction was allowed to cool to ambient temperature and partitioned between water and EtOAc. EtOAc layer washed with brine, dried over Na$_2$SO$_4$, and concentrated in vacuo. The crude product was purified by silica gel flash chromatography (0-40% EtOAc/hexane) to provide (S)-methyl 2-(2-(1-benzyl-1H-pyrazol-4-yl)-7-(4,4-dimethylpiperidin-1-yl)-5-methylpyrazolo[1,5-a]pyrimidin-6-yl)-2-(tert-butoxy)acetate. This was taken up in 9:1 MeOH:water (1 ml) and LiOH.H$_2$O (0.027 g, 0.64 mmol, 10 equiv) was added. The reaction was heated at 60° C. for 1 h. The reaction was then allowed to cool to ambient temperature, filtered, and purified directly via preparative LC/MS with the following conditions: Column: Waters XBridge C18, 19×200 mm, 5-μm particles; Guard Column: Waters XBridge C18, 19×10 mm, 5-μm particles; Mobile Phase A: water; Mobile Phase B: acetonitrile; Buffer: 20-mM ammonium hydroxide; Gradient: 20-95% B over 20.5 minutes, then a 7.0 minute hold at 95% B; Flow: 25 mL/min, to provide the product (0.016 g, 46%). 1H NMR (500 MHz, DMSO-$d_6$) δ 8.29 (s, 1H), 7.93 (s, 1H), 7.39-7.26 (m, 5H), 6.61 (s, 1H), 5.51 (s, 1H), 5.41 (s, 2H), 4.40-3.80 (m, 4H), 2.48 (s, 3H), 1.58 (br. s., 2H), 1.45 (br. s., 2H), 1.14 (s, 9H), 1.07 (br. s., 6H); LCMS (ESI, M+1): 531.30.

Example 40

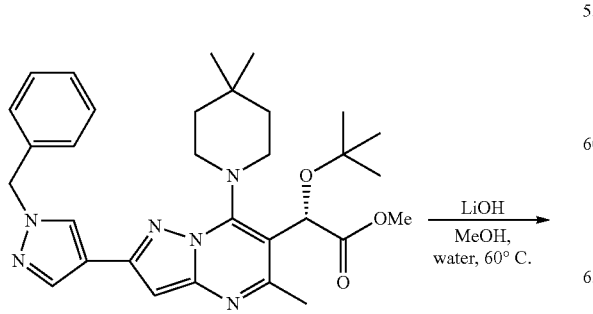

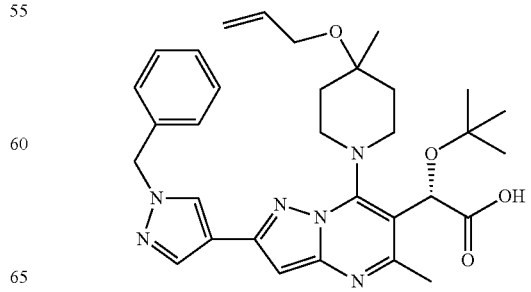

(S)-2-(7-(4-(Allyloxy)-4-methylpiperidin-1-yl)-2-(1-benzyl-1H-pyrazol-4-yl)-5-methylpyrazolo[1,5-a]pyrimidin-6-yl)-2-(tert-butoxy)acetic acid A solution of (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (50 mg, 0.098 mmol, 1 equiv), (1-benzyl-1H-pyrazol-4-yl)boronic acid (29.7 mg, 0.147 mmol, 1.5 equiv), and 2.0 M aqueous potassium phosphate (147 μl, 0.294 mmol, 3 equiv) in DMF (o.49 mL) was sparged with nitrogen for 10 min. Pd(dppf)$_2$ (8.02 mg, 9.81 μmol, 0.1 equiv) was added and the reation was heated to 80° C. for 1 h. Upon cooling to ambient temperature, the reaction was diluted with EtOAc and washed with water. The EtOAc layer was dried (Na$_2$SO$_4$) and concentrated in vacuo. To the crude product was then added water (0.5 mL), MeOH (0.5 mL), and LiOH monohydrate (123 mg, 2.94 mmol, 30 equiv). The reaction was heated at 60° C. for 2 h. Upon cooling to ambient temperature, the mixture was filtered and then purified via preparative LC/MS with the following conditions: Column: Waters XBridge C18, 19×200 mm, 5-μm particles; Guard Column: Waters XBridge C18, 19×10 mm, 5-μm particles; Mobile Phase A: water; Mobile Phase B: acetonitrile; Buffer: 20-mM ammonium hydroxide; Gradient: 20-95% B over 20.5 minutes, then a 7.0 minute hold at 95% B; Flow: 25 mL/min to provide the product (9.7 mg, 17%). $^1$H NMR (500 MHz, DMSO-d$_6$) δ 8.25 (br. s., 1H), 7.93 (s, 1H), 7.40-7.27 (m, 5H), 6.63 (s, 1H), 5.99 (br. s., 1H), 5.68-5.50 (m, 1H), 5.40 (s, 2H), 5.39-5.34 (m, 1H), 5.11 (d, J=10.1 Hz, 1H), 3.97 (br. s., 2H), 3.78-3.06 (m, 4H), 2.48 (br. s., 3H), 1.81 (br. s., 2H), 1.60 (br. s., 2H), 1.26 (br. s., 3H), 1.14 (s, 9H); LCMS (ESI, M): 572.3.

The following Example was prepared according to the above procedure using appropriate boronic acid Example 41

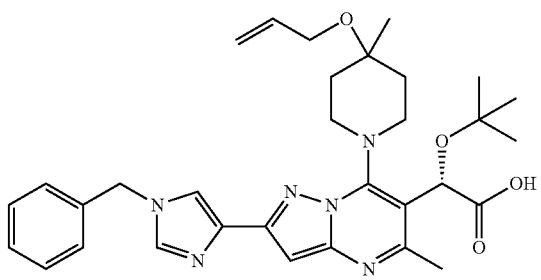 [SMILES: C=CCOC1(C)CCN(c2c([C@H](OC(C)(C)C)C(=O)O)c(C)nc3cc(-c4cn(Cc5ccccc5)cn4)nn23)CC1]

(S)-2-(7-(4-(Allyloxy)-4-methylpiperidin-1-yl)-2-(1-benzyl-1H-imidazol-4-yl)-5-methylpyrazolo[1,5-a]pyrimidin-6-yl)-2-(tert-butoxy)acetic acid $^1$H NMR (500 MHz, DMSO-d$_6$) δ 7.90 (br. s., 1H), 7.51 (br. s., 1H), 7.42-7.36 (m, 2H), 7.35-7.29 (m, 3H), 6.64 (s, 1H), 6.04-5.89 (m, 1H), 5.78-5.63 (m, 1H), 5.36 (d, J=17.4 Hz, 1H), 5.29 (s, 2H), 5.02 (br. s., 1H), 3.94 (br. s., 2H), 3.72-3.41 (m, 4H), 2.49 (br. s., 3H), 1.96-1.58 (m, 4H), 1.25 (br. s., 3H), 1.16 (s, 9H); LCMS (ESI, M+1): 573.4.

It will be evident to one skilled in the art that the present disclosure is not limited to the foregoing illustrative examples, and that it can be embodied in other specific forms without departing from the essential attributes thereof.

It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

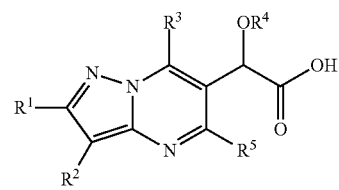

where:
R$^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, or benzimidazolyl, and is substituted with 0-3 substituents selected from halo, alkyl, haloalkyl, alkenyl, Ar$^1$, (Ar$^1$)alkyl, and (Ar$^1$)O;
or R$^1$ is pyrrolidinonyl, oxazolidinonyl, or imidazolonyl, and is substituted with 0-1 substituents selected from Ar$^1$, (Ar$^1$)alkyl, and (Ar$^1$)O;
R$^2$ is hydrogen, halo, or alkyl;
R$^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or R$^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
R$^4$ is alkyl or haloalkyl;
R$^5$ is alkyl; and
Ar$^1$ is phenyl substituted with 0-3 substituents selected from halo, cyano, alkyl, haloalkyl, alkoxy, haloalkoxy, and alkenyloxy;
or a pharmaceutically acceptable salt thereof.

2. A compound of claim 1 where:
R$^1$ is is thienyl, pyrazolyl, imidazolyl, oxazolyl, thiazolyl, oxadiazolyl, indolyl, benzofuranyl, benzothiophenyl, or benzimidazolyl, and is substituted with 0-3 substituents selected from halo, alkyl, haloalkyl, alkenyl, Ar$^1$, (Ar$^1$)alkyl, and (Ar$^1$)O;
or R$^1$ is pyrrolidinonyl, oxazolidinonyl, or imidazolonyl, and is substituted with 0-1 substituents selected from Ar$^1$, (Ar$^1$)alkyl, and (Ar$^1$)O;
R$^2$ is hydrogen, halo, or alkyl;
R$^3$ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or R$^3$ is cyclohexyl, cyclohexenyl, or chromanyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
R$^4$ is alkyl or haloalkyl;

R⁵ is alkyl; and

Ar¹ is phenyl substituted with 0-3 substituents selected from halo, cyano, alkyl, haloalkyl, alkoxy, haloalkoxy, and alkenyloxy;

or a pharmaceutically acceptable salt thereof.

3. A compound of claim 1 where R¹ is thienyl, pyrazolyl, imidazolyl, oxazolyl, thiazolyl, oxadiazolyl, indolyl, benzofuranyl, benzothiophenyl, or benzimidazolyl, and is substituted with 0-3 substituents selected from halo, alkyl, haloalkyl, alkenyl, Ar¹, (Ar¹)alkyl, and (Ar¹)O.

4. A compound of claim 1 where R¹ is pyrrolidinonyl, oxazolidinonyl, or imidazolonyl, and is substituted with 0-1 substituents selected from Ar¹, (Ar¹)alkyl, and (Ar¹)O.

5. A compound of claim 1 where R² is hydrogen.

6. A compound of claim 1 where R³ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

7. A compound of claim 1 where R³ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

8. A compound of claim 1 where R⁴ is alkyl.

9. A compound of claim 1 selected from the group consisting of (2S)-2-(tert-Butoxy)-2-(2-(5-chloro-1H-benzo[d]imidazol-2-yl)-7-(8-fluoro-5-methylchroman-6-yl)-5-methylpyrazolo[1,5-a]pyrimidin-6-yl)acetic acid;

(2S)-2-(tert-Butoxy)-2-(2-(5-chloro-1-methyl-1H-benzo[d]imidazol-2-yl)-7-(8-fluoro-5-methylchroman-6-yl)-5-methylpyrazolo[1,5-a]pyrimidin-6-yl)acetic acid;

(2S)-2-(tert-Butoxy)-2-(2-(6-chloro-1-methyl-1H-benzo[d]imidazol-2-yl)-7-(8-fluoro-5-methylchroman-6-yl)-5-methylpyrazolo[1,5-a]pyrimidin-6-yl)acetic acid;

(2S)-2-(tert-Butoxy)-2-(7-(8-fluoro-5-methylchroman-6-yl)-5-methyl-2-(5-phenyl-1H-benzo[d]imidazol-2-yl)pyrazolo[1,5-a]pyrimidin-6-yl)acetic acid;

(2S)-2-(tert-Butoxy)-2-(7-(8-fluoro-5-methylchroman-6-yl)-2-(5-(4-fluorobenzyl)thiazol-2-yl)-5-methylpyrazolo[1,5-a]pyrimidin-6-yl)acetic acid;

(2S)-2-(tert-Butoxy)-2-(7-(8-fluoro-5-methylchroman-6-yl)-2-(5-(4-fluorobenzyl)oxazol-2-yl)-5-methylpyrazolo[1,5-a]pyrimidin-6-yl)acetic acid;

(2S)-2-(tert-Butoxy)-2-(7-(8-fluoro-5-methylchroman-6-yl)-2-(3-(4-fluorobenzyl)-1,2,4-oxadiazol-5-yl)-5-methylpyrazolo[1,5-a]pyrimidin-6-yl)acetic acid;

(2S)-2-(tert-Butoxy)-2-(7-(8-fluoro-5-methylchroman-6-yl)-2-(5-(4-fluorophenyl)thiazol-2-yl)-5-methylpyrazolo[1,5-a]pyrimidin-6-yl)acetic acid;

(2S)-2-(tert-Butoxy)-2-(7-(8-fluoro-5-methylchroman-6-yl)-2-(5-(3-fluorophenyl)thiazol-2-yl)-5-methylpyrazolo[1,5-a]pyrimidin-6-yl)acetic acid;

(S)-2-(tert-Butoxy)-2-(7-(4,4-dimethylcyclohex-1-en-1-yl)-2-(5-(4-fluorobenzyl)thiazol-2-yl)-5-methylpyrazolo[1,5-a]pyrimidin-6-yl)acetic acid;

(S)-2-(tert-Butoxy)-2-(7-(4,4-dimethylcyclohexyl)-2-(5-(4-fluorobenzyl)thiazol-2-yl)-5-methylpyrazolo[1,5-a]pyrimidin-6-yl)acetic acid;

(S)-2-(tert-Butoxy)-2-(7-(4,4-dimethylcyclohex-1-en-1-yl)-2-(5-(4-fluorobenzyl)oxazol-2-yl)-5-methylpyrazolo[1,5-a]pyrimidin-6-yl)acetic acid;

(S)-2-(tert-Butoxy)-2-(7-(4,4-dimethylpiperidin-1-yl)-2-(5-(4-fluorobenzyl)thiazol-2-yl)-5-methylpyrazolo[1,5-a]pyrimidin-6-yl)acetic acid;

(2S)-2-(tert-Butoxy)-2-(7-(4,4-dimethylpiperidin-1-yl)-2-(5-(1-(4-fluorophenyl)ethyl)thiazol-2-yl)-5-methylpyrazolo[1,5-a]pyrimidin-6-yl)acetic acid;

(S)-2-(tert-Butoxy)-2-(7-(4,4-dimethylpiperidin-1-yl)-2-(5-(4-fluoro-3-methylbenzyl)thiazol-2-yl)-5-methylpyrazolo[1,5-a]pyrimidin-6-yl)acetic acid;

(S)-2-(tert-Butoxy)-2-(7-(4,4-dimethylpiperidin-1-yl)-2-(5-(4-fluorophenethyl)thiazol-2-yl)-5-methylpyrazolo[1,5-a]pyrimidin-6-yl)acetic acid;

(S)-2-(tert-Butoxy)-2-(7-(4-ethyl-4-methylpiperidin-1-yl)-2-(5-(4-fluorobenzyl)thiazol-2-yl)-5-methylpyrazolo[1,5-a]pyrimidin-6-yl)acetic acid;

(S)-2-(tert-Butoxy)-2-(2-(5-(4-fluorobenzyl)thiazol-2-yl)-7-(4-hydroxy-4-methylpiperidin-1-yl)-5-methylpyrazolo[1,5-a]pyrimidin-6-yl)acetic acid;

(S)-2-(tert-Butoxy)-2-(2-(5-(4-fluorobenzyl)thiazol-2-yl)-5-methyl-7-(4-methyl-5,6-dihydropyridin-1(2H)-yl)pyrazolo[1,5-a]pyrimidin-6-yl)acetic acid;

(S)-2-(tert-Butoxy)-2-(2-(5-(4-fluorobenzyl)thiazol-2-yl)-5-methyl-7-(4-phenyl-5,6-dihydropyridin-1(2H)-yl)pyrazolo[1,5-a]pyrimidin-6-yl)acetic acid;

(S)-2-(tert-Butoxy)-2-(2-(5-(4-fluorobenzyl)thiazol-2-yl)-7-(4-(hydroxymethyl)-4-methylpiperidin-1-yl)-5-methylpyrazolo[1,5-a]pyrimidin-6-yl)acetic acid;

(S)-2-(tert-Butoxy)-2-(2-(5-(4-fluorobenzyl)thiazol-2-yl)-7-(4-methoxy-4-methylpiperidin-1-yl)-5-methylpyrazolo[1,5-a]pyrimidin-6-yl)acetic acid;

(S)-2-(tert-Butoxy)-2-(2-(5-(4-fluorobenzyl)thiazol-2-yl)-5-methyl-7-(4-methyl-4-vinylpiperidin-1-yl)pyrazolo[1,5-a]pyrimidin-6-yl)acetic acid;

(S)-2-(tert-Butoxy)-2-(7-(4-cyclopropyl-4-methylpiperidin-1-yl)-2-(5-(4-fluorobenzyl)thiazol-2-yl)-5-methylpyrazolo[1,5-a]pyrimidin-6-yl)acetic acid;

(S)-2-(tert-Butoxy)-2-(7-(4,4-dimethylpiperidin-1-yl)-2-(5-(4-fluorobenzyl)thiophen-2-yl)-5-methylpyrazolo[1,5-a]pyrimidin-6-yl)acetic acid;

(S)-2-(2-(3-Benzyl-2-oxoimidazolidin-1-yl)-7-(4,4-dimethylpiperidin-1-yl)-5-methylpyrazolo[1,5-a]pyrimidin-6-yl)-2-(tert-butoxy)acetic acid;

(2S)-2-(2-(4-Benzyl-2-oxooxazolidin-3-yl)-7-(4,4-dimethylpiperidin-1-yl)-5-methylpyrazolo[1,5-a]pyrimidin-6-yl)-2-(tert-butoxy)acetic acid;

(2S)-2-(2-(5-Benzyl-2-oxooxazolidin-3-yl)-7-(4,4-dimethylpiperidin-1-yl)-5-methylpyrazolo[1,5-a]pyrimidin-6-yl)-2-(tert-butoxy)acetic acid;

(2S)-2-(tert-Butoxy)-2-(7-(4,4-dimethylpiperidin-1-yl)-5-methyl-2-(2-oxo-3-phenoxypyrrolidin-1-yl)pyrazolo[1,5-a]pyrimidin-6-yl)acetic acid;

(S)-2-(2-(4-Benzyl-1H-pyrazol-1-yl)-7-(4,4-dimethylpiperidin-1-yl)-5-methylpyrazolo[1,5-a]pyrimidin-6-yl)-2-(tert-butoxy)acetic acid;

(S)-2-(2-(4-Benzyl-1H-imidazol-1-yl)-7-(4,4-dimethylpiperidin-1-yl)-5-methylpyrazolo[1,5-a]pyrimidin-6-yl)-2-(tert-butoxy)acetic acid;

(S)-2-(2-(5 Benzyl-1H-pyrazol-1-yl)-7-(4,4-dimethylpiperidin-1-yl)-5-methylpyrazolo[1,5-a]pyrimidin-6-yl)-2-(tert-butoxy)acetic acid;

(S)-2-(2-(3-Benzyl-1H-pyrazol-1-yl)-7-(4,4-dimethylpiperidin-1-yl)-5-methylpyrazolo[1,5-a]pyrimidin-6-yl)-2-(tert-butoxy)acetic acid;

(S)-2-(7-(4-(Allyloxy)-4-methylpiperidin-1-yl)-2-(4-(2-(allyloxy)benzyl)-1H-pyrazol-1-yl)-5-methylpyrazolo[1,5-a]pyrimidin-6-yl)-2-(tert-butoxy)acetic acid;

(S)-2-(2-(4-Benzyl-3-chloro-1H-pyrazol-1-yl)-7-(4,4-dimethylpiperidin-1-yl)-5-methylpyrazolo[1,5-a]pyrimidin-6-yl)-2-(tert-butoxy)acetic acid;

(S)-2-(2-(1-Benzyl-1H-pyrazol-4-yl)-7-(4,4-dimethylpiperidin-1-yl)-5-methylpyrazolo[1,5-a]pyrimidin-6-yl)-2-(tert-butoxy)acetic acid;

(S)-2-(7-(4-(Allyloxy)-4-methylpiperidin-1-yl)-2-(1-benzyl-1H-pyrazol-4-yl)-5-methylpyrazolo[1,5-a]pyrimidin-6-yl)-2-(tert-butoxy)acetic acid; and (S)-2-(7-(4-(Allyloxy)-4-methylpiperidin-1-yl)-2-(1-benzyl-1H-imidazol-4-yl)-5-methylpyrazolo[1,5-a]pyrimidin-6-yl)-2-(tert-butoxy)acetic acid or a pharmaceutically acceptable salt thereof.

10. A composition useful for treating HIV infection comprising a therapeutic amount of a compound of claim 1 and a pharmaceutically acceptable carrier.

11. The composition of claim 10 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

12. A method for treating HIV infection comprising administering a therapeutically effective amount of a compound of claim 1, or a pharmaceutically acceptable salt thereof, to a patient in need thereof.

13. The method of claim 12 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *